(12) United States Patent
Abrams et al.

(10) Patent No.: US 6,740,098 B2
(45) Date of Patent: May 25, 2004

(54) SURGICAL STABILIZER DEVICES AND METHODS

(75) Inventors: Jerome H. Abrams, St. Paul, MN (US); Claire T. Hovland, Andover, MN (US); Paul J. Robinson, Mahtomedi, MN (US)

(73) Assignee: Surgical Connections, Inc., Andover, MN (US)

( * ) Notice: Subject to any disclaimer, the term of this patent is extended or adjusted under 35 U.S.C. 154(b) by 122 days.

(21) Appl. No.: 09/939,052

(22) Filed: Aug. 24, 2001

(65) Prior Publication Data

US 2002/0072761 A1 Jun. 13, 2002

Related U.S. Application Data

(63) Continuation-in-part of application No. 09/616,411, filed on Jul. 14, 2000, and a continuation-in-part of application No. 09/309,617, filed on May 11, 1999, now Pat. No. 6,149,667.
(60) Provisional application No. 60/085,054, filed on May 11, 1998, provisional application No. 60/191,932, filed on Mar. 24, 2000, and provisional application No. 60/228,014, filed on Aug. 24, 2000.

(51) Int. Cl.[7] .............................................. A61B 17/04
(52) U.S. Cl. ...................................... 606/148; 606/139
(58) Field of Search ......................... 606/139; 128/898, 128/148

(56) References Cited

U.S. PATENT DOCUMENTS

| | | | |
|---|---|---|---|
| 2,638,901 A | 5/1953 | Sugarbaker |
| 3,661,155 A | 5/1972 | Lindan |
| 4,019,499 A | 4/1977 | Fitzgerald |
| 4,139,006 A | 2/1979 | Corey |
| 4,294,255 A | 10/1981 | Geroc |

(List continued on next page.)

FOREIGN PATENT DOCUMENTS

| | | |
|---|---|---|
| DE | 9107166 U | 9/1991 |
| EP | 0282157 | 9/1988 |
| EP | 0517488 | 12/1992 |
| FR | 2612392 | 9/1988 |
| NL | 7400096 | 7/1975 |
| WO | WO 92/17117 | 10/1992 |
| WO | WO 97/27893 | 8/1997 |
| WO | WO 97/32527 | 9/1997 |
| WO | WO 98/03118 | 1/1998 |
| WO | WO 98/11814 | 3/1998 |
| WO | WO 99/00059 | 1/1999 |
| WO | WO 99/58081 | 5/1999 |
| WO | WO 00/03759 | 1/2000 |
| WO | WO 00/28902 | 5/2000 |
| WO | WO 01/72238 | 10/2001 |

OTHER PUBLICATIONS

ACOG Patient Education brochure "Gynecologic Problems: Urinary Incontinence", The American College of Obstetricians and Gynecologists, Jan. 1996.

(List continued on next page.)

Primary Examiner—Gary Jackson
(74) Attorney, Agent, or Firm—Dicke, Billig & Czaja, PLLC

(57) ABSTRACT

Surgical devices and methods achieve a desired configuration of one or more anatomical structures, e.g. by suction or inflation, and then optionally deploy a stabilizing or fastening agent or holding device, for example a helical staple, to stabilize the anatomical structure in the desired configuration. Aspects of the invention can be used in the treatment of incontinence, coronary artery blockage, and blockages or strictures in other anatomical structures. Additionally, embodiments of the invention also can be used to create anastomoses between anatomical structures, and/or to create or reverse functional vasectomies, tubal ligations and the like. Aspects of the invention are particularly (though not exclusively) applicable in minimally invasive surgical settings.

59 Claims, 37 Drawing Sheets

U.S. PATENT DOCUMENTS

| | | |
|---|---|---|
| 4,350,160 A | 9/1982 | Kolesov et al. |
| 4,686,962 A | 8/1987 | Haber |
| 4,990,153 A | 2/1991 | Richards |
| 5,007,894 A | 4/1991 | Enhorning |
| 5,222,963 A | 6/1993 | Brinkerhoff et al. |
| 5,234,409 A | 8/1993 | Goldberg et al. |
| 5,250,058 A | 10/1993 | Miller et al. |
| 5,256,133 A | 10/1993 | Spitz |
| 5,330,503 A | 7/1994 | Yoon |
| 5,346,501 A | 9/1994 | Regula et al. |
| 5,385,156 A | 1/1995 | Oliva |
| 5,395,030 A | 3/1995 | Kuramoto et al. |
| 5,403,326 A | 4/1995 | Harrison et al. |
| 5,417,226 A | 5/1995 | Juma |
| 5,503,635 A | 4/1996 | Sauer et al. |
| 5,520,606 A | 5/1996 | Schoolman et al. |
| 5,611,515 A | 3/1997 | Benderev et al. |
| 5,647,836 A | 7/1997 | Blake, III et al. |
| 5,782,844 A | 7/1998 | Yoon et al. |
| 5,810,851 A | 9/1998 | Yoon |
| 5,810,882 A | 9/1998 | Bolduc et al. |
| 5,839,639 A | 11/1998 | Sauer et al. |
| 5,868,760 A | 2/1999 | McGuckin, Jr. |
| 5,947,983 A | 9/1999 | Solar et al. |
| 6,119,913 A | 9/2000 | Adams et al. |
| 6,126,058 A | 10/2000 | Adams et al. |
| 6,149,667 A | 11/2000 | Hovland et al. |
| 6,343,731 B1 | 2/2002 | Adams et al. |
| 6,517,566 B1 | 2/2003 | Hovland et al. |
| 2002/0020732 A1 | 2/2002 | Adams et al. |

OTHER PUBLICATIONS

"Urethral Sphincter Incompetence (Stress Incontinence)", by S.L. Stanton, Urodynamics Principles, Practice and Application, Chapter 22, 1984, pp. 229–241.

"The Scott Artificial Urinary Sphincter", Urodynamics Principles, Practice and Application, Chapter 35, 1984, pp. 374–377.

"Urinary Incontinence in the Female: Stress Urinary Incontinence", by Linda Shortliffe, M.D. et al., Campbell's Urology, Fifth Edition, vol. 3, Chapter 73, 1986, pp. 2680–2711.

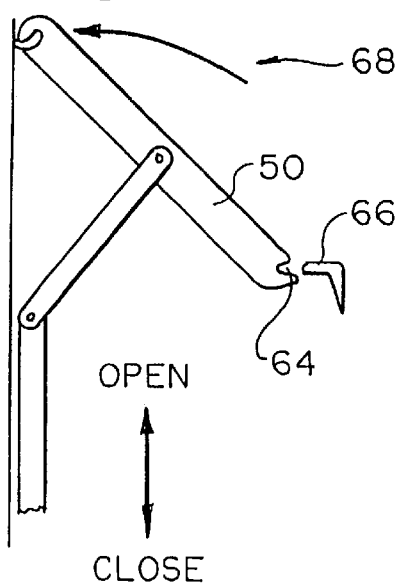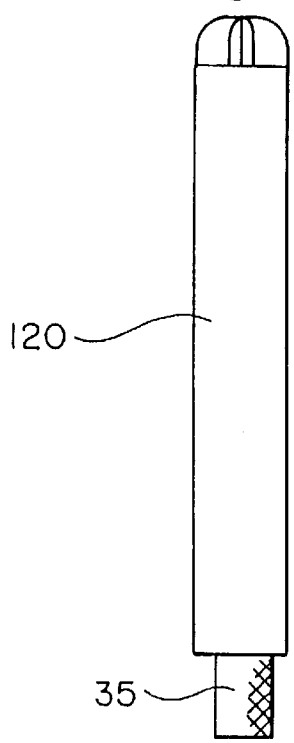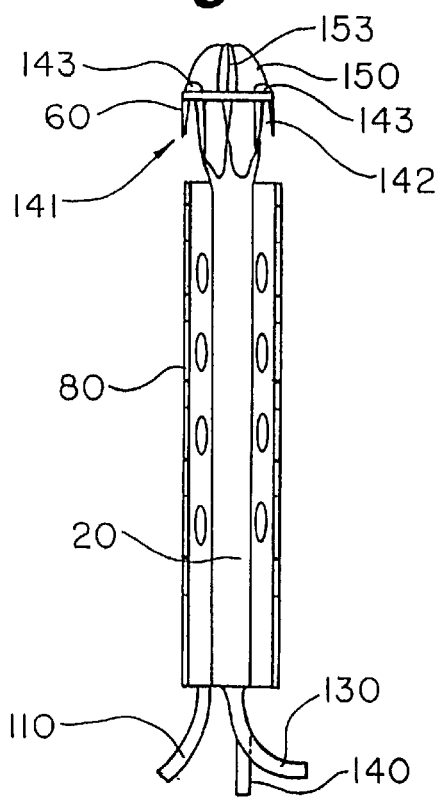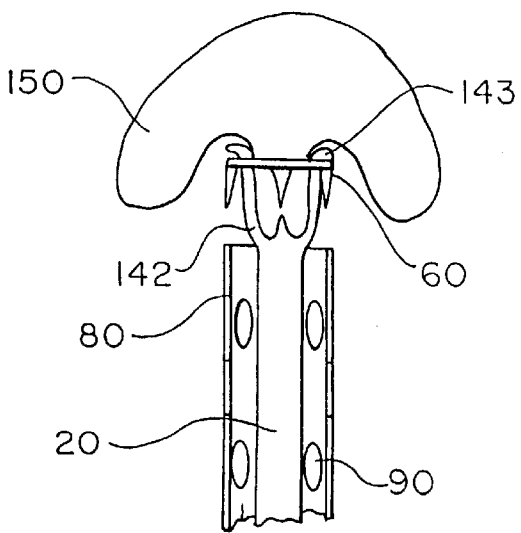

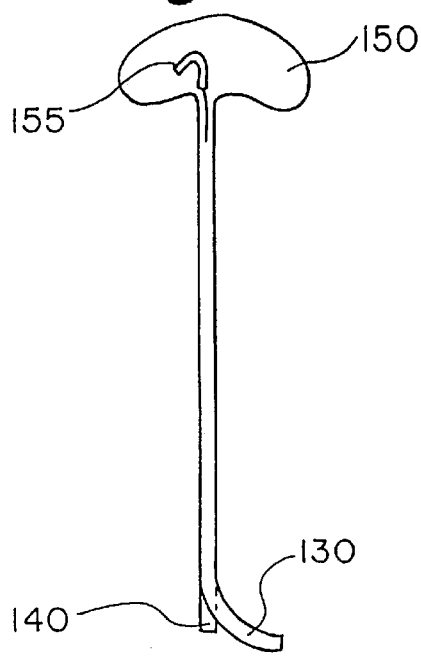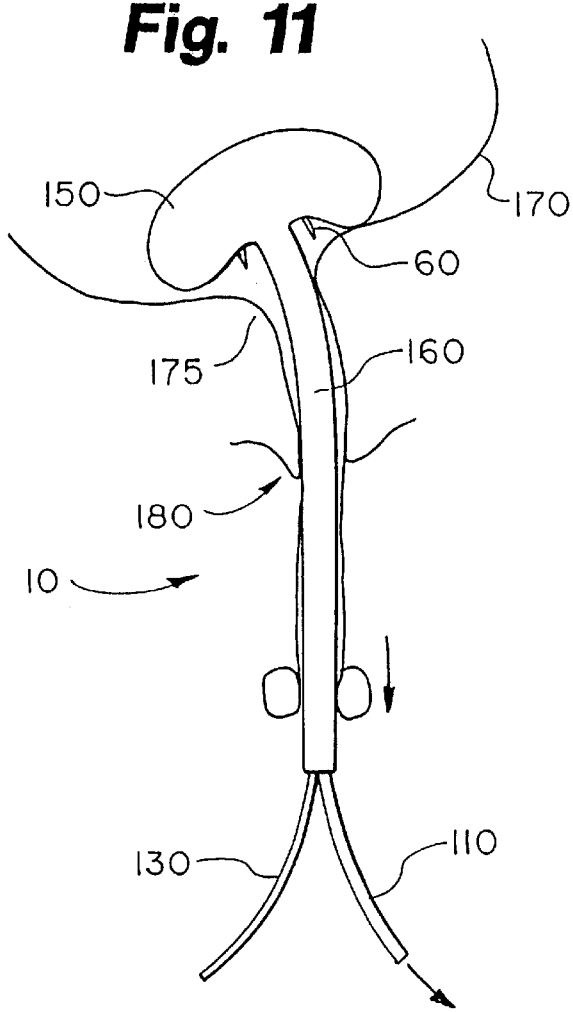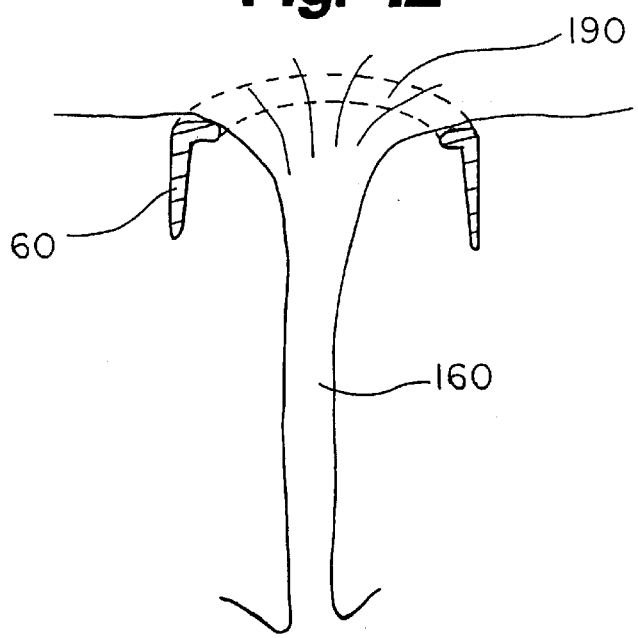

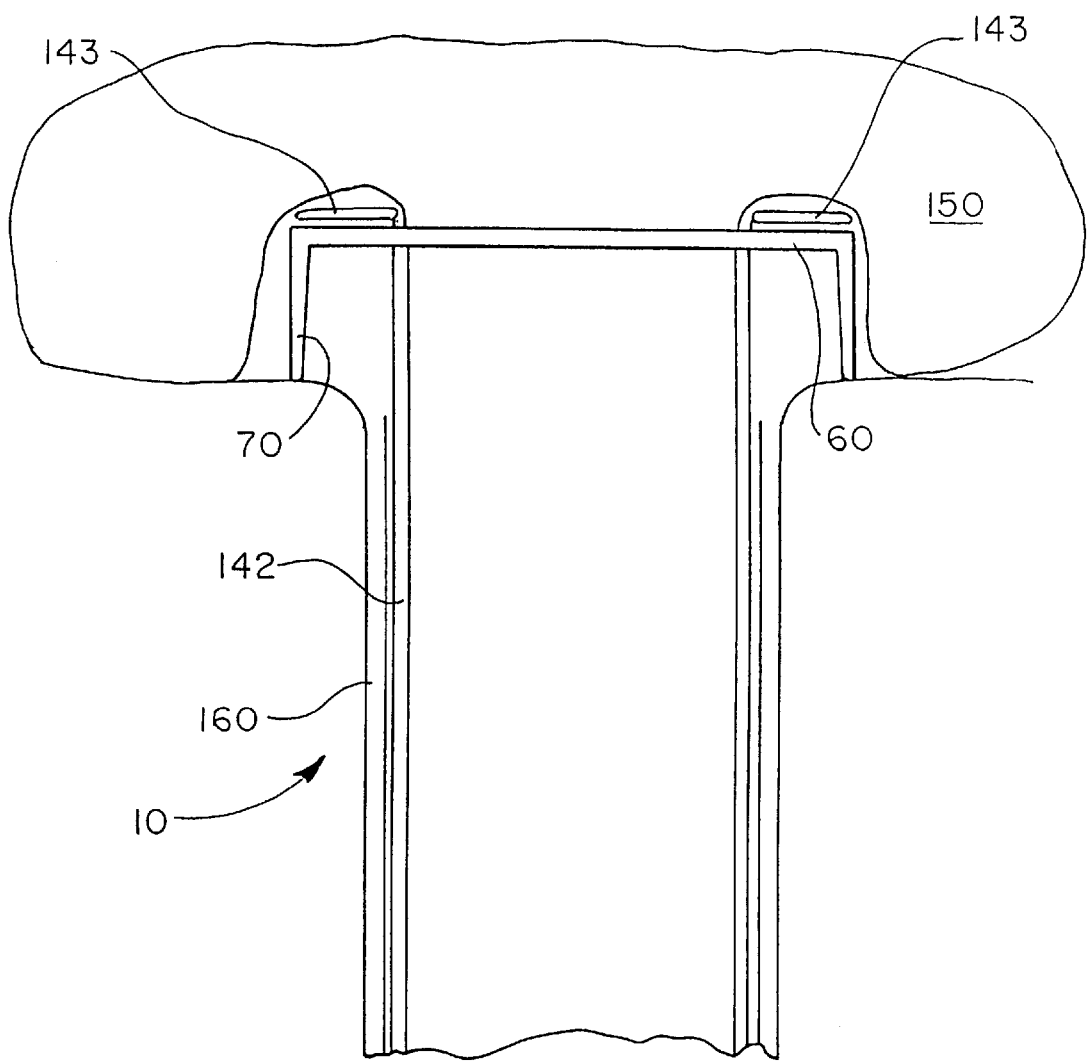

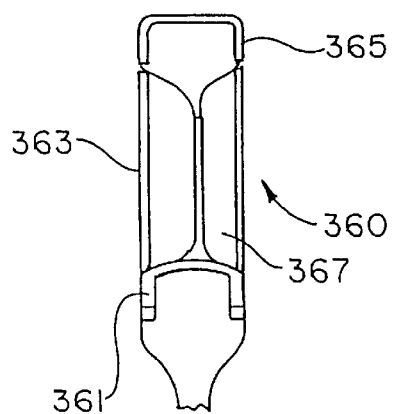
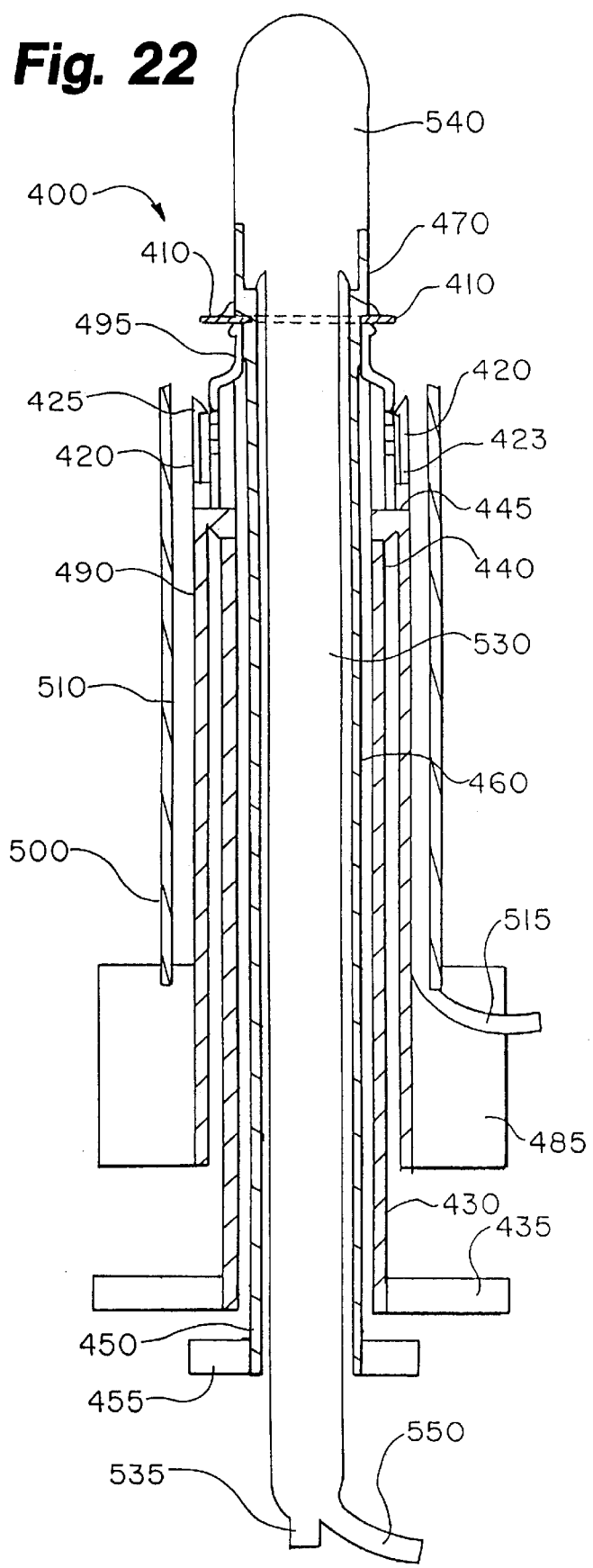
Fig. 21
Fig. 22

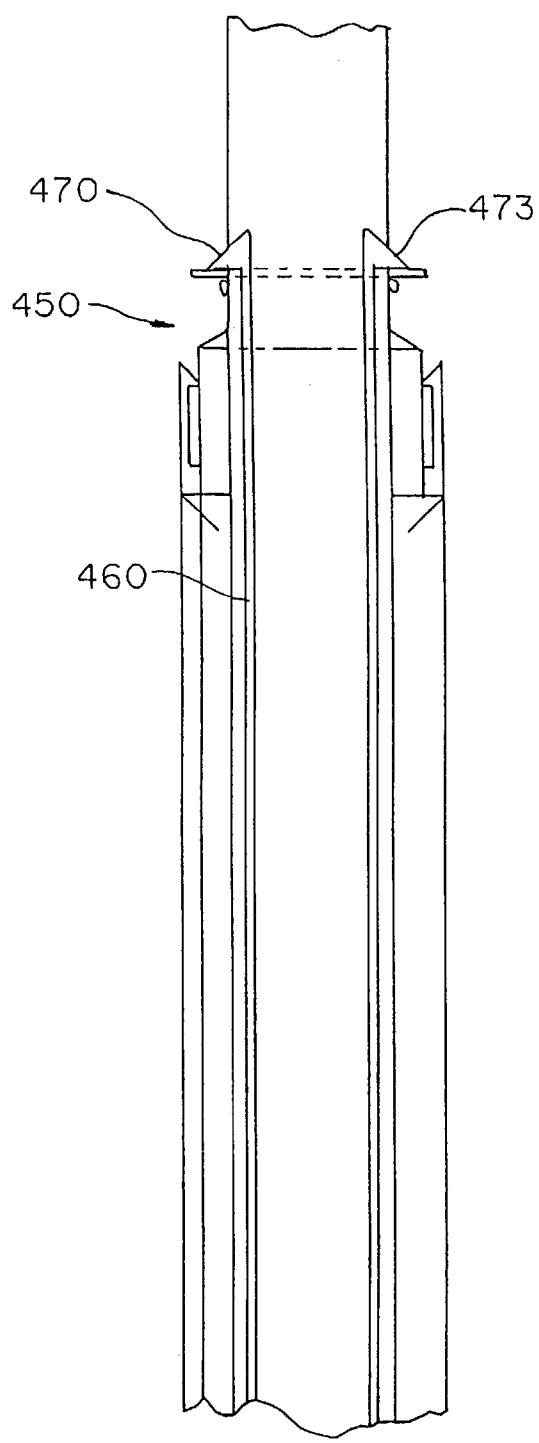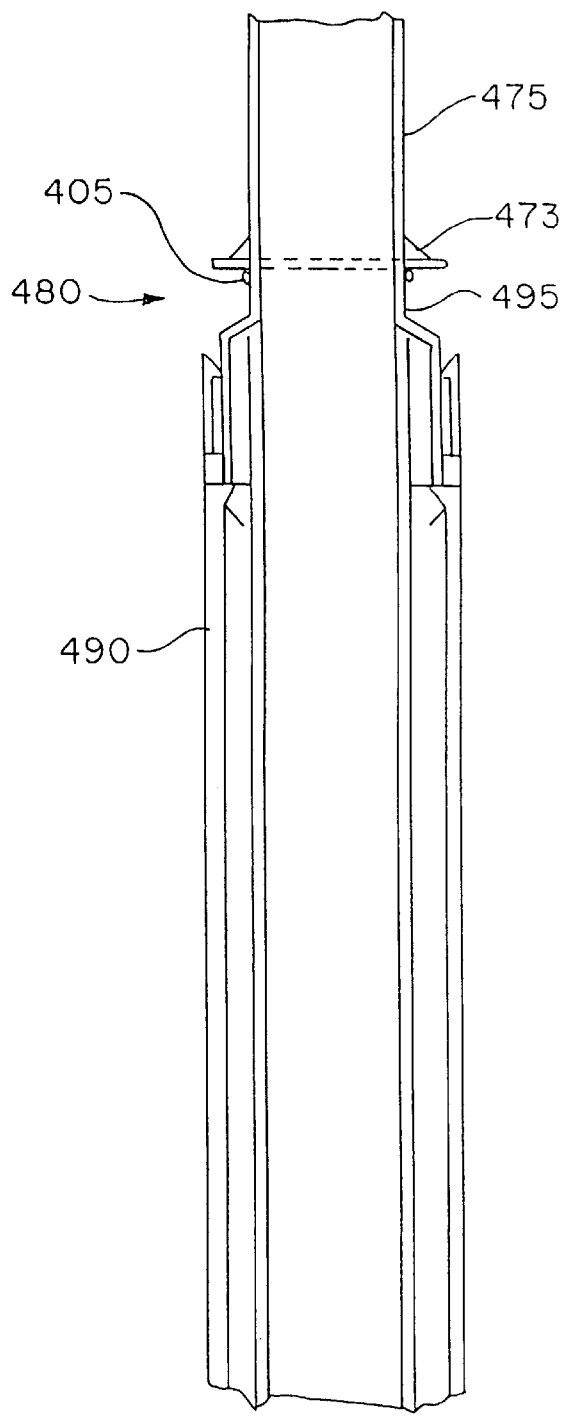

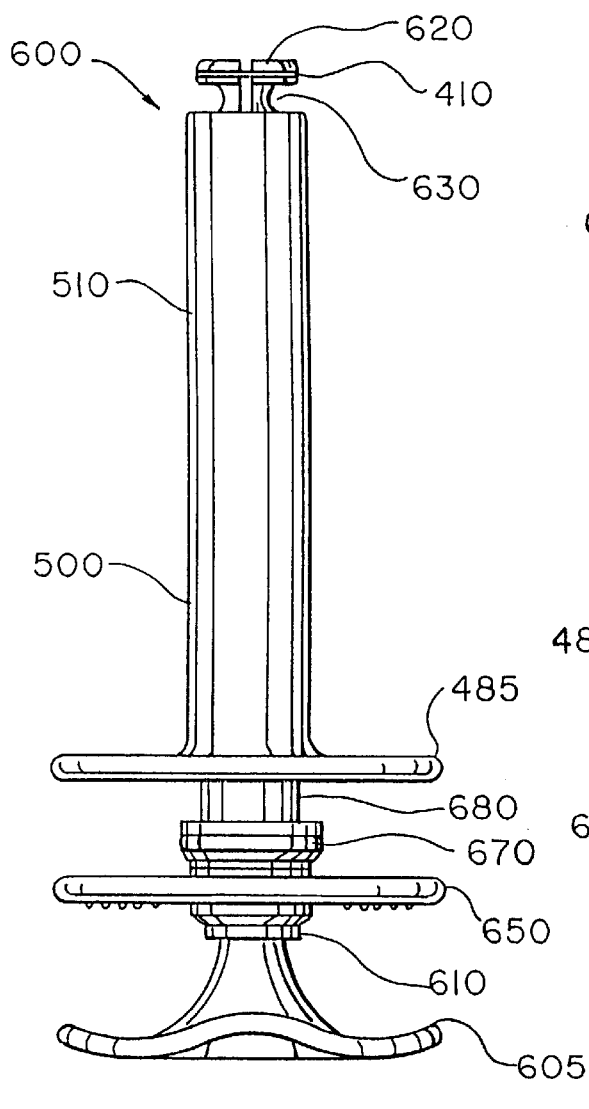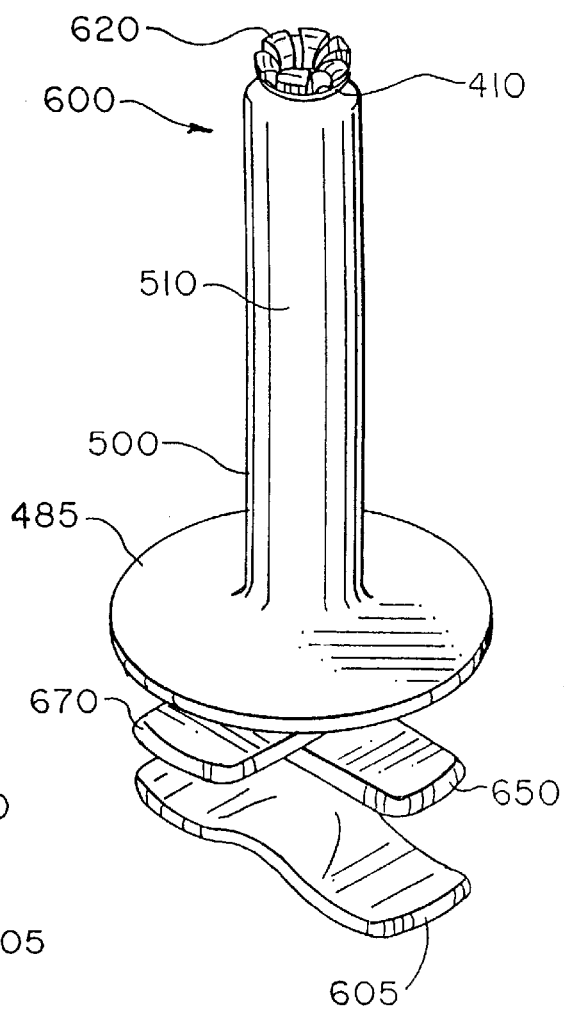

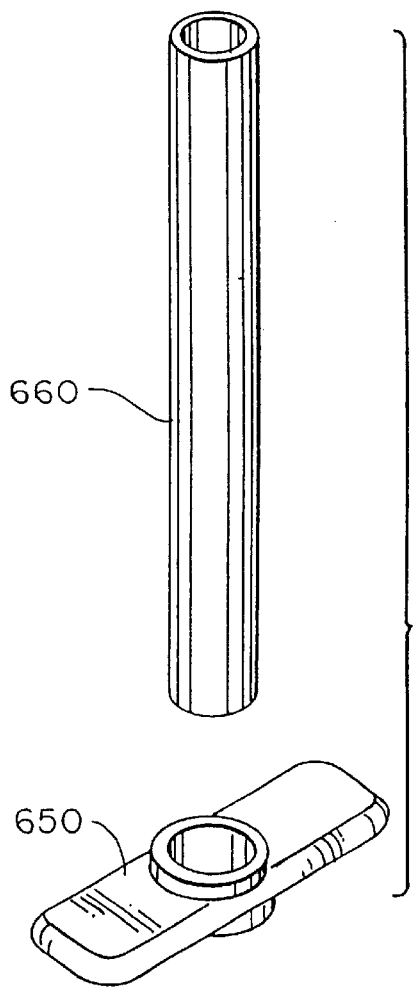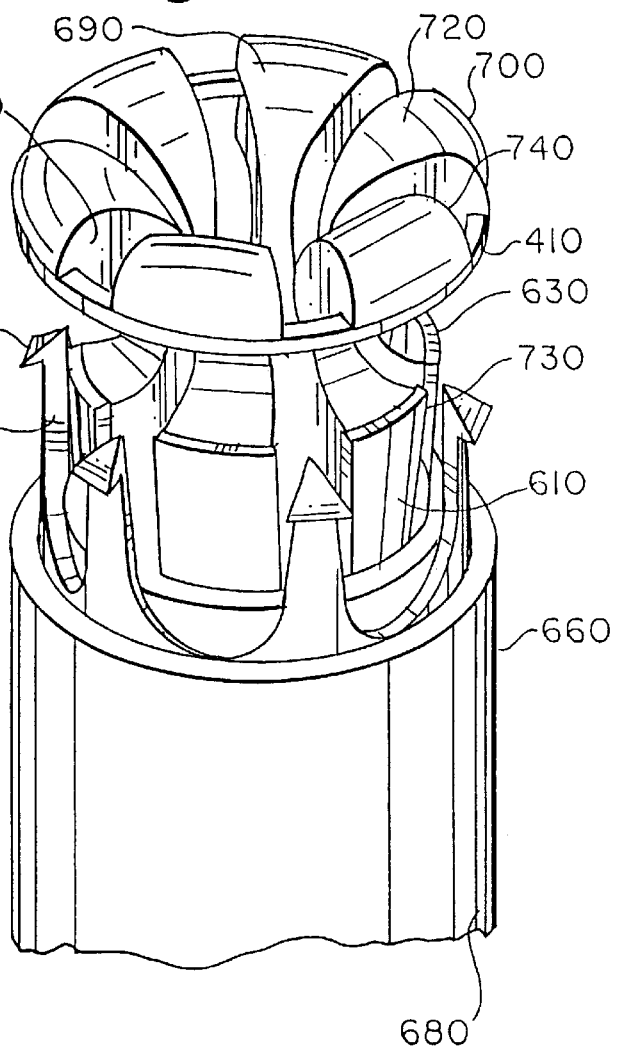

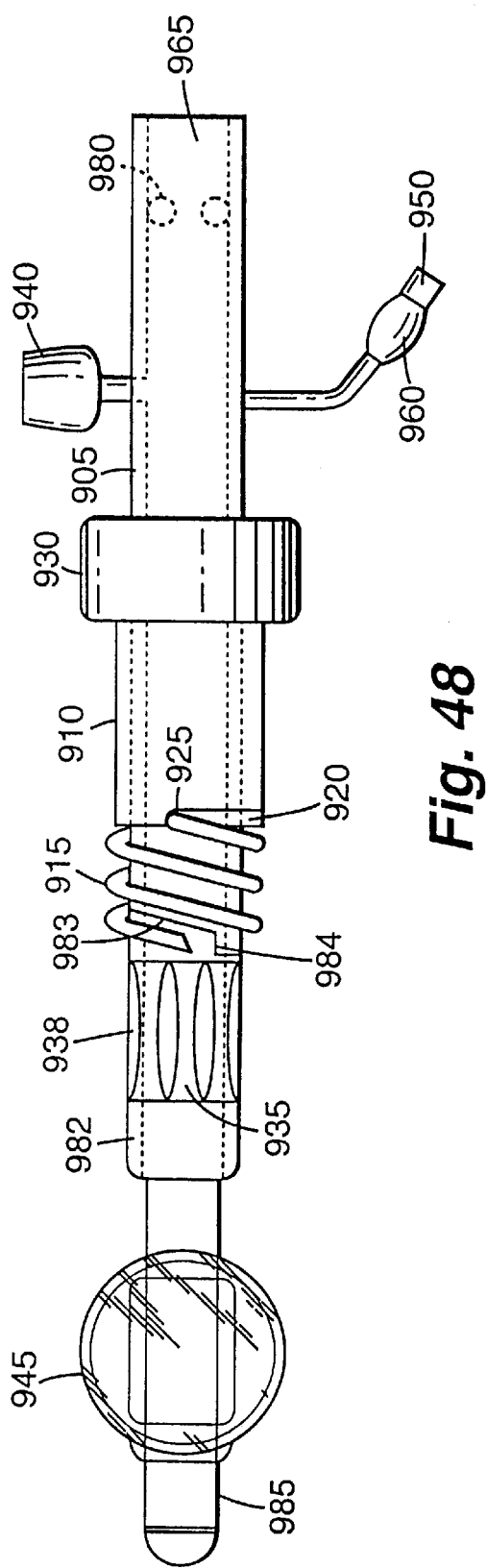
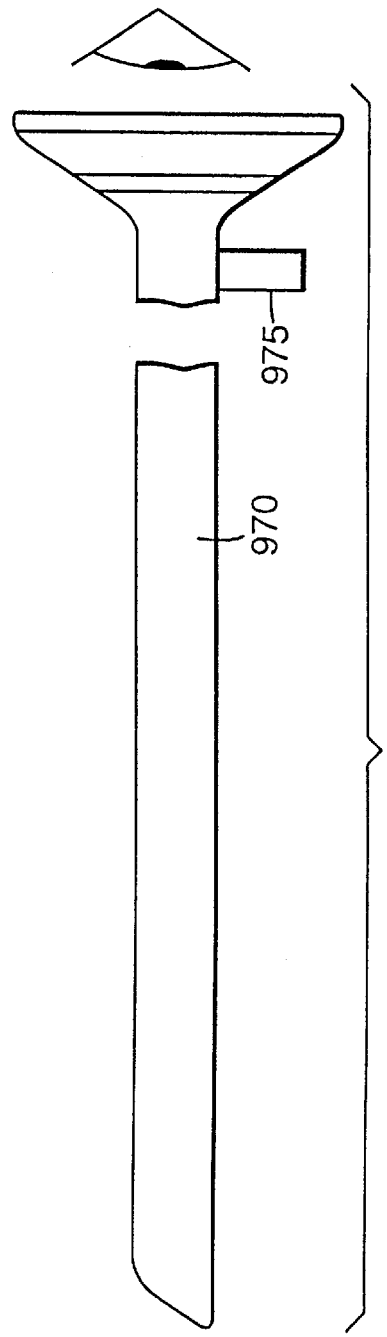
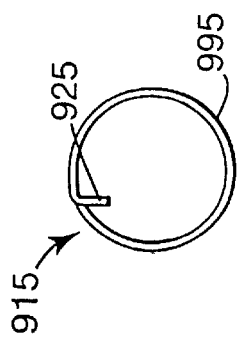
Fig. 48
Fig. 49
Fig. 50

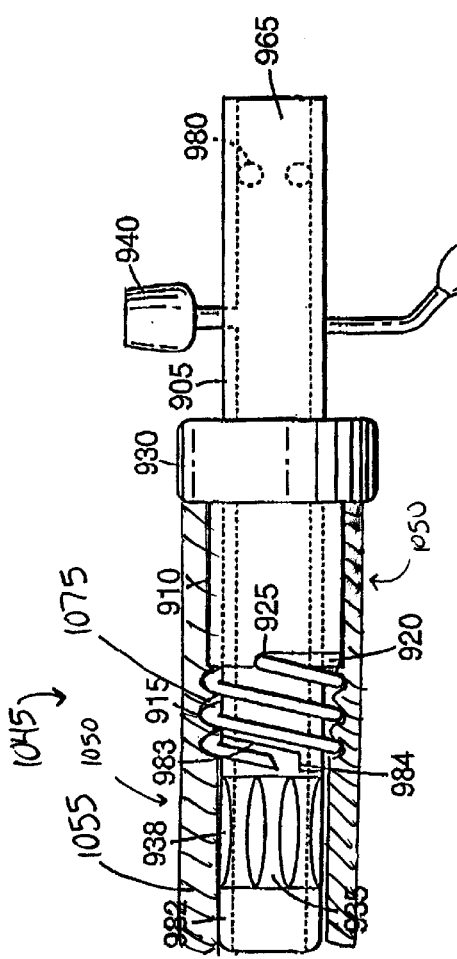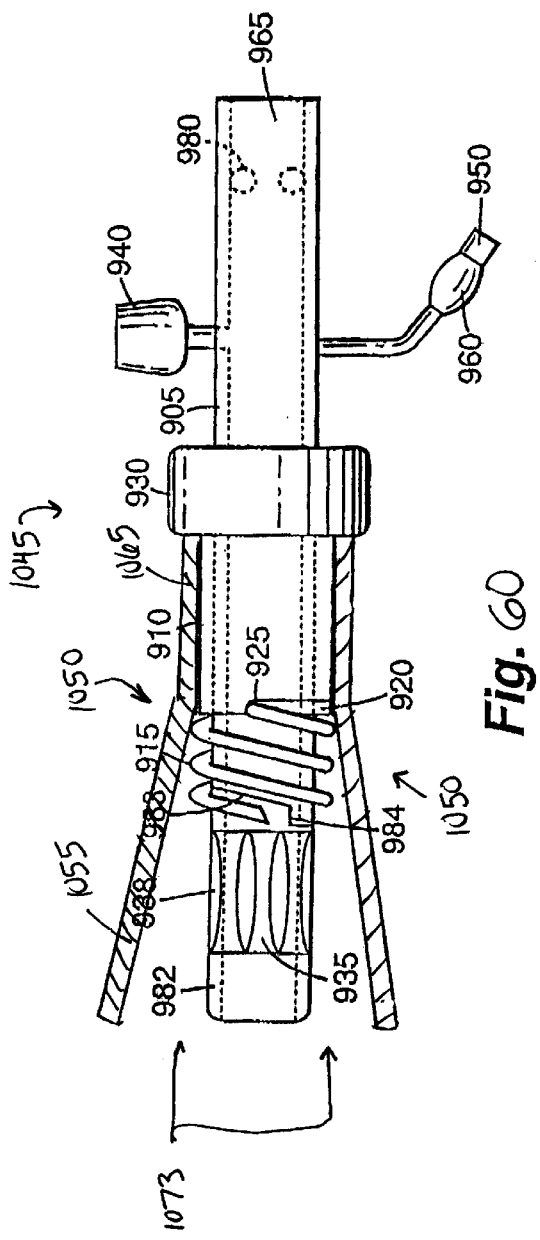

SURGICAL STABILIZER DEVICES AND METHODS

CROSS-REFERENCE TO RELATED APPLICATIONS

The present application is a Continuation-In-Part of U.S. application Ser. No. 09/616,411, filed Jul. 14, 2000, which claims priority under 35 U.S.C. §119(e) to U.S. application Ser. No. 60/191,932, filed Mar. 24, 2000 and which is a Continuation-In-Part of U.S. application Ser. No. 09/309,617, filed May 11, 1999, now U.S. Pat. No. 6,149,667, which application claims priority under 35 U.S.C. §119(e) to U.S. application Ser. No. 60/085,054, filed May 11, 1998; further, the present application claims priority under 35 U.S.C. §119(e) to U.S. application Ser. No. 60/228,014, filed Aug. 24, 2000. All of the above-identified applications are incorporated herein by reference.

BACKGROUND OF THE INVENTION

1. Field of the Invention

The invention relates to surgical stabilizer devices and methods. More specifically, the invention relates to surgical devices and methods for achieving a desired configuration of one or more anatomical structures, e.g. by suction or inflation, and then optionally for deploying e.g. a helical staple to stabilize the anatomical structure in the desired configuration, or otherwise stabilizing the structure. Embodiments of the invention can be used in the treatment of incontinence, coronary artery blockage, and blockages or strictures in other anatomical structures. Additionally, embodiments of the invention also can be used to create anastomoses between anatomical structures, and/or to create or reverse functional vasectomies, tubal ligations and the like. Aspects of the invention are particularly (though not exclusively) applicable in minimally invasive surgical settings.

Aspects of the invention provide dilation and/or constriction of anatomical structure, and subsequent stabilization, all while maintaining the lumen of the anatomical structure free of stents or other foreign bodies. Patients thus are believed better able to tolerate the treatments and devices described herein than with typical, invasive, intraluminal stents or the like.

Other fields in which embodiments of the invention can be used will become apparent upon reading the remainder of this patent application.

2. Description of Related Art

Commonly assigned U.S. Pat. No. 6,149,667, incorporated herein by reference, provides an implanted support for e.g. the urethral neck of the bladder, substantially preventing urinary leakage caused by transmission of intra-abdominal pressure pulse waves. The support is implanted in a straightforward manner without the significant complexity and invasiveness associated with previously known surgical techniques, and thus provides significant advantages. Pelvic trauma is dramatically reduced. Embodiments of the invention disclosed in the patent can be used in the treatment of stress incontinence, and other types of incontinence, in both males and females.

First-described embodiments of the invention relate to the treatment of incontinence. One particular form of incontinence, stress incontinence, often is caused by weakened muscles in the pelvic floor. Without adequate pelvic support, the bladder and proximal end of the urethra tend to sag, the bladder neck dilates, the proximal urethra widens, and the urethra as a whole shortens. Normal flow resistance from the bladder neck and the urethral sphincter decreases, causing leakage upon increase in intra-abdominal pressure that might be due to coughing, for example. FIG. 1 roughly illustrates three anatomical configurations with respect to pelvic floor 2: normal anatomy 4, descended bladder/urethra 6, and widened bladder neck/shortened urethra 8. FIG. 1 is adapted from Mundy, A. R., ed., *Urodynamics—Principles, Practice and Application,* 1984, p. 229. The *Urodynamics* text is incorporated by reference herein in its entirety.

SUMMARY OF THE INVENTION

Embodiments of the invention provide a permanent implanted support for an anatomical structure, e.g. the urethral neck of the bladder, a coronary artery or other vascular structure, fallopian tubes, vas deferens, stomach, esophagus, intestine, bile duct, rectum, small bowel and/or other anatomical structures. Embodiments of the invention can cause both dilation of anatomical structures, in the manner of e.g. traditional angioplasty procedures, and/or cause constriction or narrowing of anatomical structures. The support is implanted in a straightforward manner without the significant complexity and invasiveness associated with known surgical techniques. The support can remain completely outside the lumen of the anatomical structure if desired. Trauma to the patient is dramatically reduced.

According to particular embodiments of the invention, an apparatus for treatment of anatomical structure having a lumen comprises a pressure differential device constructed to create a pressure differential with respect to the lumen of the anatomical structure, to cause movement of the anatomical structure to a desired configuration for treatment. The apparatus further comprises a stabilizing device, operably coupled with the pressure differential device, to stabilize the anatomical structure in the desired configuration. The pressure differential device can be constructed to create a negative and/or positive pressure differential relative to luminal pressure of the anatomical structure. Particular embodiments of pressure differential device include a vacuum source, suction source and/or positive pressure source with appropriate fluid communication and coupling, and cause constriction of the anatomical structure to the desired configuration and/or dilation of the anatomical structure to the desired configuration. A positive pressure differential device can include an inflatable balloon. The pressure differential device can be constructed and arranged to aid in performing an angioplasty procedure in a coronary artery, tubal ligation or reversal thereof, vasectomy or reversal thereof, incontinence treatment, stomach size reduction, and treatment of varicose veins, to name a few examples.

A stabilizing device according to embodiments of the invention comprises structure for applying a holding device to the anatomical structure, the holding device being constructed to remain applied to the anatomical structure after removal of the apparatus from the vicinity of the anatomical structure. The stabilizing device according to an embodiment of the invention also can comprise the holding device itself. According to particular embodiments, the holding device remains completely outside of the lumen both during and after the surgical procedure. The lumen of the anatomical structure is reduced and/or enlarged when the anatomical structure is in the desired configuration. A stabilizing device according to a particular embodiment comprises a helical staple that is applied to the anatomical structure while it is in the desired configuration, to hold the desired configuration after removal of the apparatus.

One particular pressure differential device comprises a set of suction apertures fluidly coupled to a suction source, the set of suction apertures constructed and arranged to cause movement of the anatomical structure to the desired configuration. The set of suction apertures can be a first set of suction apertures, the pressure differential device further comprising a second set of suction apertures fluidly coupled to a suction source. The first and the second sets of suction apertures can be constructed and arranged to cause relative movement of two portions of the anatomical structure toward each other to form an anastomosis. At least one of these sets of suction apertures can be constructed to move toward the other of the sets of suction apertures to form the anastomosis, optionally upon movement by an operator simultaneously with application of suction via the suction apertures. A plurality of suction apertures can be constructed and arranged to cause relative movement of two portions of the anatomical structure toward each other to facilitate formation of the anastomosis.

A stabilizing device according to a particular embodiment of the invention includes a surgical fastener and an applicator for applying the surgical fastener to the anatomical structure. A generally cylindrical member can be operably coupled with the stabilizing device and the pressure differential device, the surgical fastener, the applicator and at least one of the suction apertures being disposed around the generally cylindrical member. The generally cylindrical member can be a first generally cylindrical member, the apparatus further comprising a second generally cylindrical member operably coupled with the stabilizing device and the pressure differential device. At least another of the suction apertures is disposed around the second generally cylindrical member, according to one embodiment, the first generally cylindrical member and the second generally cylindrical member being generally concentric and disposed for relative movement between them.

A guide can be operably coupled with the stabilizing device to guide movement of the anatomical structure. According to one embodiment, the guide is moveable between a deployed configuration and a non-deployed configuration, generally pivoting or bending outwardly during movement between the two configurations. The guide in the deployed configuration can define a generally V-shaped or conical opening for receiving anatomical structure therein. The guide can define indentations for at least partially receiving a helical staple as a part of the stabilizing device. The guide also can define a general cone shape when in the deployed configuration. Particular embodiments of the invention are especially constructed for at least one of vascular closure, wound closure, and ligation of gastrointestinal hemorrhage.

Other embodiments of the invention are particularly constructed to cause e.g. a fallopian tube or vas deferens to collapse or close tightly on itself upon application of negative pressure. A stabilizing device according to this embodiment comprises a helical staple and helical-staple applicator, the applicator applying the helical staple to the anatomical structure after the anatomical structure has closed upon itself. A wire also can be provided, constructed to deploy within the lumen of the anatomical structure to damage the anatomical structure before it is stabilized by the stabilizing device. The wire can be a resistive wire for applying heat to the anatomical structure.

According to another embodiment, the apparatus further comprises a cutting device, operably coupled with the pressure differential device and the stabilizing device, for cutting the anatomical structure. The stabilizing device also can comprise repair material, and/or structure for applying the repair material to the anatomical structure in the vicinity of the cut anatomical structure. The repair material remains applied to the anatomical structure after removal of the apparatus from the vicinity of the anatomical structure, according to one embodiment.

According to another specific embodiment, apparatus for treatment of anatomical structure having a lumen comprises a movement device constructed to cause movement of the anatomical structure to a desired configuration for treatment, and a stabilizing device, operably coupled with the movement device, constructed to stabilize the anatomical structure in the desired configuration. The movement device can comprise a cutting device for cutting the anatomical structure. The stabilizing device can comprise structure for applying repair material to the anatomical structure in the vicinity of the cut anatomical structure. The repair material can remain applied to the anatomical structure after removal of the apparatus. The stabilizing device further can comprise a surgical fastening agent, such as one defining a helical shape or comprising a helical staple, to hold the repair material in place with respect to the anatomical structure. Particular apparatus embodiments according to the invention are constructed and arranged for use in a blocked coronary artery.

The stabilizing device can comprise a helical staple and an advancement member for contacting and advancing the helical staple into the anatomical structure after the cutting device has cut the anatomical structure. The helical staple is constructed to hold repair material in place on the anatomical structure. According to one embodiment, a single motion of the operator of the apparatus is sufficient to both cut the anatomical structure and to apply the repair material. A cutting device advancement mechanism can advance the cutting device relative to the anatomical structure, e.g. a threaded screw. The anatomical structure can be cut and the repair material applied to the anatomical structure generally simultaneously, according to embodiments of the invention. As with previous embodiments, the stabilizing device can be constructed to remain completely outside of the lumen. A suction device applies suction in the vicinity of the anatomical structure and/or a positive pressure device applies positive pressure in the vicinity of the anatomical structure, according to embodiments of the invention.

According to another aspect of the invention, an apparatus for facilitating treatment of anatomical structure having a lumen comprises a pressure differential device constructed to cause movement of the anatomical structure to a desired, generally stabilized configuration by creating pressure differential from within the lumen, the desired configuration being suitable for further stabilization or treatment, the apparatus further comprising a member constructed to support the pressure differential device from within the lumen. The pressure differential device can comprise a suction device for drawing the anatomical structure toward the pressure differential device and into the desired configuration.

Other features and advantages according to embodiments of the invention will be apparent from the following detailed description.

BRIEF DESCRIPTION OF THE DRAWINGS

Embodiments of the invention will be described with reference to the figures, in which like reference numerals denote like elements and in which:

FIGS. 3–6 are cross-sectional views showing supportive interaction with a staple, according to embodiments of the invention;

FIG. 7 shows an incontinence treatment device in a substantially assembled condition, according to an embodiment of the invention;

FIG. 8 shows the incontinence treatment device of FIG. 7 with the cover removed;

FIG. 9 shows an incontinence treatment device with a deployed balloon, according to an embodiment of the invention;

FIG. 10 shows a balloon and endoscope port according to an embodiment of the invention;

FIG. 11 shows an incontinence treatment device inserted into the urethra and bladder, according to an embodiment of the invention;

FIG. 12 shows an implanted staple with healed-over tissue, according to an embodiment of the invention;

FIG. 13 shows a more detailed view of an inserted incontinence treatment device according to an embodiment of the invention;

FIG. 21 shows an alternative staple, according to an embodiment of the invention;

FIG. 22 is a cross-sectional view of an incontinence treatment device according to an alternative embodiment;

FIG. 25 shows a staple ring retainer/release mechanism according to an embodiment of the invention;

FIG. 26 shows a mounting device, according to an embodiment of the invention;

FIG. 29 is a side view of an incontinence treatment device according to an alternative embodiment of the invention;

FIG. 30 is a perspective view of the FIG. 29 device;

FIG. 36 is a partial exploded view of a staple insertion/actuator mechanism, according to an embodiment of the invention;

FIG. 37 is a perspective view showing an incontinence treatment device with relatively extended staple ring engaging tips, according to an embodiment of the invention;

FIG. 48 shows an incontinence treatment device according to an embodiment of the invention;

FIG. 49 shows a viewing device useable with the FIG. 48 embodiment;

FIG. 50 is an end view of a staple useable with incontinence treatment devices and methods according to embodiments of the invention;

FIG. 59 is a side view of an apparatus for treatment of e.g. gastrointestinal hemorrhage, according to an embodiment of the invention, with a guide portion of the apparatus illustrated in cross-section;

FIG. 60 is a side view of the FIG. 59 apparatus in an alternative configuration;

DETAILED DESCRIPTION OF PREFERRED EMBODIMENTS

Embodiments of the invention relate to deployment devices and methods for deploying surgical stabilizers, e.g. surgical staples or similar stabilizing or fastening agents. Particular, first-described embodiments of the invention relate to devices and methods for treating incontinence, primarily urinary stress incontinence (USI). Although many if not most known surgical procedures and devices for treating USI are intended for the female population, embodiments of the invention are applicable equally to both females and males. Therefore, references in this application to female anatomy or treatment should be interpreted as applying equally to males, as well. Further, although embodiments of the invention are particularly well-suited for minimally invasive surgery, conventional surgical techniques also can be used, and this application should be interpreted accordingly. Other types of incontinence, e.g. surgically induced incontinence, also can be treated in certain circumstances. As will become clear, embodiments of the invention treat USI in a relatively uncomplicated, minimally invasive, and cost-effective manner not believed known or contemplated by the prior art.

Figure 2:
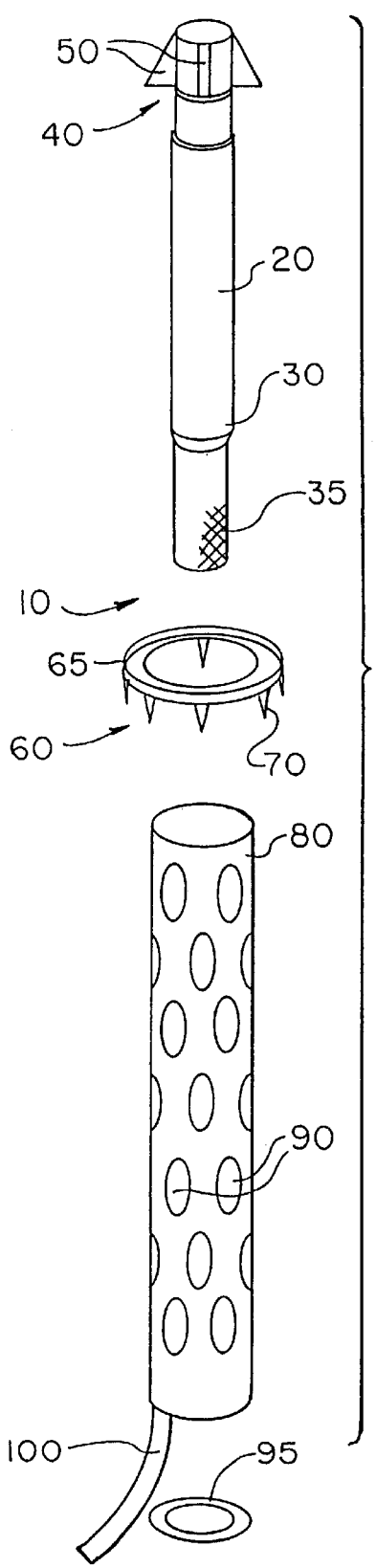
FIG. 2 is an exploded perspective view of an incontinence treatment device according to an embodiment of the invention.

FIG. 2 shows an exploded view of incontinence treatment device 10 according to an embodiment of the invention. Device 10 includes staple holder 20, having elongated shaft 30 terminating in handle 35. At the end of shaft 30 opposite handle 35 is staple mount 40 with retractable, tapered support portions or wings 50. Staple 60, having an annulus 65 with descending teeth or needles 70 as will be described, is secured to staple mount 40 during initial placement of device 10. Staple 60, as with all the staples described and/or illustrated in this application, preferably is formed of a biocompatible material.

Figure 3:
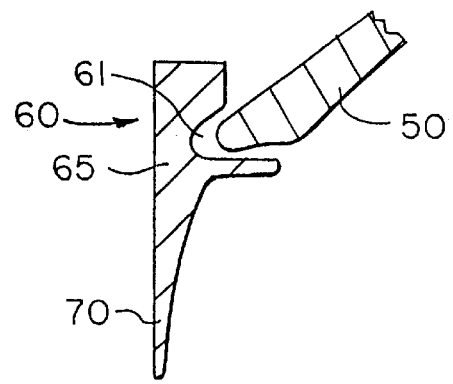
Figure 4:
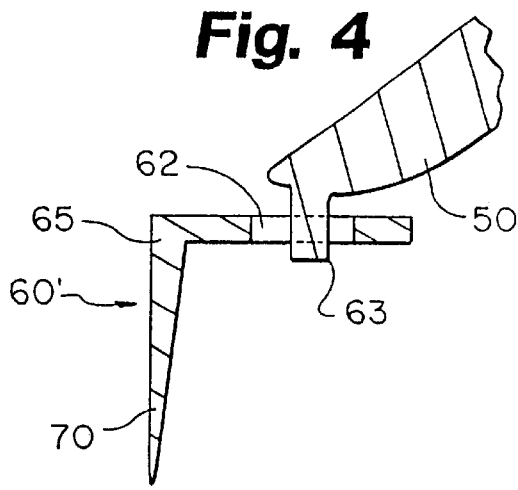
Figure 5:
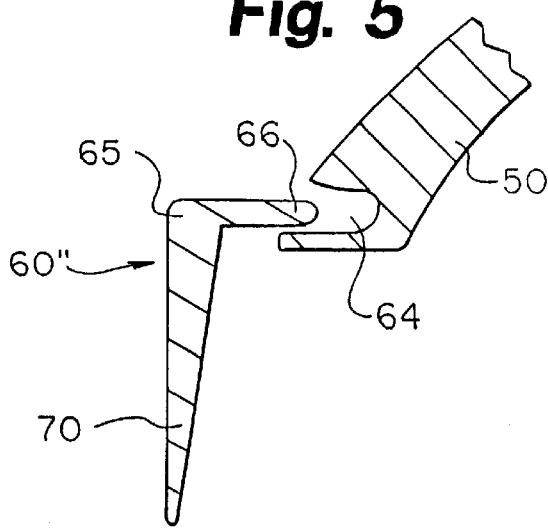

According to embodiments of the invention, the outermost portions of retractable wings 50 each include a protrusion, such as a pin, extending therefrom. FIGS. 3–4 illustrate two of these embodiments. In FIG. 3, staple 60 is provided with a substantially U-shaped groove 61 extending around the interior circumference of annulus 65. Of course, substantially V-shaped or other-shaped grooves are also contemplated, as is a groove extending around the exterior circumference of annulus 65. Multiple grooves in a single staple are also contemplated, with correspondingly shaped engaging wing structure. In FIG. 4, staple 60' is provided with a plurality of downwardly directed holes 62 through annulus 65, for example, through which corresponding downwardly directed pins 63 extend. Radially extending pins and holes are also contemplated. When wings 50 are in an extended position, the ends or pins of the wings engage the groove or holes of annulus 65 to secure staple 60 on staple mount 40. Other mating configurations are contemplated as well. In FIG. 5, for example, each wing 50 has groove 64 extending therethrough to accommodate corresponding portions 66 of staple 60", which portions can be raised or ridged.

Wings 50 preferably are spring-biased to an extended position, according to embodiments of the invention, for engaging and holding staple 60. Wings 50 can be retracted by a screw mechanism, extending through staple holder 20 and emerging near handle 35 for manipulation by the surgeon. Alternatively, wings 40 can be extended and retracted by telescoping and clasping mechanism 68, similar to that found on conventional umbrellas, as shown, for example, in FIG. 6. Although FIG. 6 shows the mating configuration of FIG. 5, use with alternative mating configurations is also contemplated.

Returning to FIG. 2, device 10 also includes vacuum support 80, having a plurality of suction apertures 90. Vacuum support 80 is substantially hollow and is constructed to receive and accommodate staple holder 20. At the lower end of vacuum support 80, O-ring vacuum seal 95 provides a fluid-tight seal and allows handle 35 of holder 20 to extend therethrough. Vacuum port 100 is provided to draw a vacuum through support 80 and suction apertures 90.

FIGS. 7–8 show device 10 in a substantially assembled condition. FIG. 7 shows cover 120, for shielding and preventing contamination of e.g. staple holder 20 and vacuum support 80 during insertion into the patient, and maintaining these and other elements in a sterile environment. Cover 120 also acts as a safety cover during insertion, to prevent injury to the patient due to staple 60 or other portions of device 10. Cover 120 is simply removed from the remainder of device 10, putting device 10 in a "ready" condition, by pulling it off over the mechanisms, etc. at the lower end of device 10.

FIG. 8 is substantially similar to FIG. 7 but eliminates cover 120 and shows additional features in the ready condition. Attached to and extending into staple holder 20 is pressure port 130, for a purpose to be described. Further, endoscope port 140 extends into staple holder 20 for accommodating an endoscope to view the interior of the urethra or bladder. Staple holder 20 is positioned substantially concentrically within vacuum support 80. Staple holder 20 includes retainer mechanism 141 with outwardly biased retaining legs 142 having staple-engaging portions 143. After implantation of staple 60 in a manner to be described, retaining legs 142 are urged inwardly, by e.g. an outer tube, a position out of contact with staple 60, such that staple holder 20 and associated elements can be removed.

Balloon or blocking member 150 is housed within staple holder 20 of device 10. Balloon 150 is operably connected to pressure port 130, and according to one example is one-piece with it. As balloon 150 is inflated via pressure port 130, balloon 150 moves from its housed position to the deployed position shown in FIG. 9. Flexible guide 153, made of e.g. plastic, folds out during balloon deployment and substantially prevents balloon 150 from going under staple 60.

As best shown in FIG. 10, balloon 150 also can be in a one-piece configuration with endoscope port 140. Balloon 150 is substantially transparent, according to this embodiment. Endoscope 155 is inserted through port 140 for viewing e.g. the bladder through balloon 150. Direct visualization can help the surgeon ensure proper positioning and engagement of balloon 150 with the bladder walls, as described below.

A method of use according to one embodiment of the invention will now be described, beginning with FIGS. 11–12. First, device 10 is inserted into urethra 160 of the patient to bladder 170. When fully inserted, as shown in FIG. 11, staple holder 40 and staple 60 have passed substantially all the way through bladder neck 175, as shown. The other end of device 10 extends substantially beyond urethral opening 180 for manipulation by the surgeon, as do vacuum port 110, pressure port 130, endoscope port 140, and the screw or other actuation mechanism for retractable wings 50.

Once inserted, pressure is applied through pressure port 130 to inflate balloon 150, causing it to extend from its housed position to the deployed position shown in e.g. FIG. 11. Balloon 150 is ultimately used to create a seal between bladder 170 and urethra 160, substantially preventing urine from passing out of bladder 170.

Once balloon 150 is inflated, a vacuum is pulled through vacuum port 110 and apertures 90 of vacuum support 80. The created vacuum condition in urethra 160 pulls balloon 150 toward urethra 160 to effect the above-described seal and pulls the sides of urethra 160 into a substantially tight relationship against vacuum support 80. According to one embodiment, apertures 90 of vacuum support 80 are large enough to sustain a vacuum in urethra 160, but small enough that significant portions of the walls of urethra 160 are not drawn into support 80. Endoscope 145 can be used to ensure that a proper seal has occurred between the balloon and the walls of bladder 170.

According to an alternative embodiment, balloon 150 and its associated apparatus is not used. Bladder 170 is allowed to collapse during application of the vacuum; the effect of the vacuum on the bladder neck and/or urethra is similar to that which occurs when balloon 170 is used.

Figure 1:
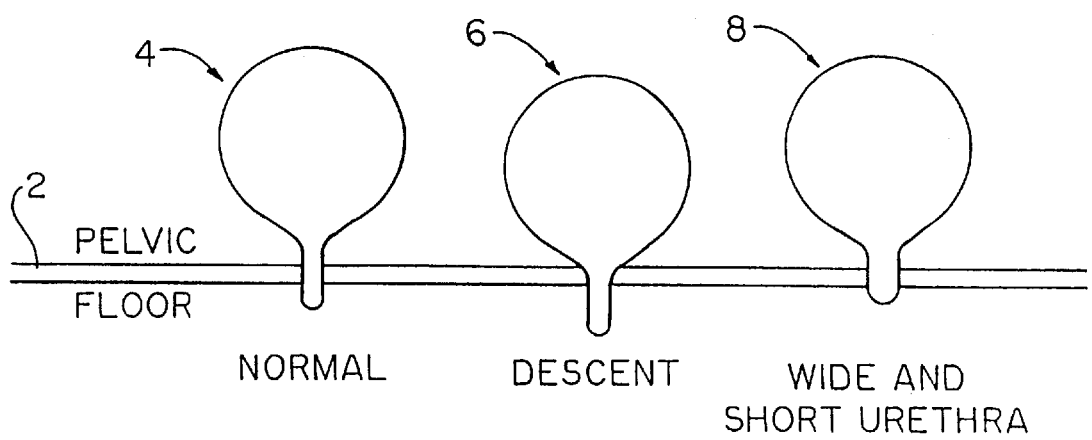
FIG. 1 illustrates three anatomical configurations of the bladder and urethra.

Drawing the vacuum through support 80 causes bladder neck 175 and the immediately adjacent portion of urethra 160 to assume a shape akin to the substantially normal anatomical shape shown in FIG. 1. To aid this process, the anterior wall of the vagina can be lifted, e.g. manually or with a trans-vaginal balloon, while the vacuum is applied. These maneuvers elevate urethra 160 and help narrow the urethral neck/bladder neck region 175. Once neck region 175 has assumed a desired shape, staple 60 is implanted in the neck region to maintain that shape, as described below. Of course, device 10 can be constructed to cause neck region 175 to assume any of a number of desired shapes, depending on e.g. the size of the patient, the surgical procedure or surgical environment, etc. For example, the size of the desired shape, the depth thereof, and other characteristics of the shape can be manipulated according to e.g. the surgeon's preference.

Device 10 is positioned such that needles 70 of staple 60 are adjacent neck region 175. To implant the staple, the surgeon then pulls handle 35 such that staple 60 moves towards the urethral opening. Traction on handle 35 pulls staple 60 into the interior tissue of neck 175, below the first layer of tissue, to hold neck 175 in the substantially normal shape caused by the vacuum.

Then, wings 50 are retracted inwardly and disengage and release staple 60. The vacuum applied through port 110 is released, and balloon 150 is deflated. Device 10 then is withdrawn from the urethra. Staple 60 is left behind to form a permanent, implanted support for neck 175.

Ultimately, as shown in FIG. 12, tissue 190 heals over and covers staple 60, making it "invisible" to interior regions of the bladder and urethra. These regions thus are free of foreign bodies, substantially reducing the likelihood of stones or lesions. Additionally, implantation of staple 60 in the manner described occurs substantially without killing the muscle, tissue or nerves of the urethra, all of which are important to normal urinary tract function.

According to preferred embodiments, annulus 65 of staple 60 is of low profile and forms a substantially complete circle. Staple 60 can also be elliptically shaped or formed in a partial-ring or arc shape. Staple 60 can include different numbers of needles 70, and these needles and/or staple 60 itself can be of various diameters, widths and thicknesses. The structural characteristics of staple 60 can be selected based on e.g. the anatomy of the patient, the anatomical location where the staple is placed, the degree of support desired, etc. According to preferred embodiments, staple 60 is comprised of inert metal, plastic or other biocompatible material suitable for implantation in the body and non-corrosive in urine and other fluids. It may also be elastic, to a degree, to allow for some expansion of the neck region 175 while still maintaining structural stability and support. Needles 70 can be formed of a memory metal to form a curve within the penetrated tissue, and to reduce the likelihood that staple 60 will work itself out over time.

Balloon 150 preferably is formed of an elastic, biocompatible material capable of sustaining relatively high pressures. Balloon 150 may be reinforced with internal or external ribbing to provide increased strength and/or support. Balloon 150 can include two dissimilar materials to aid in sealing the junction between bladder 170 and urethra 160. For example, balloon 150 can have a thicker top portion and a thinner bottom portion. As pressure within balloon 150 increases, the thinner bottom portion expands to a greater extent than the thicker top portion, aiding the sealing process. Similarly, the top portion of balloon 150 can have additional rib portions relative to the bottom portion to provide greater structural stability and again to encourage the bottom portion to seal off the bladder at the urethral opening.

FIG. 13 shows a more detailed view of the distal end of device 10.

Figure 14:
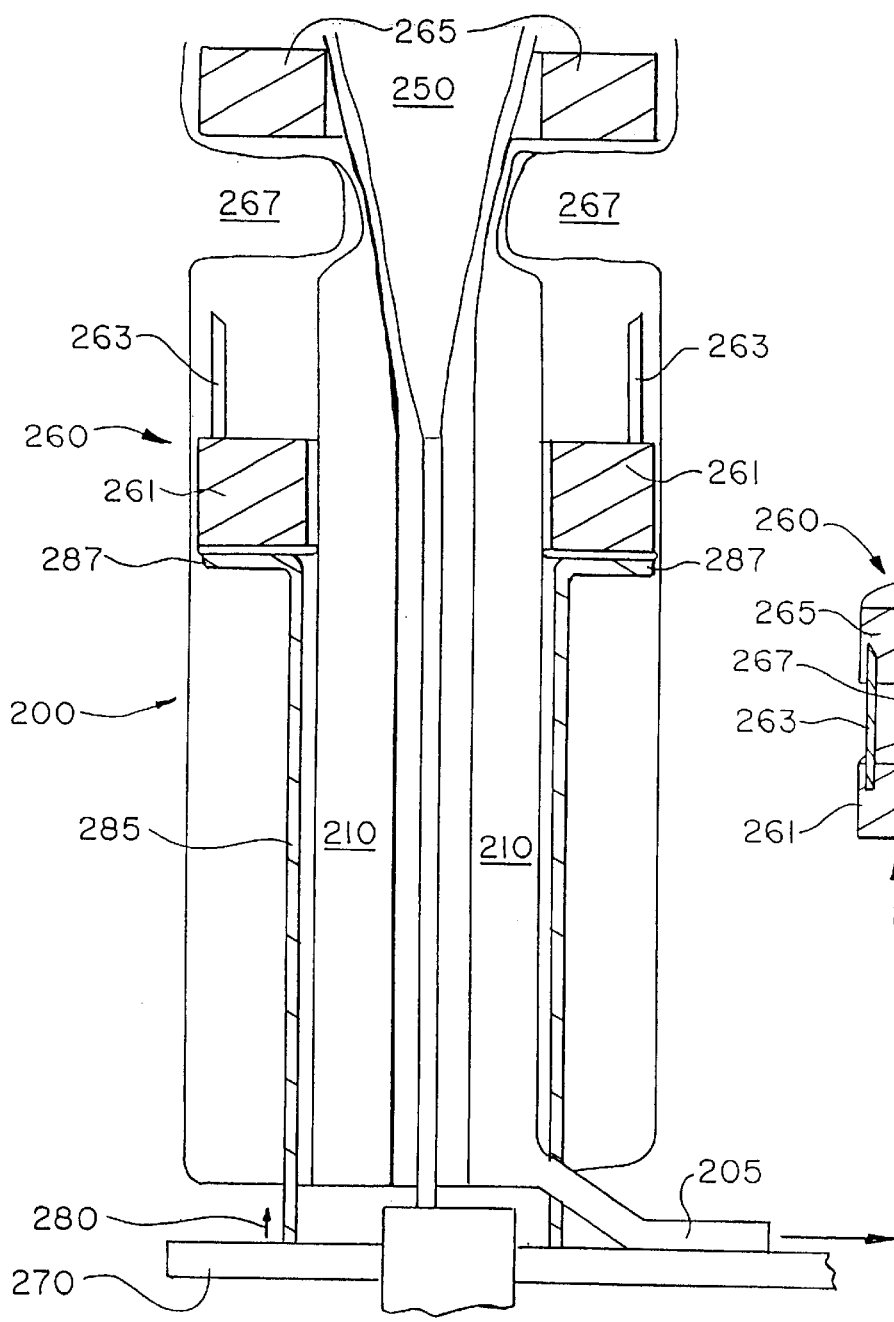
FIG. 14 shows an incontinence treatment device according to an alternative embodiment of the invention.
Figure 15:
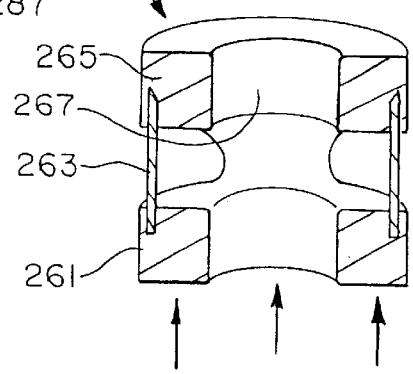
FIG. 15 is a detail view of the device shown in FIG. 14.

FIGS. 14–21 illustrate other staple embodiments and associated insertion devices according to embodiments of the invention. In FIG. 14, insertion device 200 includes vacuum port 205 for drawing a vacuum through interior vacuum chamber 210. Balloon 250, extending substantially down the center of device 200, is substantially similar to that described with respect to previous embodiments. Staple 260 preferably is of a different construction, however, and includes one or more base portions 261, needles 263, and one or more receiving portions 265. Note especially FIG. 15, showing a cross-section of staple 260 alone.

Inflating and deploying balloon 250 in the manner of previous embodiments, and then drawing a vacuum through vacuum chamber 210, causes portion 267 of the urethral wall, e.g. in the bladder neck region, to be drawn into the recess defined between base portion 261 and receiving portion 265. In this configuration, the bladder neck and surrounding area are restored to a substantially normal anatomical configuration, or at least to a configuration sufficient to prevent leakage when intra-abdominal pressure pulses occur.

Once the desired, vacuum-induced anatomical configuration is achieved, the surgeon applies pressure to handle 270 in the direction of arrow 280, causing push rod 285 to contact base portion 261 and urge needles 263 through tissue portion 267 and into receiving portion 265. Vacuum seal 287 is provided between push rod 285 and base portion 261. Back pressure against receiving portion 265 can be provided by a ledge or other member fixedly attached to structure surrounding balloon 250 (in its withdrawn position), in a manner akin to portions 143 in FIGS. 8–9 and 13.

A variety of structural features are contemplated to keep needles 263 retained within receiving member 265. Receiving member 265 can cause needles 263 to curve as they enter and penetrate, e.g. by including one or more internal, curved, substantially impenetrable portions. Needles 263 curve along the substantially impenetrable materials as they enter, much in the manner of a conventional paper stapler. Alternatively, or additionally, needles 263 can be formed of a memory-type metal, the memory causing the needles to curve so as to prevent removal from receiving member 265.

Once needles 263 have been secured in receiving member 265, the vacuum is released, balloon 250 is deflated, and device 200 is withdrawn from the urethra. Staple 260 remains, holding the bladder neck (or other anatomical region) in the desired configuration. Other features of these embodiments are substantially as shown and described with respect to previous embodiments. For example, staple 260 can be ring-shaped, elliptical, arc-shaped, of different dimensions, etc., and, as described with respect to FIGS. 48–56, below, generally coil-, spiral- or helix-shaped.

Figure 16:
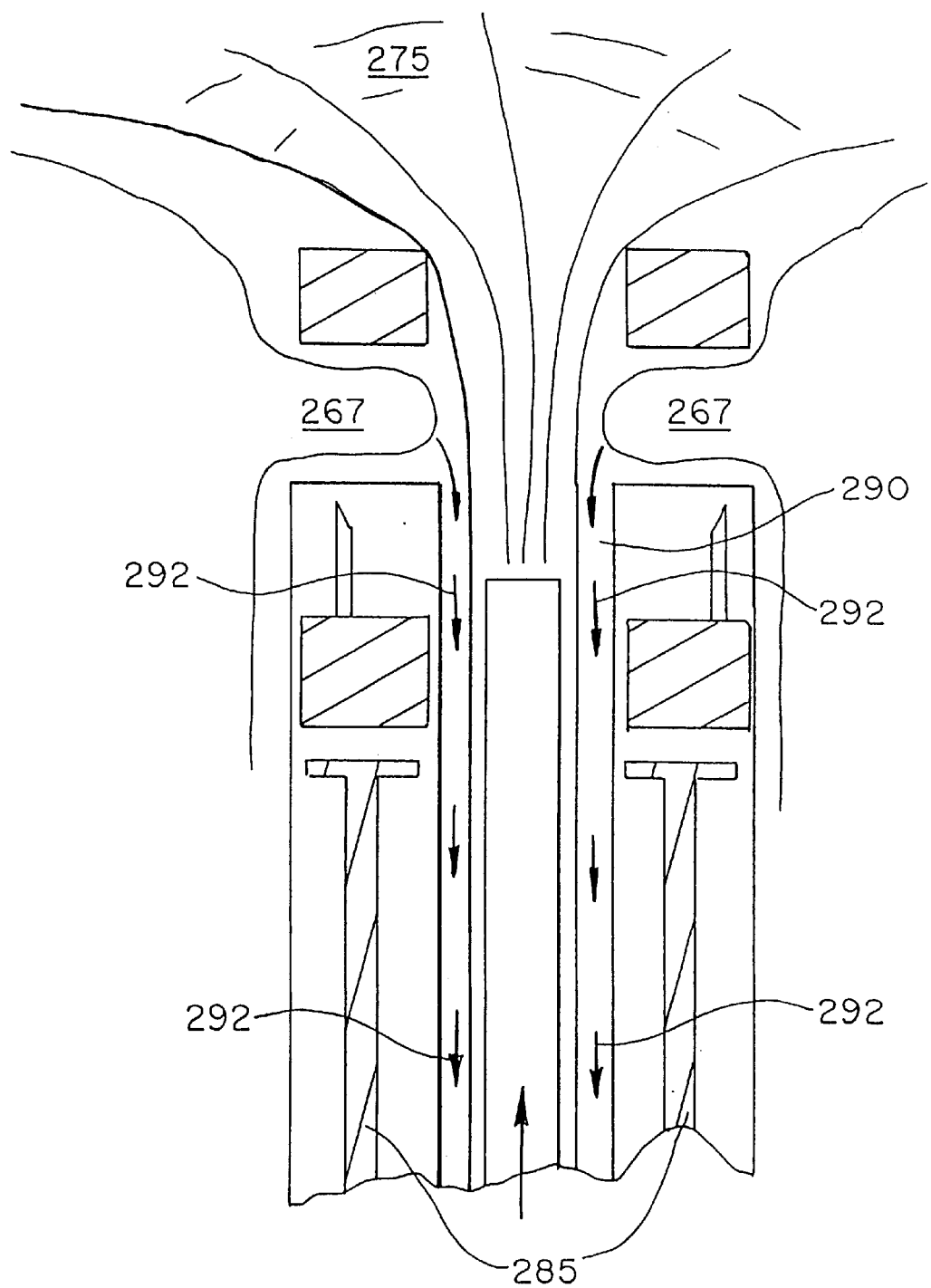
FIG. 16 shows an incontinence treatment device with indrawn tissue, according to an embodiment of the invention.
Figure 17:
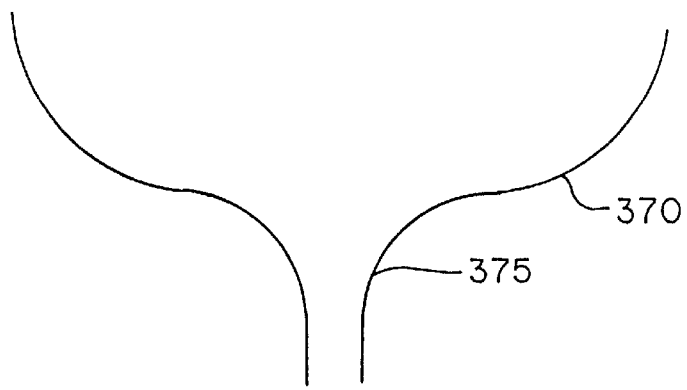
FIGS. 17–20 show an incontinence treatment device as it is inserted into a sagging bladder/urethra, according to embodiments of the invention.
Figure 18:
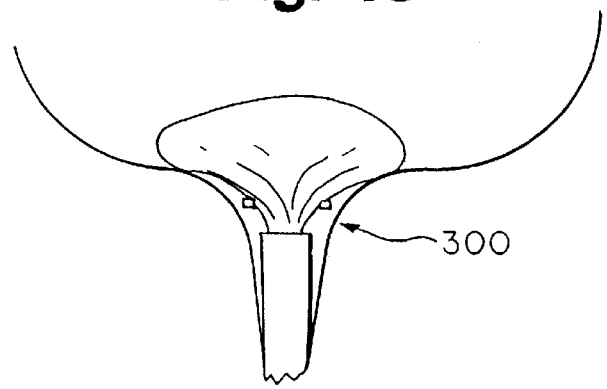
Figure 19:
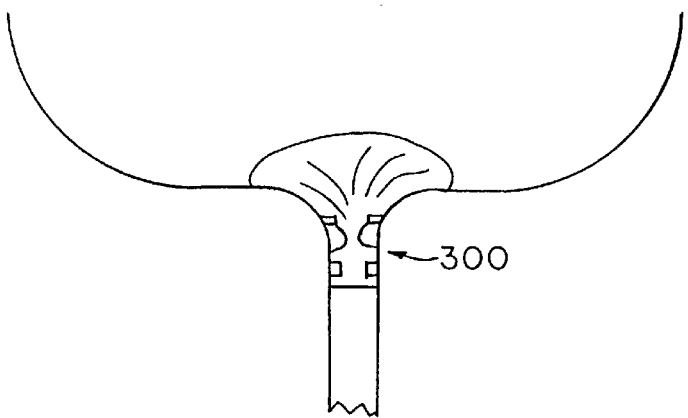
Figure 20:
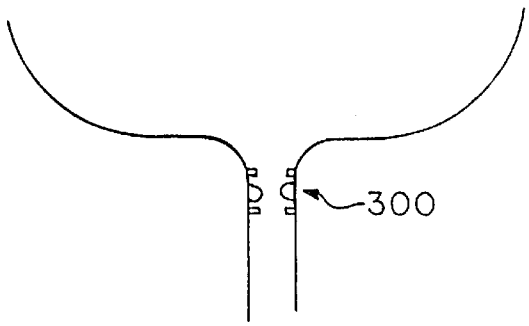

The FIG. 16 embodiment is somewhat similar to the embodiment of FIG. 14, but a preferably lightweight, strong retractable plastic portion 275 in the form of an inverted umbrella is used to provide the vacuum seal between the bladder and the urethra. Also shown in FIG. 16 is a central open lumen 290 for an endoscope to be inserted through the center of the device, for visually confirming that the plastic portion is positioned properly to form the desired seal. Lumen 290 is for pulling a vacuum in the direction of arrows 292, in the manner described earlier. Tissue and muscle 267 are drawn inwardly by the vacuum, as shown.

FIGS. 17–20 generally show the anatomical correction achievable according to embodiments of the invention. As shown, sagging bladder 370 and neck region 375 of FIG. 17 receive insertion device 300 in FIG. 18. Vacuum is applied and a more normal anatomical configuration is induced in FIG. 19, as described previously. Finally, the staple is closed, as in FIG. 20, to maintain the desired anatomical configuration achieved by vacuum.

FIG. 21 shows an additional staple embodiment. Staple 360 includes needles 363, of greater relative length than the needles of previous embodiments, for penetration through a relatively large tissue region 367 between annular staple supports 361, 365. This arrangement supports a greater length of the urethra while still allowing the sphincter to act naturally, as with previous embodiments. Other features of this embodiment are substantially as described with previous embodiments.

FIGS. 22–28 show cross-sections of a preferred embodiment of the invention that uses many of the apparatus and method principles described above. FIG. 22 is a cross-sectional view of device 400 in a substantially assembled condition, and FIGS. 23–28 show and highlight individual components of device 400.

Figure 23:
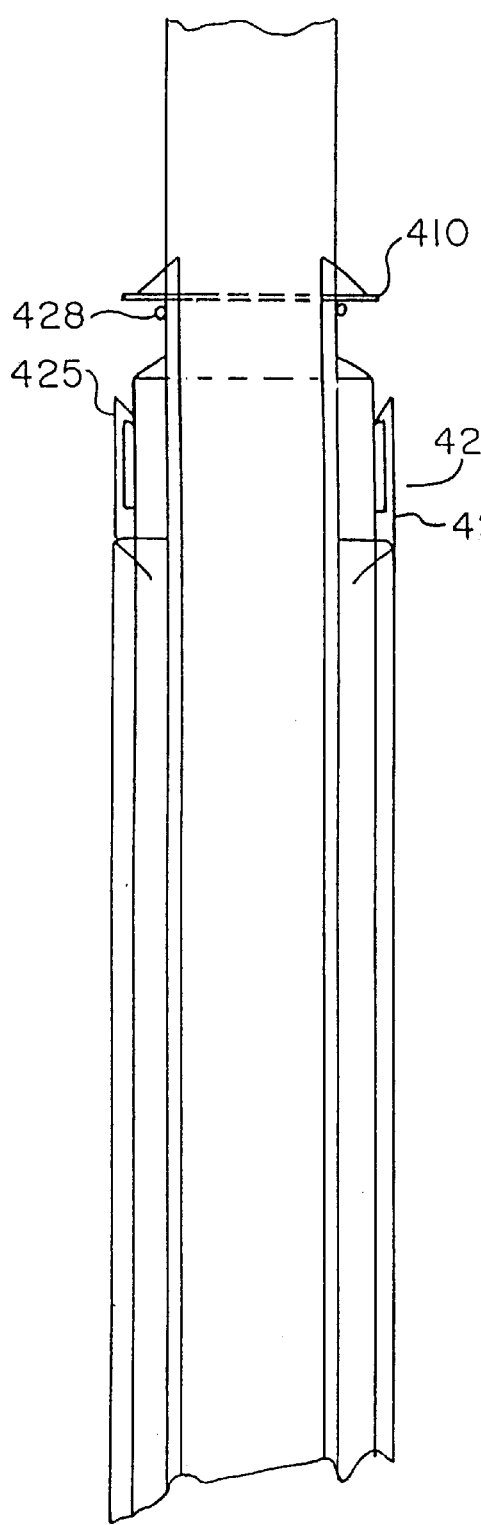
FIG. 23 is a cross-sectional view of a staple ring and a staple mounted on an insertion device, according to an embodiment of the invention.

Device 400 implants a two-part stapling mechanism comprising locking member or staple ring 410 and staple 420, shown in e.g. FIG. 23. Depending needles 423 of staple 420 each preferably include a tapered-surface tip or barb 425 for engaging behind and clipping over staple ring 410. According to one embodiment, needles 423 are substantially flexible with respect to the base portion of staple 420 and snap into locking engagement with staple ring 410. This structure provides firm securement of the staple in the bladder neck. Further, device 400 causes staple 420 to slide along an inner supporting tube, as will be described, for better control and to avoid "rocking," i.e., insertion at an undesirable angle. Before implantation, staple ring 410 rests on bead 428.

Figure 24:
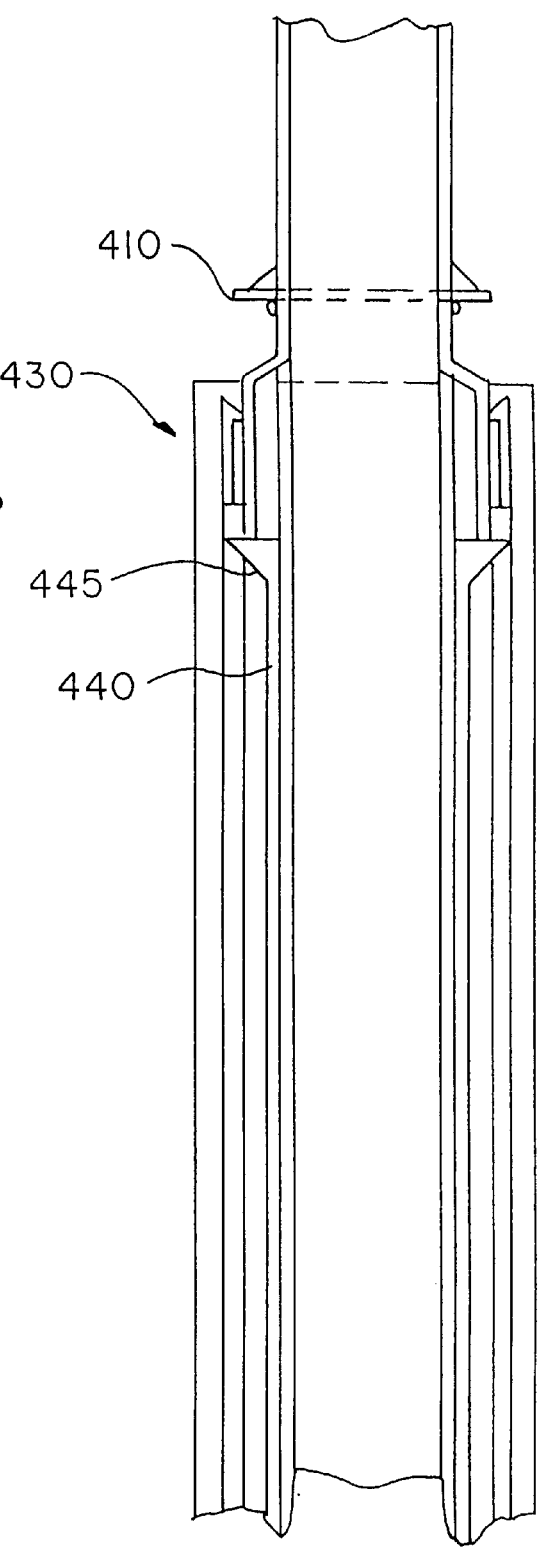
FIG. 24 is a cross-sectional view of a staple insertion/actuator mechanism, according to an embodiment of the invention.

FIG. 24 shows staple insertion/actuator mechanism 430, to which handle 435 (FIG. 22) is attached at its proximal end. Mechanism 430 includes leg member 440 and pedestal portion 445, on which staple 420 rests. When the surgeon or other medical professional moves handle 435 farther into the urethra, leg member 440 and pedestal 445 push staple 420 along an inner supporting tube towards staple ring 410. Eventually, barbs 425 pierce the pulled-in tissue, as described with respect to previous embodiments, and snap behind staple ring 410 for a secure engagement.

FIG. 25 illustrates staple ring retainer/release mechanism 450, attached to handle 455 (FIG. 22) at its proximal end. Mechanism 450 includes outwardly biased retaining legs 460 with staple ring engaging tips 470. Tips 470 include ramped portions 473, which extend outwardly through slots or other track structure in a surrounding tube, described with respect to e.g. FIG. 26, below. Once the stapling device is implanted, the medical professional urges release mechanism 450 farther into the urethra. This causes ramped portions 473 of tips 470 to ride within the tracks in the outer tube, which in turn urges retaining legs 460 inwardly. Once tips 470 are urged inwardly far enough to clear staple ring 410, and the balloon is deflated, the entire mechanism 450 can be withdrawn from the urethra through the center of staple ring 410.

FIG. 26 illustrates mounting device 480, secured at its proximal end to device support 485 (FIG. 22). Mounting device 480 includes tube 490 with recessed portion 495 for accommodating the pulled-in tissue. Device 480 also includes a distal wall portion with slots or tracks 475, through which ramped portions 473 of tips 470 protrude.

Figure 27:
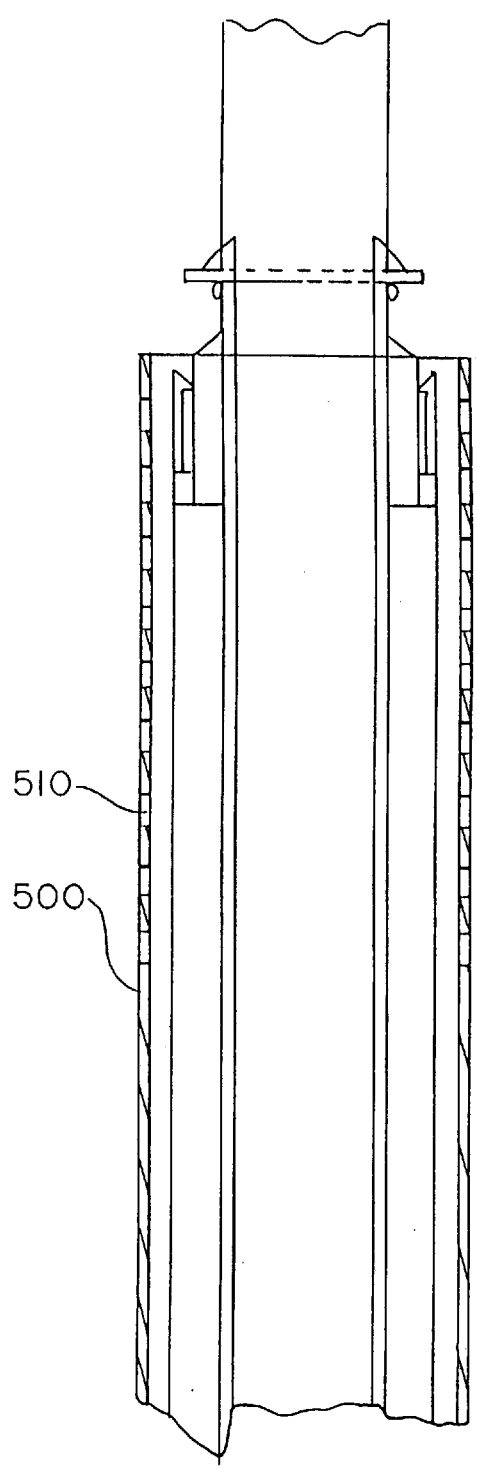
FIG. 27 shows a vacuum retainer mechanism, according to an embodiment of the invention.

FIG. 27 shows vacuum retainer mechanism 500, which defines suction apertures 510 for drawing a vacuum through vacuum port 515 (FIG. 22), substantially in the manner described earlier.

Figure 28:
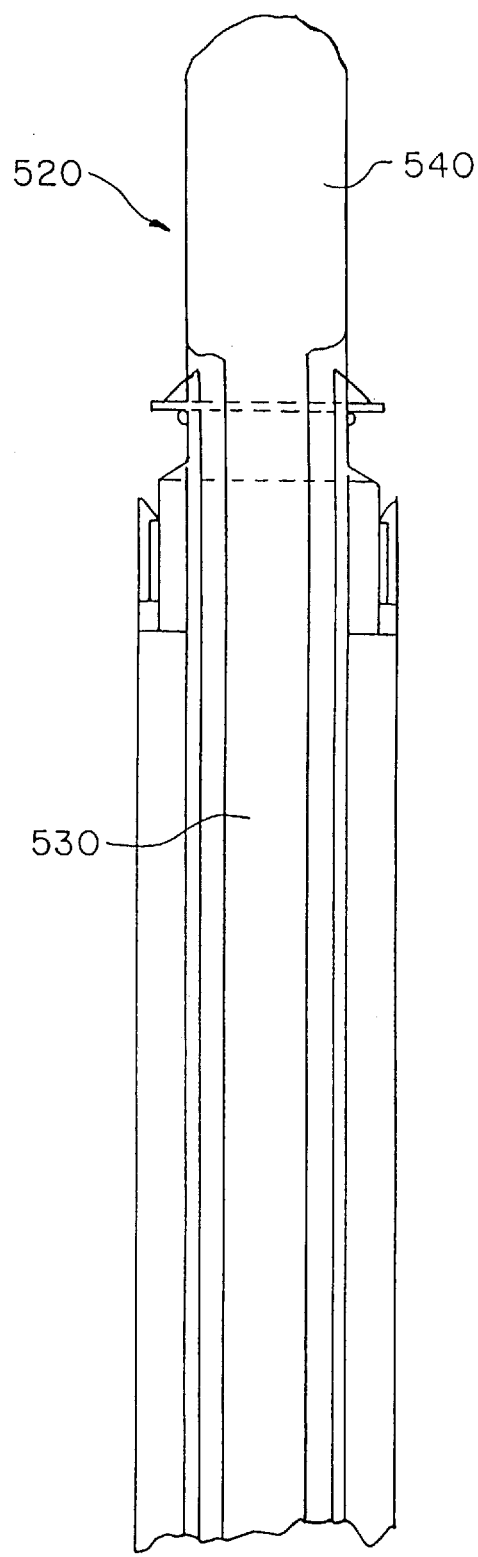
FIG. 28 shows a balloon and catheter assembly, according to an embodiment of the invention.

Finally, FIG. 28 shows balloon and catheter assembly 520. Catheter 530 preferably extends down the center of device 400, and is coupled with endoscope port 535 (FIG. 22) to accommodate an endoscope, as described earlier. Balloon 540 is illustrated in its undeployed position, and is coupled with pressure port 550 for inflation and deployment, in a manner substantially as described previously.

Device 400 optionally can be fit into a handle mechanism made of plastic or other suitable material. The handle preferably has slots to accommodate e.g. handle 435 of insertion/actuator mechanism 430, handle 455 of staple ring retainer mechanism 450, device support 550, etc. The handle can be disposable or constructed for reuse, as desired.

FIGS. 29–41 show handles and associated structure according to additional embodiments of the invention, incorporating many of the previously described features in a more refined form. Many of the concepts embodied in FIGS. 29–41 have already been described; to simplify the disclosure, many such concepts will not be repeated. For example, the various balloon/inflatable members described above will not be described again here.

As shown in FIGS. 29–30, the illustrated incontinence treatment device 600 includes base handle 605, which preferably is one-piece with or otherwise attached to substantially cylindrical, upwardly extending member 610. Member 610, in turn, preferably is one-piece with or otherwise attached to ring retainer 620. Ring retainer 620 defines recessed portion 630, for accommodating tissue and/or muscle pulled therein by a vacuum source in a manner described previously. Further details of retainer 620 are provided below.

FIGS. 29–30 also illustrate staple-release handle 650, disposed above base handle 605 in this embodiment. Staple-release handle 650 preferably is one-piece with or attached to substantially cylindrical, upwardly extending member 660 (not visible in FIGS. 29–30, but shown in e.g. FIGS. 36–37), which preferably surrounds member 610. Disposed above staple-release handle 650 is staple-advance handle 670, which is one-piece with or rigidly attached to substantially cylindrical, upwardly extending member 680. Member 680 preferably surrounds member 660. Finally, FIG. 29 illustrates base or support 485, which is one-piece with or rigidly attached to vacuum retainer mechanism 500. Mechanism 500 includes suction apertures 510 and has already been described.

Figure 31:
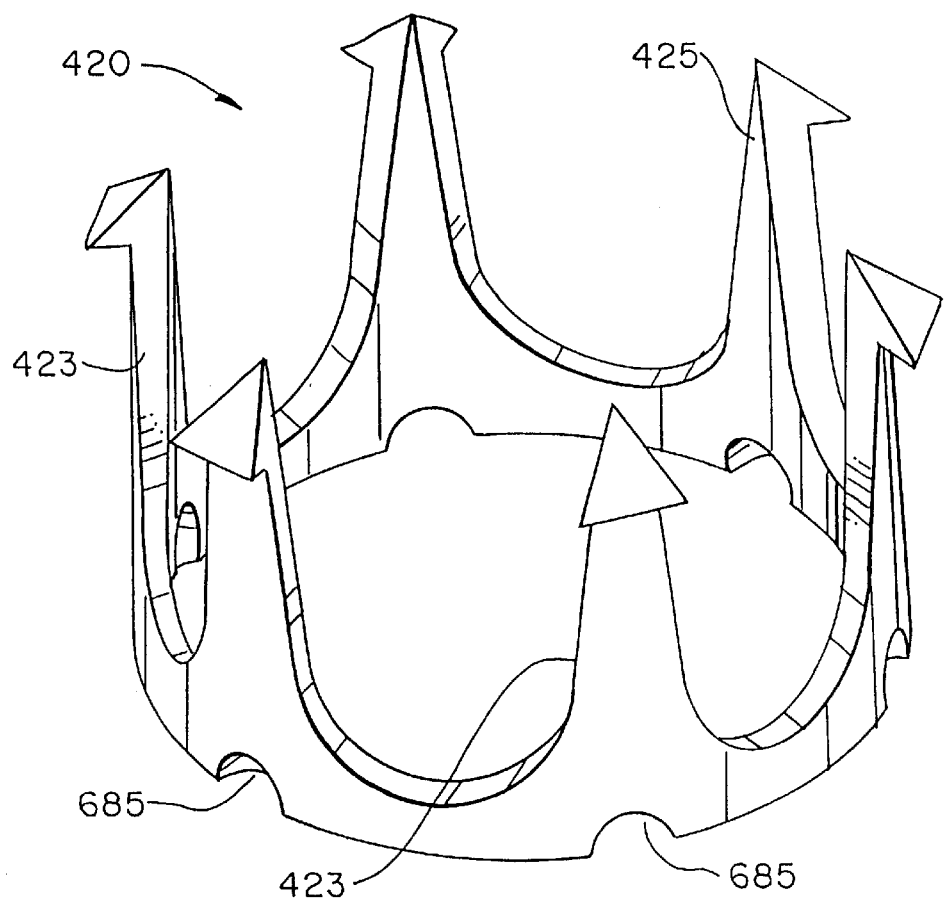
FIG. 31 is a perspective view of a staple, according to an embodiment of the invention.
Figure 31A:
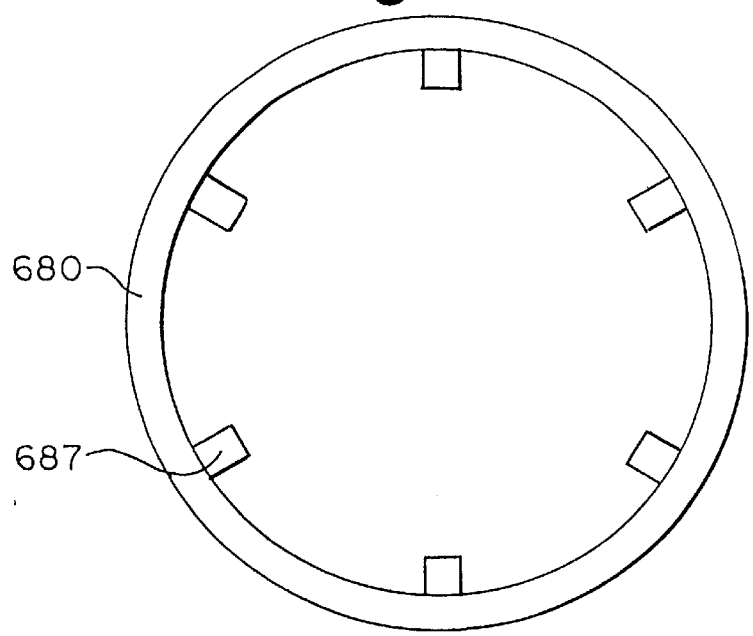
FIG. 31A is a top view of a support for the staple of FIG. 31.

FIG. 31 illustrates staple 420, which has been described previously. Also visible in FIG. 31 are detents 685. According to one embodiment, shown in FIG. 31A, upwardly extending member 6580 includes a plurality of radially inwardly extending pins 687. Pins 687 fit within detents 685 of staple 420, to provide support for staple 420 relative to member 680. Detents 685 also allow rotational indexing, so that staple 420 can be prealigned before a treatment procedure beings. Member 680 can be rotated, e.g. via handle 670 or otherwise, until needles 423 are properly aligned with respect to ring retainer 620, which will now be described in more detail.

Figure 32:
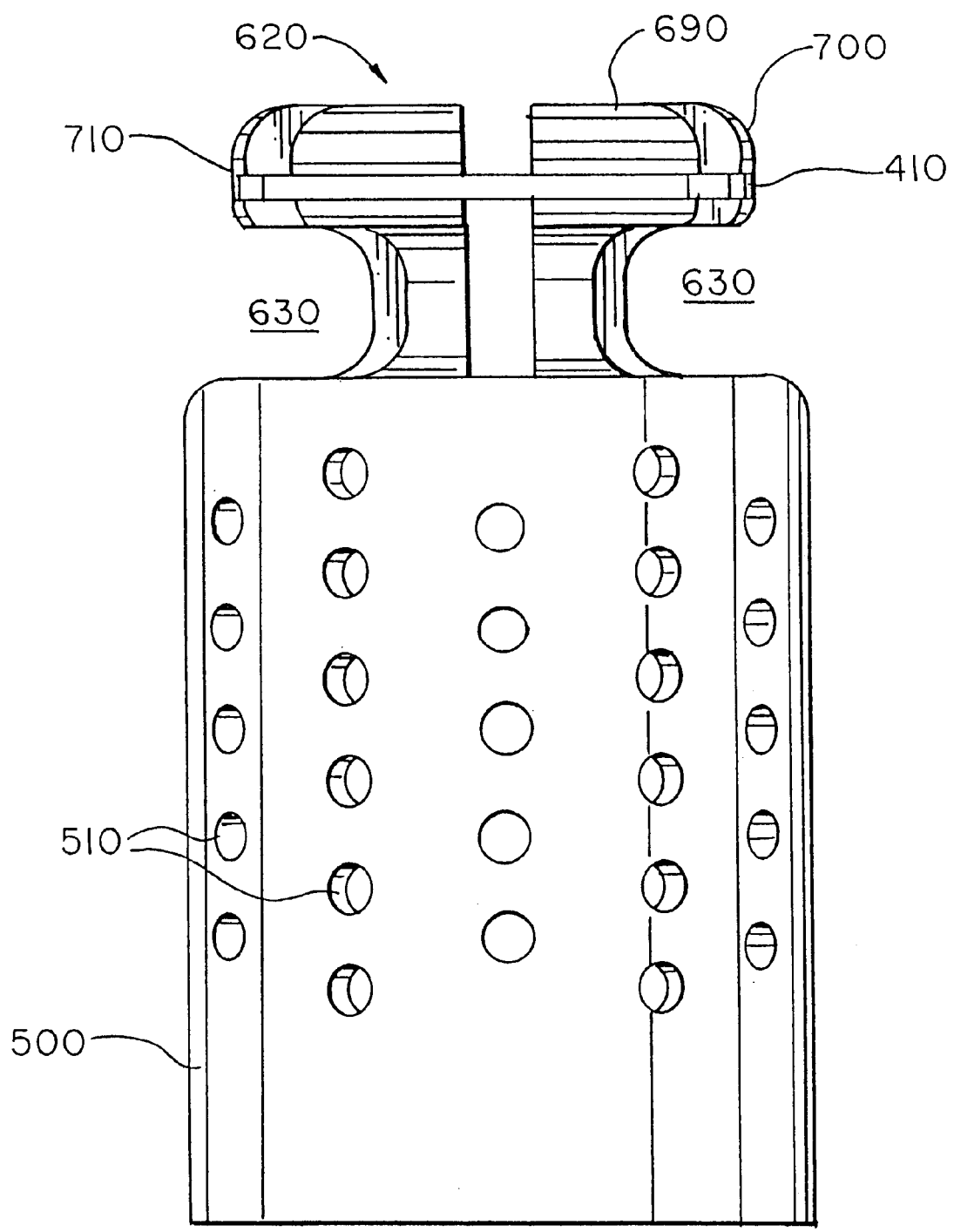
FIG. 32 is a side view of an upper portion of the FIG. 29 device.

As shown in FIG. 32, ring retainer 620 includes a plurality of sprung legs 690. The illustrated embodiment includes six such legs 690, but of course a greater or lesser number of legs, for example three legs, is also contemplated. Providing fewer legs tends to allow more room for the balloon or other structure disposed within device 600. Each leg 690 preferably includes one or more slanted surfaces 700, 720. Such surfaces preferably engage structure external to mechanism 620, to drive legs 690 inwardly after staple 420 has been brought through the tissue/muscle in gap 630 and into contact with staple ring 410. This contact occurs as the medical professional moves staple-release handle 650. Moving legs 690 inwardly withdraws legs 690 from staple ring 410 and removes legs 690 from supporting contact with staple ring 410 at groove 710, once it is desired to withdraw treatment device 600 from the bladder/urethra.

As best shown in FIG. 37, ring retainer 620 also defines recesses 730 at the uppermost portion of upwardly extending member, for accommodating depending needles 423 of staple 420. Recesses 730 preferably are disposed directly beneath gaps 740 between legs 690 of retainer 620, such that needles 423 slide from recesses 730, across gap 630 and into gaps 740. This configuration assures accurate and even positioning of needles 423 behind staple ring 410. As referenced previously, handle 670 can be turned to rotationally index staple 420 for correct positioning.

Figure 33:
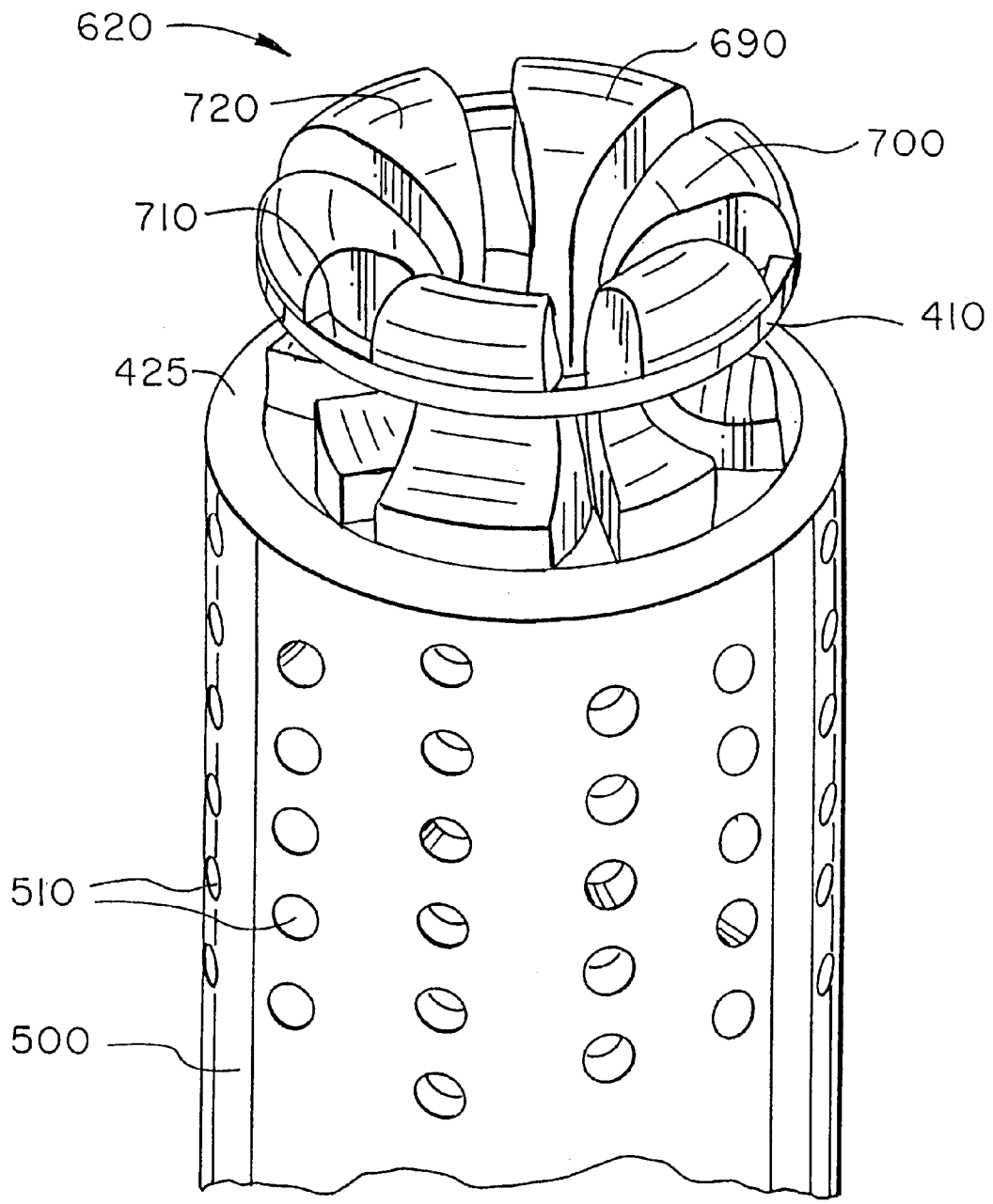
FIG. 33 is a perspective view of the FIG. 32 device.
Figure 34:
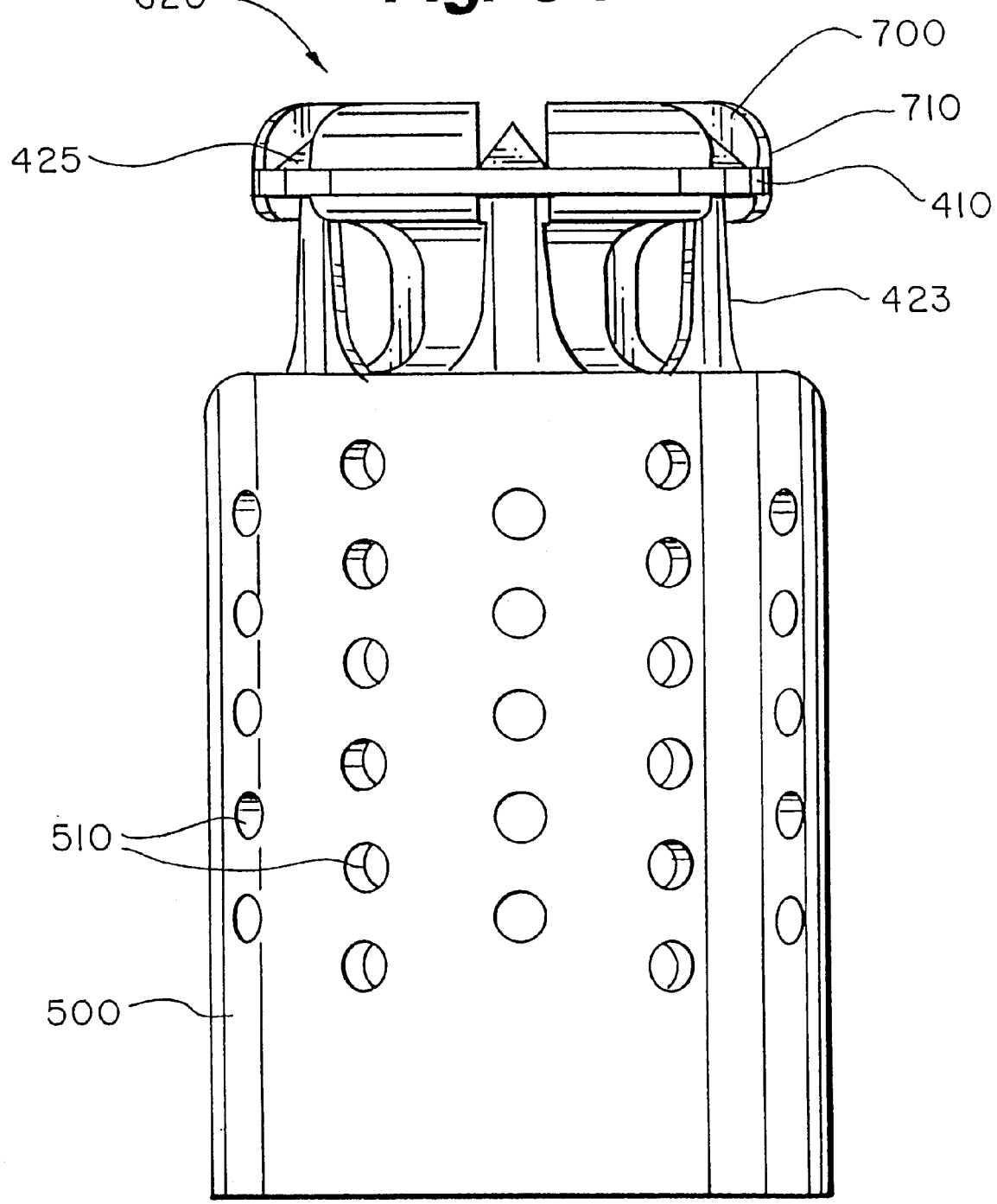
FIG. 34 is a side view similar to FIG. 32, but with portions of the staple disposed behind the staple ring, according to an embodiment of the invention.
Figure 35:
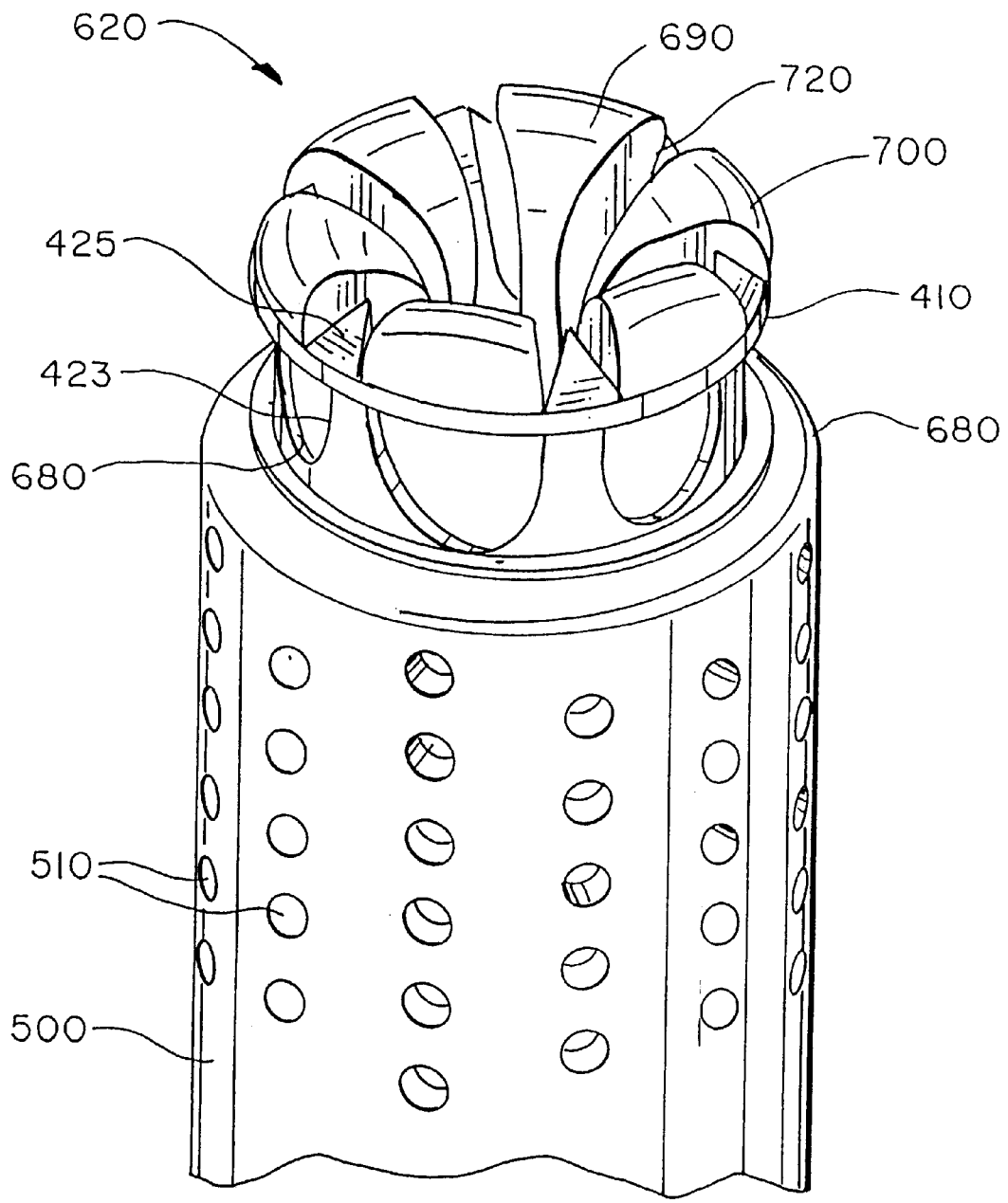
FIG. 35 is a perspective view of the FIG. 34 device.

In use, ring retainer 620 is first disposed as shown in FIGS. 32–33. The staple is mounted on pins 687 and rotationally aligned with respect to retainer 620. The device is inserted into the patient in the manner described previously. Vacuum is applied and the tissue/muscle is drawn into gap 630, also as described previously. Staple 420 then is urged across gap 630, by movement of staple-advance handle 670, through the tissue and into contact with staple ring 410. As shown, barbs 425 each include a tapered surface for engaging and sliding relative to ring 410, and depending needles 423 of staple 420 then lock into place behind ring 410. The configuration of FIGS. 34–35 thus is achieved.

Figure 38:
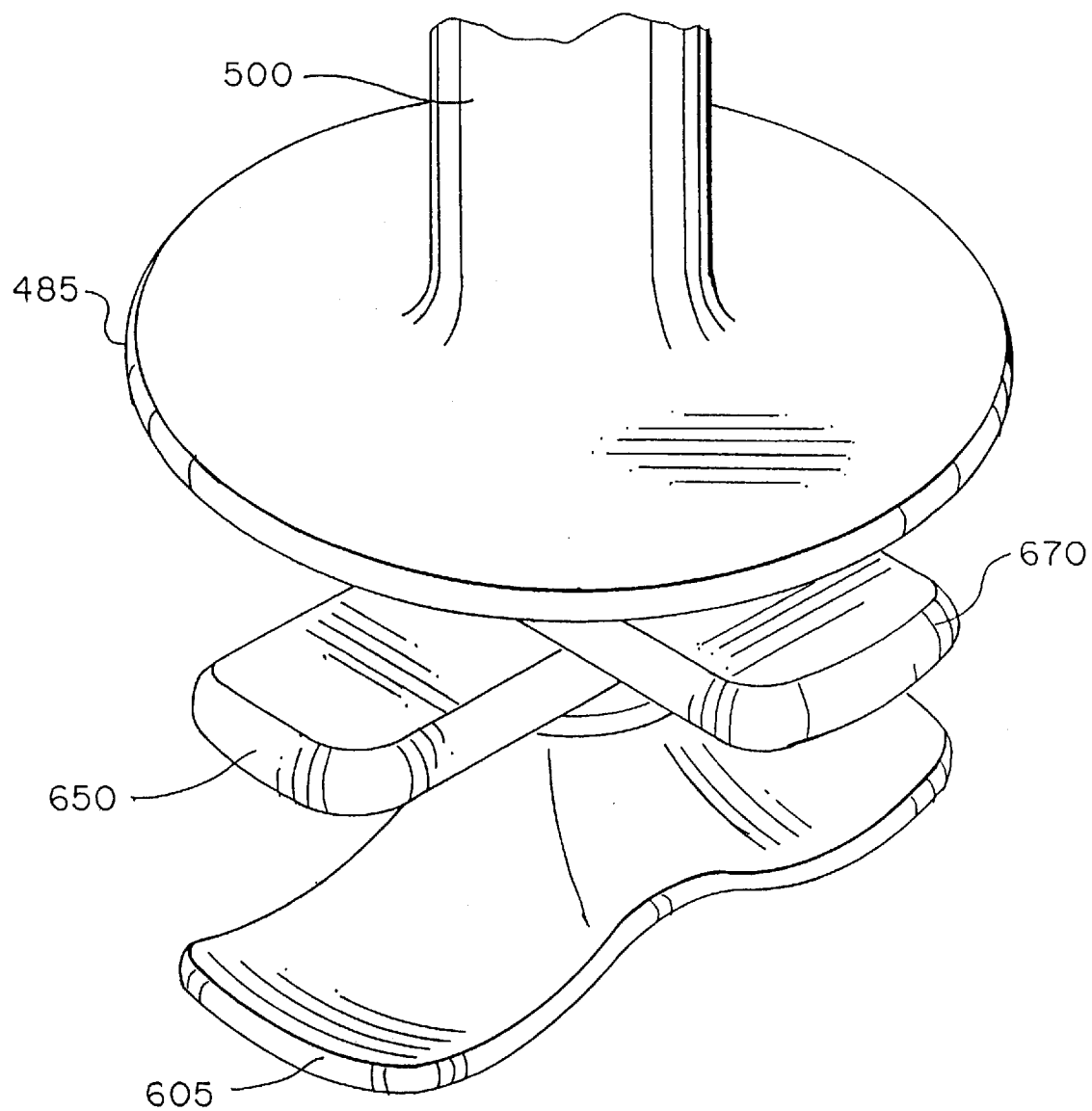
FIGS. 38–41 are lower perspective views of incontinence treatment devices, according to alternative embodiments of the invention.
Figure 39:
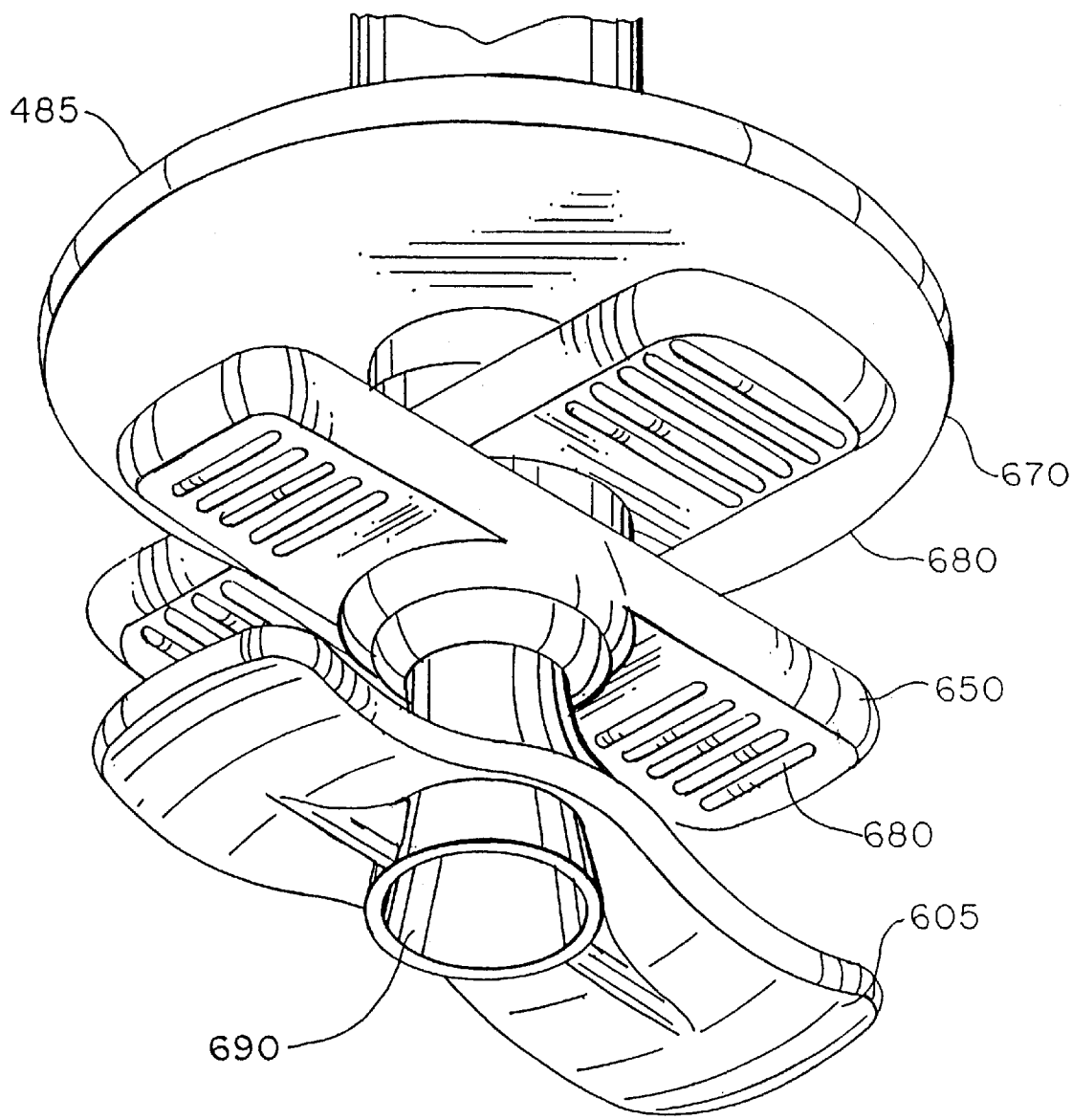

FIG. 38 shows a streamlined version of the lower end of device 600. FIG. 39 shows the undersides of handles 605, 650 and 670. Ridges 680 provide a better gripping surface for the surgeon or other medical professional. FIG. 39 also illustrates aperture 690, through which extend e.g. the catheter and endoscope described previously, along with other instruments that might be desirable for a particular procedure, such as a camera, electrocautery, endoscopic suture device, etc.

Figure 40:
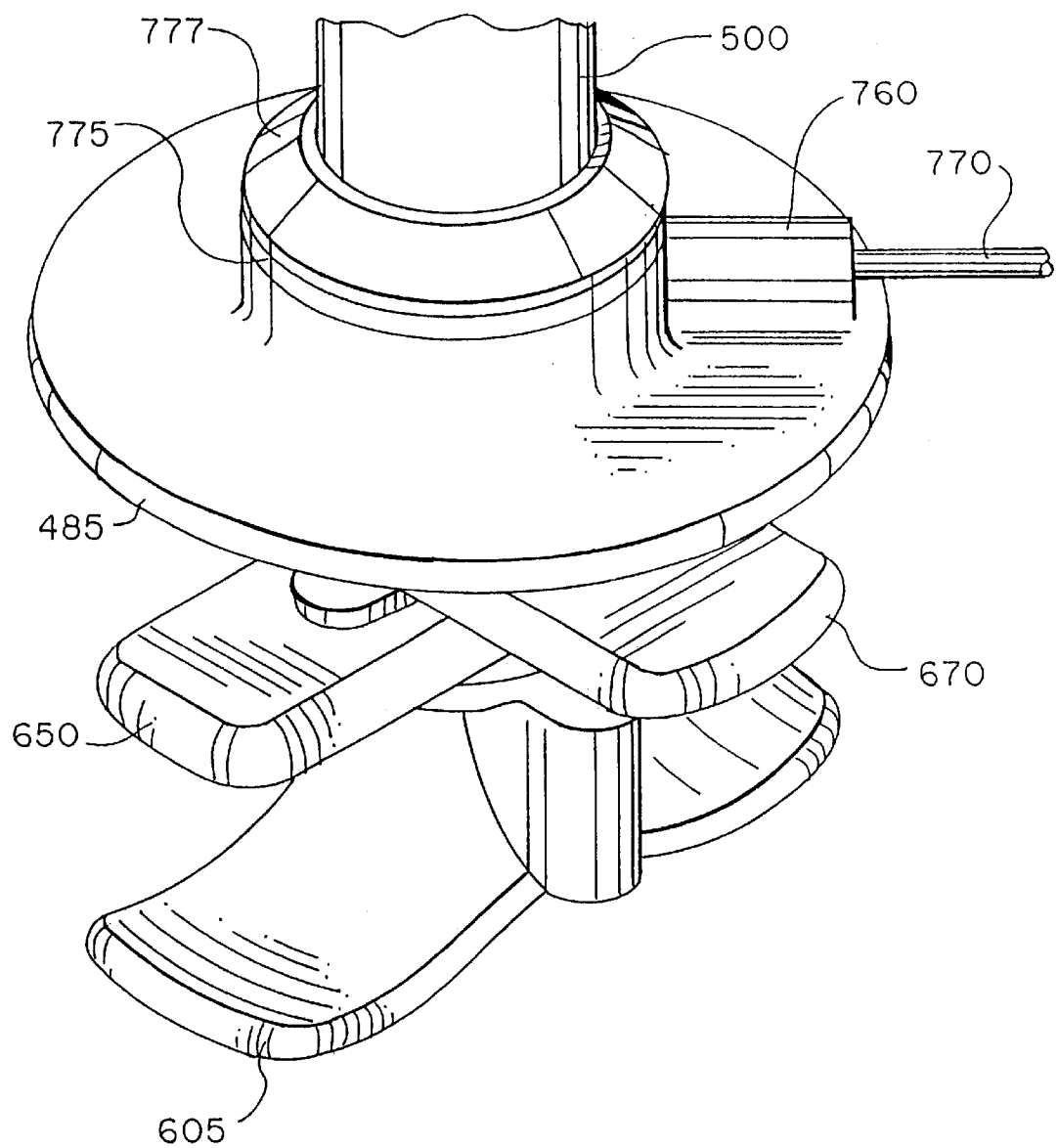
Figure 41:
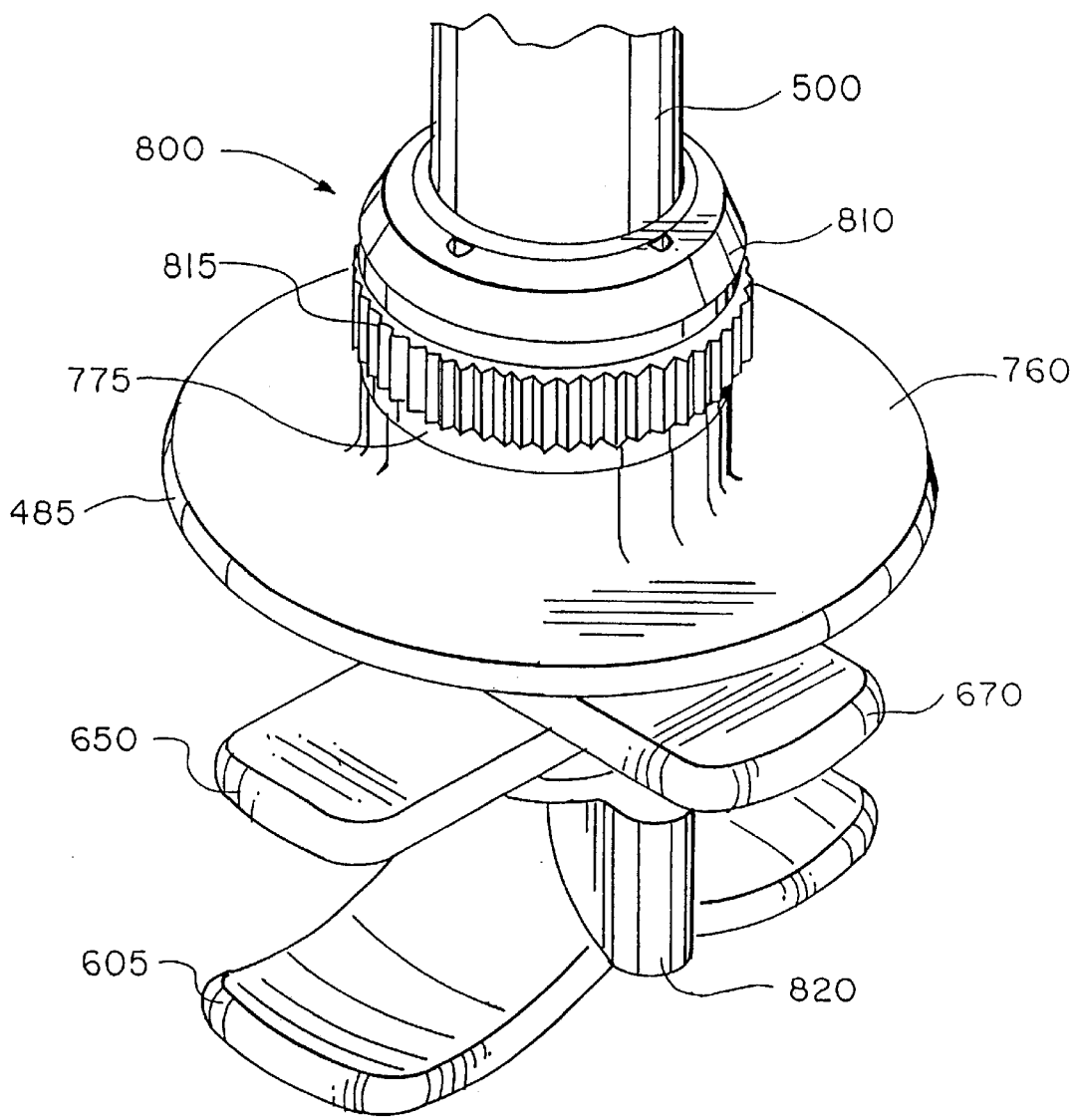
Figure 42:
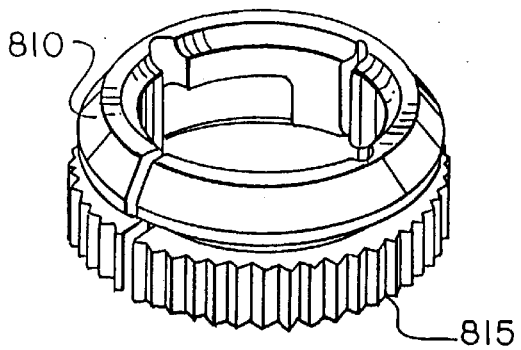
FIG. 42 is a top perspective view of a thumbwheel mechanism, according to an embodiment of the invention.
Figure 43:
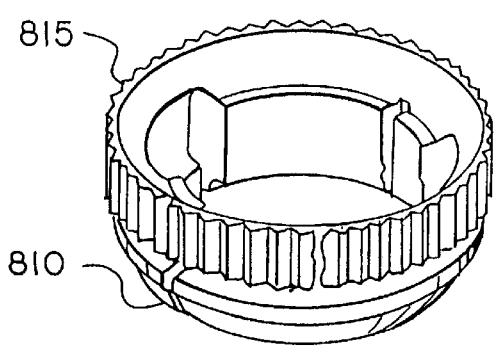
FIG. 43 is a bottom perspective view of the FIG. 42 thumbwheel.
Figure 44:
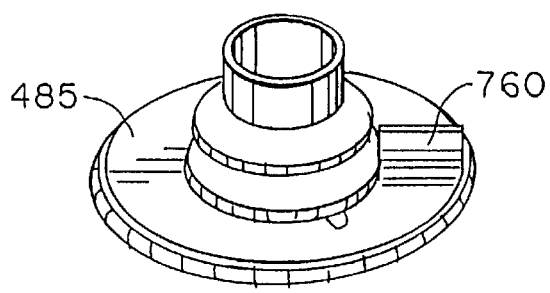
FIG. 44 is a top perspective view of a handle outer shell, according to an embodiment of the invention.
Figure 45:
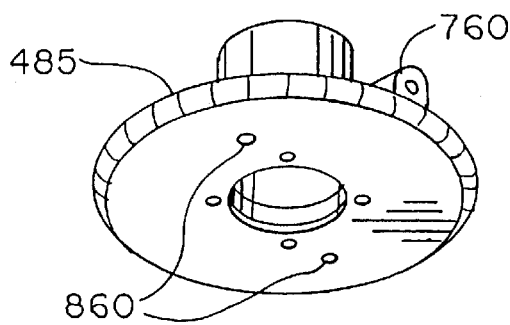
FIG. 45 is a top view of the FIG. 44 shell.
Figure 46:
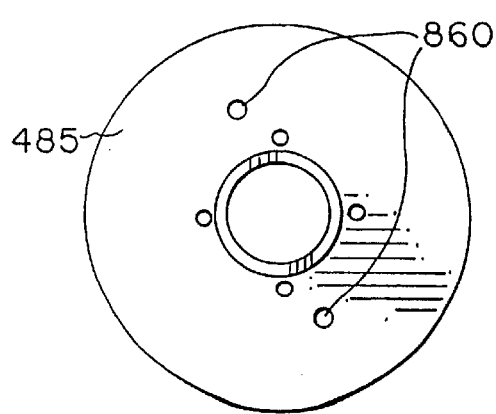
FIG. 46 is a bottom perspective view of the FIG. 44 shell.
Figure 47:
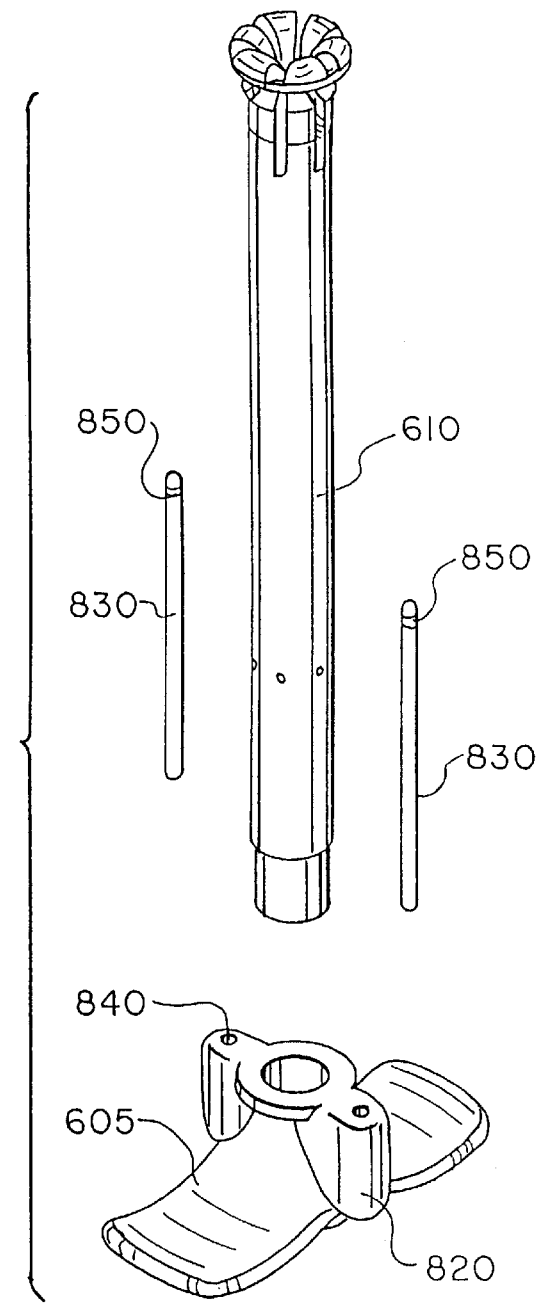
FIG. 47 is an exploded view showing a ring retainer assembly according to an embodiment of the invention.
Figure 51:
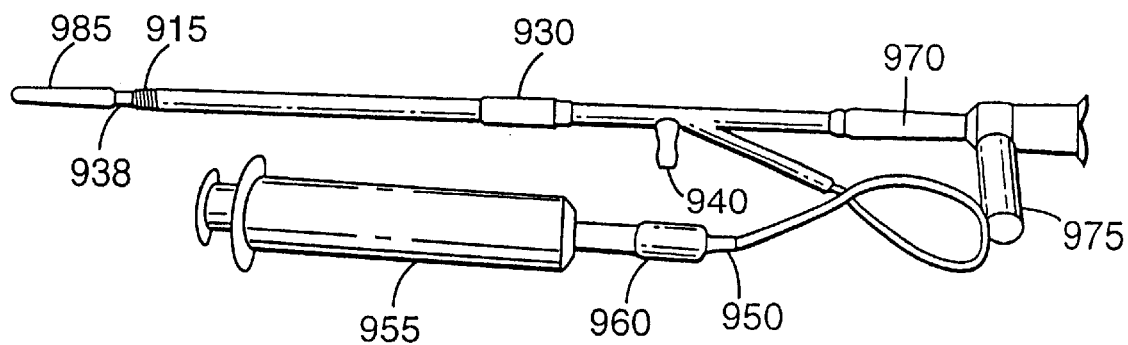
FIGS. 51–56 show an incontinence treatment device according to embodiments of the invention.
Figure 52:
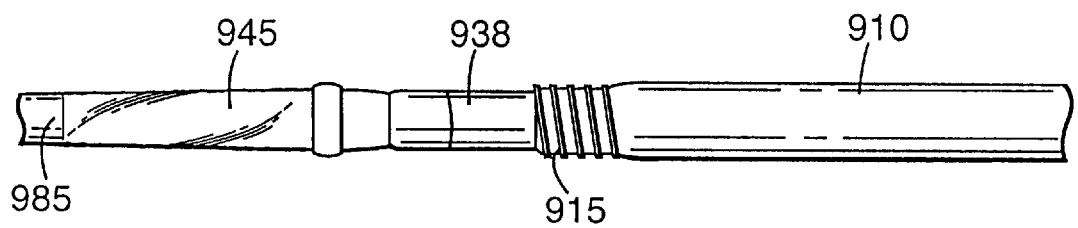
Figure 53:
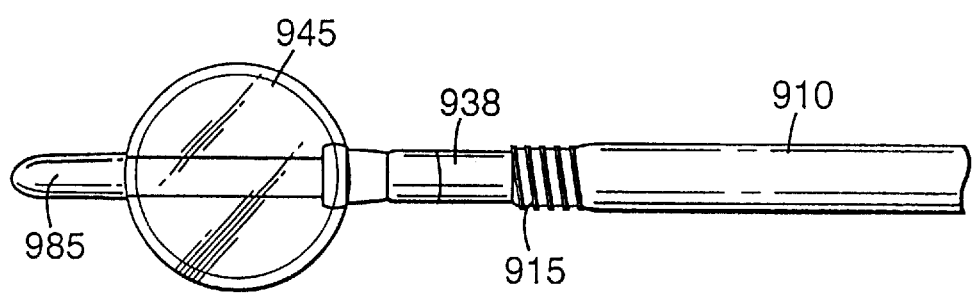
Figure 54:
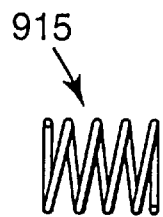
Figure 55:
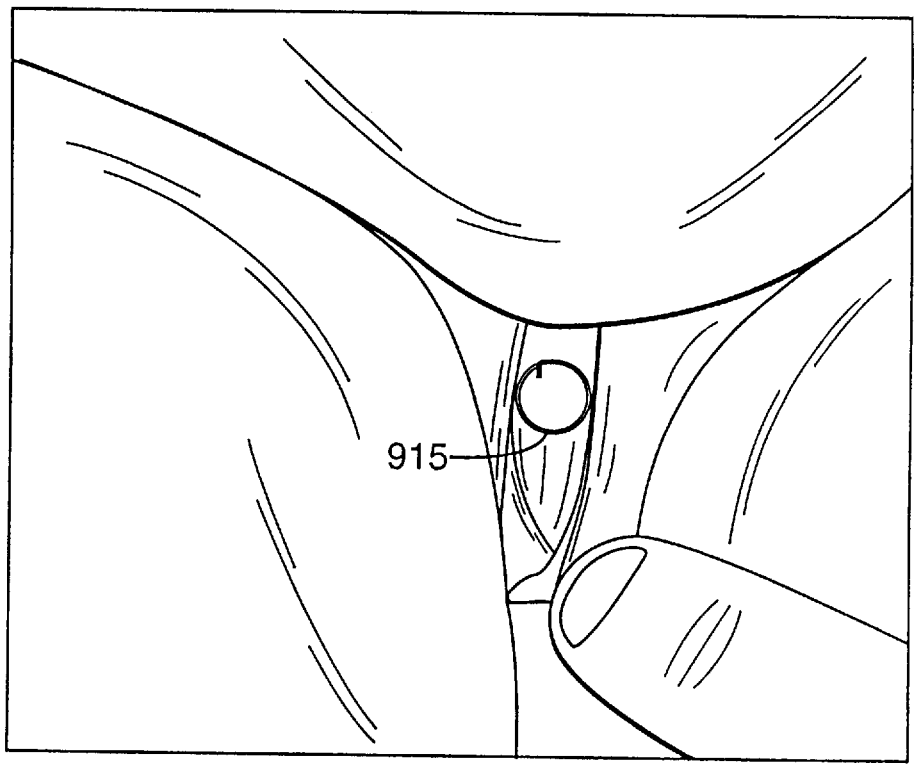
Figure 56:
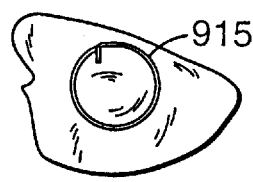

Turning to FIG. 40, the lower end of device 600 includes vacuum port 760 with associated vacuum line 770, as shown. Vacuum port 760 preferably is one-piece with and molded as a part of base 485. Sealing ring 775 provides a vacuum seal between the upper portion 777 of the hub of base 485, and the remainder of base 485.

Locking mechanism 800 will now be described with reference to FIGS. 41–47. Locking mechanism 800 includes thumbwheel 810 with ridged surface 815, rod support 820, and upwardly extending locking rods 830, shown in FIG. 47. Locking rods 830 extend upwardly from apertures 840 in supports 820, and into and through corresponding apertures in handle 670. Rods 830 include detents 850 at their upper ends, for engaging and locking into apertures 860 (FIGS. 45–46) in base 485. Locking rods 830 extend on opposite sides of handle 650. Thus, handles 605, 650 and 670, as well as base 485, are all held in a substantially fixed angular orientation with respect to each other. Handles 650, 670 preferably are allowed to slide along locking rods 830. Thumbwheel 810 is placed over and tightened down with respect to base 485, holding all of the component parts substantially in place with respect to each other.

Referring to FIGS. 48–56, incontinence treatment device 900 includes many of the features and advantages described with respect to the previous embodiments. To simplify the description, not every feature and advantage will be repeated verbatim here. Those of ordinary skill will appreciate that the previous descriptions of e.g. inflation balloons, corresponding inflation mechanisms, vacuum devices, viewing devices, methods of use, materials and other features of previously described embodiments are equally applicable here.

Incontinence treatment device 900 includes first generally cylindrical member 905 and second generally cylindrical member 910 disposed generally concentrically over first member 905. A coil-shaped staple 915 is also disposed generally concentrically over first member 905, as shown. Second member 910 defines recess or cutout portion 920 for contacting engagement end 925 of staple 915. As can be immediately appreciated, rotating second member 910, e.g. when a surgeon or other user of device 900 turns raised portion 930 of member 910, causes staple 915 to rotate by a corresponding amount in the same direction. A sharp, tissue-penetrating tip of staple 915 thus penetrates and is driven into the desired anatomical tissue, which is held in place e.g. by vacuum, as described earlier. As staple 915 advances longitudinally into the desired anatomical tissue, member 910 advances longitudinally with it, maintaining the driving contact between them.

Embodiments of the invention provide a significant advantage, in that no complicated locking or retaining mechanism is needed to hold staple 915 in place with respect to member 910 during the rotation/implantation process. Correspondingly, after staple 915 has been implanted, member 910 can be disengaged from staple 915 simply by withdrawing device 900; no special release mechanisms or other devices are needed to disengage the one from the other.

FIG. 48 illustrates "left hand" configurations of recess 920 and staple 915, in that member 910 is rotated to the left (as viewed from a distal end of device 900) to advance staple 915. Those of ordinary skill will appreciate that embodiments of the invention equally contemplate "right hand" configurations as well. If desired, recess 920 of member 910 can be substantially rectangular or otherwise shaped such that both "left hand" and "right hand" staples 915 can be used.

Device 900 further includes set 935 of suction apertures or slots 938 disposed through first member 905 and fluidly coupled to a vacuum source, such as a syringe or vacuum pump, for example, through vacuum port 940. As with previous embodiments, member 905 can include an inwardly curved shape in the region of apertures 938, according to the shape desired for the surrounding anatomical tissue. Other aspects of the vacuum application process will be appreciated from previously described embodiments.

Device 900 further includes inflation balloon 945, also generally in accordance with previous embodiments. Inflation balloon 945 is fluidly coupled with inflation port 950, which in turn is coupled with an inflation source (such as syringe 955, FIG. 52, a pump, or the like). To better enable an operator of device 900 to judge the degree to which balloon 945 is inflated, device 900 further includes pilot balloon 960, disposed at port 950 or another location for easy visibility.

First member 905 defines hollow interior 965 for receiving viewing device 970, shown in e.g. FIG. 49. Viewing device 970 is a 4 mm cystoscope, according to one embodiment, but cystoscopes of other sizes, and other viewing devices (including, but not limited to, endoscopes, as described previously), can be used. Viewing device 970 preferably includes light source 975, e.g. a fiber optic light source. O-ring 980 provides a seal between viewing device 970 and first member 905. As will be apparent, viewing device 970 is constructed such that the operator of device 900 can view a region at a distal end of the first generally cylindrical member, before, during and/or after a staple-insertion procedure. Accordingly, member 905, at least in the region of tip 982 thereof, is preferably composed of clear or generally transparent material.

Tip 982 can include a generally helical trough 983 to prevent undesired lateral or other movement into the adjoining tissue. At the end of trough 983, tip 982 can include stop 984, which contacts engagement member 925 at the end of its normal course of travel in trough 983, to prevent over-insertion of staple 915. Of course, stop 984 is an optional feature, as is trough 983.

In the embodiment illustrated in FIG. 48, first member 905 also includes an extended portion 985, which can be one-piece with member 905 or separately joined to it. Extended portion 985 supports inflation balloon 945 in a desired position with respect to the bladder, bladder neck, urethra or other anatomical structure to which staple 915 is being applied. Portion 985 can be formed of a flexible and/or rubbery material, according to one embodiment, for easier insertion and to reduce the possibility of trauma to the urethra, bladder or other tissue.

FIG. 50 is an end view of staple 915, according to one embodiment. The main body of staple 915 is generally in the form of a coil or spiral, as previously described. A sharp tip is disposed at one end of main body 990, and engagement portion 925 at the other, as shown. Engagement portion 925 is constructed to engage second cylindrical member 910, e.g. at recess 920, and to engage first cylindrical member 905 along optional trough 983. Engagement portion 925 also can be grasped for removal of staple 915, should removal be desired. Staple 915 can be removed simply and easily, merely by reversing its path of rotation into the tissue.

Staple 915 has a generally circular shape defining a circumferential path 995 when viewed from an end of staple 915, e.g. in the manner of FIG. 50. As can be seen, engagement portion 925 is generally disposed along circumferential path 995. This configuration is in contrast to certain prior art staples, in which a corresponding portion extends all the way, or substantially all the way, to and/or through the central axis of the staple instead of being generally along the circumferential path defined herein. In addition, the staple can be placed such that in tissue structures with a lumen, e.g. the urethra, bladder neck, or a blood vessel, the staple can be in the wall of the lumen structure and covered by tissue. By keeping engagement portion 925 generally along path 995, instead of having it extend all the way to the center, embodiments of the invention allow room for accommodation of delivery apparatus, a viewing device, a balloon and/or other structure, in the manner previously described. In addition, fluids, e.g. bodily fluids, are able to pass in the lumen defined by the staple.

As can be seen from e.g. FIG. 50, engagement portion 925 extends no more than about 33 percent into the interior of staple 915 along a diameter thereof, preferably no more than about 25%, more preferably no more than about 15%, and even more preferably no more than about 10% into the interior along the diameter.

According to other embodiments, engagement portion 925 can be disposed entirely within circumferential path 995. Although this disposition might tend to require more precise positioning for positive engagement with first member 910, it reduces even further the degree to which an interior portion of staple 915 might tend to be obstructed.

Staple 915 generally defines a helix extending along a helical path, engagement portion 925 forming an end of the helix without generally deviating from the helical path. Staple 915 can be formed from a generally stiff wire formed into a helical shape, according to one embodiment, and a cross-section of the wire can generally flatten out toward engagement portion 925 of staple 915, for better tissue penetration. Alternatively, the entire staple can be of flattened cross-sectional shape, e.g. in the form of a rectangular cross-section, to provide better flexibility and deformability as may be desired in particular surgical situations.

According to one embodiment of staple 915, visible in e.g. FIG. 48, engagement portion 925 is extended in the longitudinal direction, relative to the remainder of the staple, for better engagement with staple advancing device/second member 910.

Device 900 can optionally include a hood, disposed over at least the sharp tip of staple 915, for protection during insertion of the apparatus into the patient. The hood prevents the sharp tip from "catching" on, penetrating, or otherwise undesirably contacting anatomical tissue before staple 915 has been properly positioned by device 900. The hood also prevents uncoiling, unwinding or other undesirable extension or deformation of staple 915 during insertion. In one embodiment, the hood is bivalved and withdrawn from the patient once the device is in place, e.g. in the manner of a bivalved speculum, prior to deployment of the staple.

Additionally, a collar can be placed over the knurled end 930 of staple advancing member 910. The collar constrains staple advancing member 910 so that it cannot move axially with respect to the remainder of device 900, during initial insertion. The collar then may be removed for deployment of the staple.

According to embodiments of the invention, staple 915 can be internally hollow or include a hollowed out interior area. Medication thus can be placed within the staple, e.g. epithelial growth inhibitor, sclerosing agent, and/or antibiotic, for administration immediately upon implantation and/or over an extended period of time thereafter. Openings can be displaced at one or both ends of the staple, with one or more plugs in place as needed. Additionally, or alternatively, staple 915 can be used for delivery of e.g. absorbable suture material, with such material remaining in place as the staple is backed out of the tissue. Accordingly, initially the suture would be disposed within the staple, with at least one end protruding from the staple. Once the staple has been introduced, at least the protruding end is grasped and the staple removed, leaving the suture in place. The ends of the suture then would be tied off.

Once anatomical tissue has been held in place for a certain length of time, e.g. six weeks or more, staple 915, suture or other holding material may no longer be needed to keep the tissue in the desired configuration. Accordingly, staple 915 itself can be absorbable, as well as any suture material that is used along with it. Additionally, staple 915 can include a textured exterior, and/or a surface coating, to induce scarring and thus promote retention of the desired shape. Staple 915 then can be absorbed, or removed physically, if desired.

In operation, cystoscope or other viewing device 970 is placed within treatment device 900, specifically within hollow interior 965 of first member 905. Device 900 then is placed into the urethra of the patient, so that inflation balloon 945 is within the bladder. Inflation balloon 945 then is inflated, e.g. with syringe 955, and device 900 is pulled back so that balloon 945 contacts the bladder neck. The operator of device 900 thus is able to more accurately move staple 915 to the correct location within the urethra or bladder neck.

A vacuum then is applied to suction apertures or slots 938 through vacuum port 940, and consequently the tissue or the urethra is pulled into slots or apertures 938, i.e. into a desired configuration, with the aid of cystoscopic or other visualization. Staple advancing member 910 then is rotated to implant staple 915, again under cystoscopic or other visualization. Once implanted, the vacuum is released and balloon 945 is deflated. Device 900 then is completely and easily removed from the patient, leaving staple 915 implanted.

Embodiments of the invention described with respect to FIGS. 48–56 provide a number of advantages. The amount of staple material left exposed to the interior of the urethra or bladder neck is significantly reduced. The staple may be placed submucosally, or in the tissue surrounding the urethra, or as otherwise may be desired, e.g. with only a small portion of the staple exposed, to facilitate extraction. According to one embodiment, only the end of engagement portion 925 is exposed once implantation is complete. This feature tends to reduce the possibility of stone formation, infection, and other adverse effects.

FIGS. 57–61 show multiple surgical-staple deployment devices and methods according to embodiments of the invention. These embodiments include many of the features and advantages described with respect to the previous embodiments. To simplify the description, not every feature and advantage will be repeated verbatim here. Those of ordinary skill will appreciate that previous descriptions of e.g. inflation balloons, inflation mechanisms, vacuum devices, viewing devices, methods of use, materials and other features of previously described embodiments are equally applicable here and are intended to be applied to all of the below-described embodiments.

Anastomoses

Figure 57:
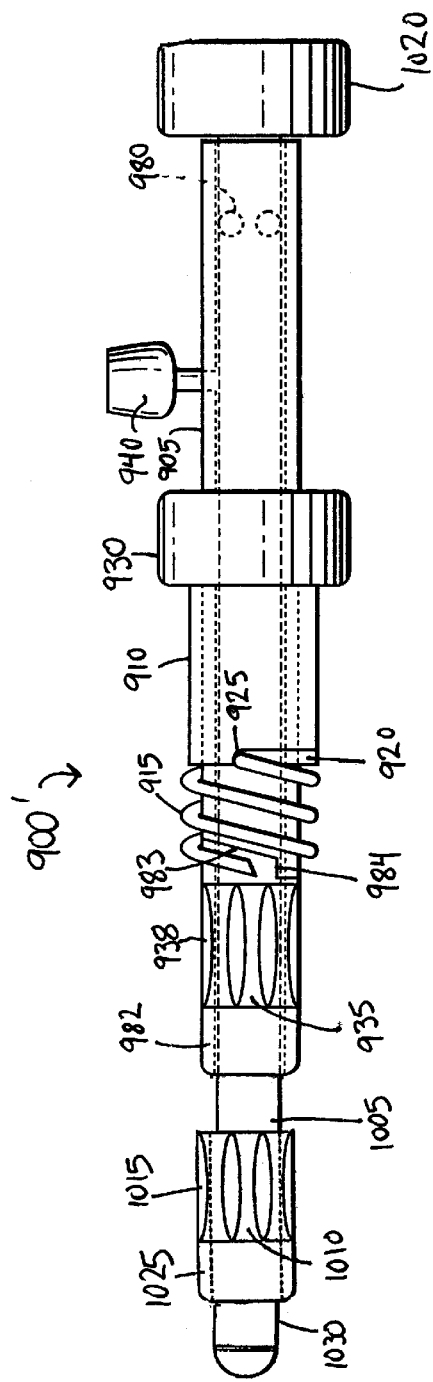
FIG. 57 shows a side view of a device for creating an end-to-end anastomosis, according to an embodiment of the invention.

FIG. 57 shows apparatus 900' for anastomosing two anatomical structures, such as blood vessels. Apparatus 900' includes many previously described elements, including first generally cylindrical member 905, second generally cylindrical member 910, staple 915, set 935 of suction apertures 938, and vacuum port 940. Apparatus 900' additionally includes a third, generally cylindrical member 1005. Member 1005 supports a second set 1010 of suction apertures or apertures 1015, fluidly coupled to a vacuum source, such as a syringe or vacuum pump, through one or more vacuum ports 940. Member 1005 extends longitudinally along the entire length of apparatus 900', emerging at the right hand side thereof, as viewed in FIG. 57, at handle 1020. Also attached to member 1005, at the left hand portion thereof, are tip 1025 and extended portion 1030, similar to tip 982 and portion 985 described previously.

Handle 1020 is attached to, and preferably is rigidly mounted with respect to, member 1005. By pushing, pulling, turning or otherwise manipulating handle 1020, an operator of apparatus 900' can correspondingly move member 1005 and set 1010 of suction apertures 1015. Drawing a vacuum or creating suction through apertures 1015 and/or apertures 938 attracts and holds surrounding anatomical tissue. Thus, the operator can rotate apertures 1015 and/or move them to the left or to the right, in a desired manner, to correspondingly move anatomical structure, or an anatomical structure portion, such as a blood vessel, into a desired configuration for anastomosis or other purpose. Similarly, an operator can also position apertures 938, and any anatomical tissue, structure or structure portion attracted thereto, by rotating or sliding cylindrical member 905.

Apparatus 900' thus includes a pressure differential device comprising first set 1010 of suction apertures 1015 and second set 935 of suction apertures 938, respectively fluidly coupled to one or more vacuum ports 940. First set 1010 of suction apertures 1015 and second set 935 of suction apertures of 938 are constructed and arranged for relative movement. When suction is applied and portions of anatomical structure are attracted to and held in place by apertures 938, 1015, relative movement of the apertures, either directed by the operator or occurring as a natural result of the suction, causes corresponding relative movement of the anatomical structure portions. Where the anatomical structure is vascular structure and the anatomical structure portions comprise blood vessels, for example, this relative movement draws the blood vessels into an anastomosed configuration.

More specifically, according to one embodiment, apparatus 900' is deployed e.g. through a first blood vessel or other anatomical structure that is to be anastomosed to a second blood vessel or other anatomical structure. The operator of apparatus 900' extends tip 1030 and set 1010 of suction apertures 1015 to and through the first vessel and into the second vessel. Suction apertures 938 are positioned as desired within the first vessel. Vacuum then is applied to suction apertures 938, 1015, either simultaneously or sequentially, drawing the vessels into contact with their respective sets of apertures. In this case, the vacuum or suction that is applied causes a pressure differential with respect to the lumen of the anatomical structure, causing movement of the anatomical structure to a desired configuration for treatment. The operator then pulls the second vessel toward the first vessel by partially withdrawing generally cylindrical member 1005 using handle 1020. Of course, rotation or other movement of handle 1020 will cause corresponding rotation or movement of the second vessel, as needed. The operator can also manipulate member 905 to move the first vessel, as previously described. Once the two vessels are drawn into an anastomosed configuration, the operator turns handle 930 to advance helical staple 915 via applicator member 910 into the vessels, to create a permanent anastomosis. Handle 930, applicator 910, and/or helical staple 915 each comprise portions of, or all of, a stabilizing device according to this embodiment, operably coupled with the pressure differential device including e.g. suction apertures 938, 1015, to stabilize first and second anatomical structure portions or vessels in a desired configuration.

Thus, a deployment device according to an embodiment of the invention is placed during surgery on the vessels. For an end-to-end anastomosis, ends of the relevant vessel are approximated over the deployment device. Vessel ends are held in contact by vacuum. Appropriately sized vacuum slots or suction apertures are present in the deployment device to accommodate the tissue. A surgical stabilizing or fastening agent or holding device, such as a helical staple as described previously, is deployed, once the ends of the relevant vessels are properly positioned, to effect the anastomosis. According to other embodiments, especially for end-to-side and side-to-end anastomoses, the deployment device and the stabilizing or fastening agent are modified to have appropriately sized and shaped slots to accommodate the end of the vessel and the side of the vessel being anastomosed. According to this embodiment, tissue is held in place by vacuum and the stabilizing or fastening agent is modified to function as e.g. a linear press-fit staple, rather than as a helical staple. Side-to-side anastomoses also can be accomplished with an appropriately shaped and dimensioned staple or other stabilizing or fastening agent. Thus, embodiments of the invention are well-suited to perform end-to-end, end-to-side, and side-to-side anastomoses. According to particular embodiments, helical staple 915 of the FIG. 57 embodiment (or other stabilizing or fastening agent) remains free of the lumen of the anastomosis, minimizing the risk of thrombosis and other complications.

As referenced earlier, embodiments of the invention can be used with multiple anatomical structures, not just blood vessels. For example, the urethra, bile duct, fallopian tube, vas deferens, rectum, and small bowel, to name several examples, are among the anatomical structures that can be anastomosed according to embodiments of the invention.

Biliary Tract—Anastomoses

End-to-end, end-to-side, and side-to-end anastomoses can be accomplished in the biliary tract in a manner analogous to that described for e.g. vascular anastomoses. The use of a vacuum deployment device and appropriately sized staples, helically or linearly driven, allows biliary anastomoses of various sizes, including diameters of the extrahepatic bile ducts, to be performed.

Gastrointestinal Surgery—Intestinal Anastomoses

End-to-end, end-to-side, side-to-end and side-to-side anastomoses also can be accomplished in the intestinal tract in a manner analogous to that described for vascular anastomoses, above. The use of a vacuum deployment device as described herein and appropriately sized staples, helically or linearly driven, allows intestinal anastomoses of various sizes, including for small pediatric intestine, to be performed.

Anastomosis of Urethra Following Prostatectomy or Radical Prostatectomy

Following prostatectomy, end-to-end or end-to-side anastomosis can be performed using a helical staple and staple deployment device as described herein.

Closure of Anatomical Structure. e.g. Fallopian Tube or Vas Deferens

Figure 58:
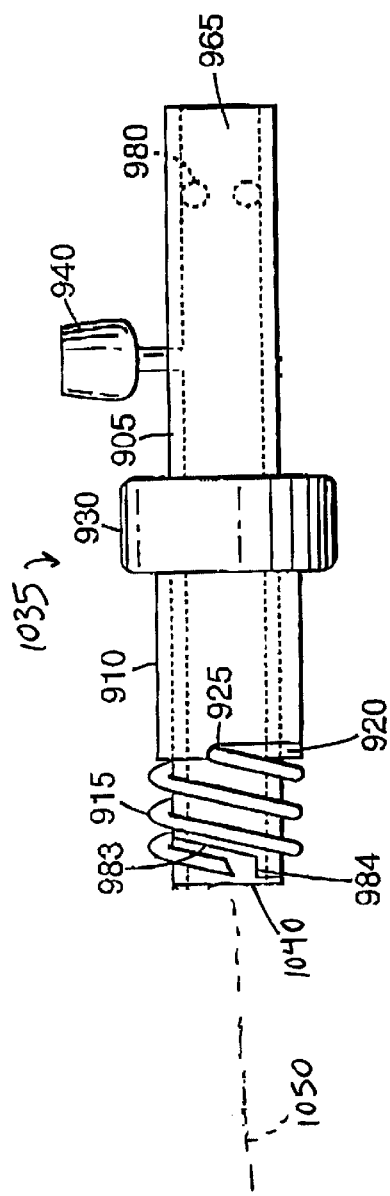
FIG. 58 is a side view of an apparatus for closure of anatomical structure, such as a fallopian tube, according to an embodiment of the invention.

Turning to FIG. 58, apparatus 1035 is configured in or as a catheter, for example, with a diameter small enough to allow catheter entry into an anatomical structure such as a fallopian tube of a female patient. Upon entry into the tube, a vacuum is drawn using e.g. vacuum port 940. Instead of using suction apertures 938 as with previous embodiments, end 1040 of first generally cylindrical member 905 is generally open, providing direct, longitudinal application of vacuum to the fallopian tube or other structure via one or more end apertures. In some situations, it may be desirable to provide one or more circumferentially located suction apertures, in the manner of apertures 938 but preferably on a reduced-diameter cylindrical member, in addition to or instead of one or more end apertures.

Application of vacuum causes the fallopian tube or other anatomical structure to close tightly or collapse on itself. Helical staple 915 or other holding device then is rotated/advanced, e.g. into or near the circumference of the fallopian tube or other structure, to hold the collapsed structure in a permanent collapsed configuration. The invention contemplates use with other anatomical structures to be closed, e.g. the vas deferens to accomplish functional vasectomy.

Also according to this embodiment, wire 1050 optionally can be deployed within the lumen of the fallopian tube or other anatomical structure, to sufficiently damage the tissue prior to placement of the helical staple or other stabilizing or fastening agent. Tissue damage in this manner tends to promote more rapid tissue growth, better ensuring closure of the anatomical structure. According to embodiments of the invention, wire 1050 can be a resistive wire that is heated and thus causes thermal damage. Alternatively, or additionally, wire 1050 can be an abrasive wire that damages the tissue by direct abrasive contact.

Thus, in the manner of previous embodiments, apparatus 1035 treats an anatomical structure having a lumen, using a pressure differential device and a stabilizing device. Additionally, or alternatively, the pressure differential device itself can be used as a stabilizing device, optionally in conjunction with a separate stapling mechanism or other surgical tool or procedure. Apparatus 1035 is inserted into e.g. the fallopian tubes, and the lumen of the fallopian tubes is obliterated in connection with tissue damage, negative pressure differential (e.g. suction), and/or staple placement, in the manner described. The diameter of apparatus 1035 is selected appropriately to obliterate whatever anatomical structure is being closed or narrowed, in connection with tissue damage and/or staple placement. Functional vasectomy, tubal ligation, and additional closures are contemplated according to embodiments of the invention.

Reversal of Tubal Ligation or Vasectomy

Embodiments of the invention can be used to accomplish anastomosis of the fallopian tubes, as part of a procedure to reverse tubal ligation, in a manner analogous to that described for vascular anastomoses, above. Similarly, anastomosis of the vas deferens can be accomplished as part of a procedure to reverse vasectomy, also in a manner analogous to that described for vascular anastomoses, above. Additionally, using an inflatable balloon to move a fallopian tube, vas deferens or other anatomical structure to a non-constricted configuration can aid in the treatment/reversal of functional vasectomy or tubal ligation. Stabilization with a helical staple or similar device can follow.

Vascular Closure or Wound Closure

According to the embodiments of FIGS. 59–60, apparatus 1045 comprises guide 1050, which for simplicity of illustration is shown in cross-section. Guide 1050 preferably includes extendable portion 1055 and optional base portion 1065. Portion 1055 is moveable with respect to base portion 1065, from a non-deployed configuration shown in FIG. 59 to a deployed configuration shown in FIG. 60. In the non-deployed configuration, guide 1050 is generally cylindrical in shape. In the deployed configuration, guide 1050 forms a generally conical shape, or partially conical shape. During deployment, portion 1055 generally pivots, bends, expands or otherwise moves outwardly relative to base portion 1065 and/or relative to the remainder of apparatus 1045 to form the generally conical shape. As illustrated, portion 1055 then defines generally conical channel 1073, which in cross-section is seen as a generally V-shaped opening or channel. The shape of channel 1073 enhances the effectiveness of suction applied through e.g. suction apertures 938, apertures in the end face of member 905, or the like. Once suction or pressure differential is applied via e.g. suction apertures 938, e.g. in the manner previously described, anatomical structure is drawn into channel 1073 to form a desired configuration.

Then, helical staple 915 or other stabilizing or fastening agent can be deployed, in the manner previously described, to stabilize the anatomical structure in the desired configuration. According to one aspect, as illustrated in FIG. 59, guide 1050 defines indentations 1075 for at least partially receiving helical staple 915, allowing guide 1050 to close more tightly against the remainder of apparatus 1045 to present a narrower profile.

Guide 1050 can be actuated back and forth between the deployed and non-deployed positions by a variety of mechanisms or devices. According to one embodiment, an inflatable balloon, in the manner of previous embodiments, can be used to apply force to the distal ends of portion 1055, spreading it apart to create V-shaped or conical channel 1073. Accordingly, instead of terminating at the left end as viewed in FIG. 60, apparatus 1045 can extend to the left to provide support for an inflatable balloon in the manner of previous embodiments. Guide 1050 can also be of greater length, extending more to the left as viewed in FIG. 60, to provide enhanced support for structure or tissue that is drawn into channel 1073 by vacuum. The diameter of member 905 (or equivalent mandrel-type body) can be made sufficiently small so as to allow a sufficient amount of closure of the anatomical structure.

Guide 1050 itself can be inflatable and actuated by way of port 950, for example. According to another embodiment, guide 1050 can be constructed of a memory material, such as Nitinol. Such memory material can be temperature-dependent, for example, bending and/or expanding to the deployed configuration of FIG. 60 upon heating, e.g. heating by the body temperature of the patient. A spring material also can be used, and/or guide 1050 can be spring-loaded. A telescopic configuration of guide 1050 also is contemplated, according to aspects of the invention, in the manner of e.g. an expandable drinking cup that telescopes from a compact configuration to a deployed configuration. A screw-drive mechanism also is contemplated.

The embodiment of FIGS. 59–60 has multiple uses, such as vascular closure, wound closure, and ligation of gastrointestinal hemorrhage, to name a few examples. Arteriotomy resulting from cardiac catheterization, peripheral angiography, or placement of an intra-aortic balloon pump, for example, requires closure to prevent immediate hemorrhage and related complications, e.g. subsequent pseudoaneurysm formation. In these instances, apparatus 1045 provides a generally V-shaped or generally conical channel that is oriented such that a long axis of the channel is parallel to the long axis of the blood vessel. Vacuum is then applied such that the edges of the arteriotomy are drawn into the channel and approximated as the shape of the channel urges the edges of the blood vessel together. At this point, helical staple 915 or other stabilizing or fastening agent of appropriate dimension, pitch, etc. is deployed to effect rapid, accurate arteriotomy closure without requiring formal suturing in the operating room. The procedure may use an appropriately sized balloon-tipped catheter, or other device, to help ensure proper placement.

Similarly, surgical wounds, especially laparoscopic surgical port wounds, can be closed with apparatus 1045 or other embodiments discussed herein. In the case of apparatus 1045, vacuum is applied and the edges of the wound are elevated into channel 1073. With the edges of the wound urged into contact by the channel, helical staple 915 or other stabilizing or fastening agent is deployed and wound closure thus accomplished.

In the case of e.g. gastrointestinal hemorrhage or ulcer, treatment of bleeding may not be feasible by traditional endoscopic or surgical procedures. With embodiments of the invention, on the other hand, the combination of vacuum deployment device and e.g. helical staple can serve to constrict the artery feeding the site of the hemorrhage, allowing the artery to thrombose or obliterating the lumen of the artery. Current methods require coils or thrombogenic substances to be passed by a catheter into the responsible vessel. Some vessels are too large for management by these procedures. Some vessels are too distal to ensure delivery of the thrombogenic material to the appropriate vessel. Another advantage of helical staple 915 is that the lumen of the responsible vessel may be calibrated to ensure blood flow to important collateral vessels, while simultaneously reducing blood flow to the bleeding vessel. With the embodiment of FIGS. 59–60, preferably in combination with endoscopy, V-shaped or conical channel 1073 is brought into contact with edges of the tissues surrounding the bleeding vessel. Vacuum then is applied and the edges of the tissue surrounding the vessel elevated into the channel by the vacuum. With edges of the tissue thus urged into contact by the channel, apparatus 1045 then applies helical staple 915 in the manner previously described. Ligation of the bleeding vessel thus is accomplished. The described apparatus and method are usable for both arterial and venous hemorrhage, for example.

According to one embodiment, a guide wire is left in place at the conclusion of the initial invasive procedure, e.g. the cardiac catheterization or the like. Apparatus 1045 then is placed over and moved along the guide wire until it is in contact with e.g. the femoral or external iliac artery, or other anatomical/vascular structure where the arteriotomy was made. The other embodiments of the invention described herein (i.e. beyond that of FIGS. 59–60) also can use a guide wire or other guide structure for proper placement.

Thus, in the manner of previous embodiments, apparatus 1045 treats an anatomical structure having a lumen, using a pressure differential device and a stabilizing device. The pressure differential device applies negative differential pressure, in the case of vacuum or suction, to cause movement of the anatomical structure to a desired configuration for treatment. In the case of an inflatable balloon, used to actuate guide 1050 and/or dilate the anatomical structure, as may be desired, the pressure differential device creates a positive pressure differential. Vascular closure, wound closure, treatment of gastrointestinal hemorrhage, and the like can be accomplished with relative ease and with reduced trauma.

Endoluminal Scalpel with Simultaneous Repair

Figure 61:
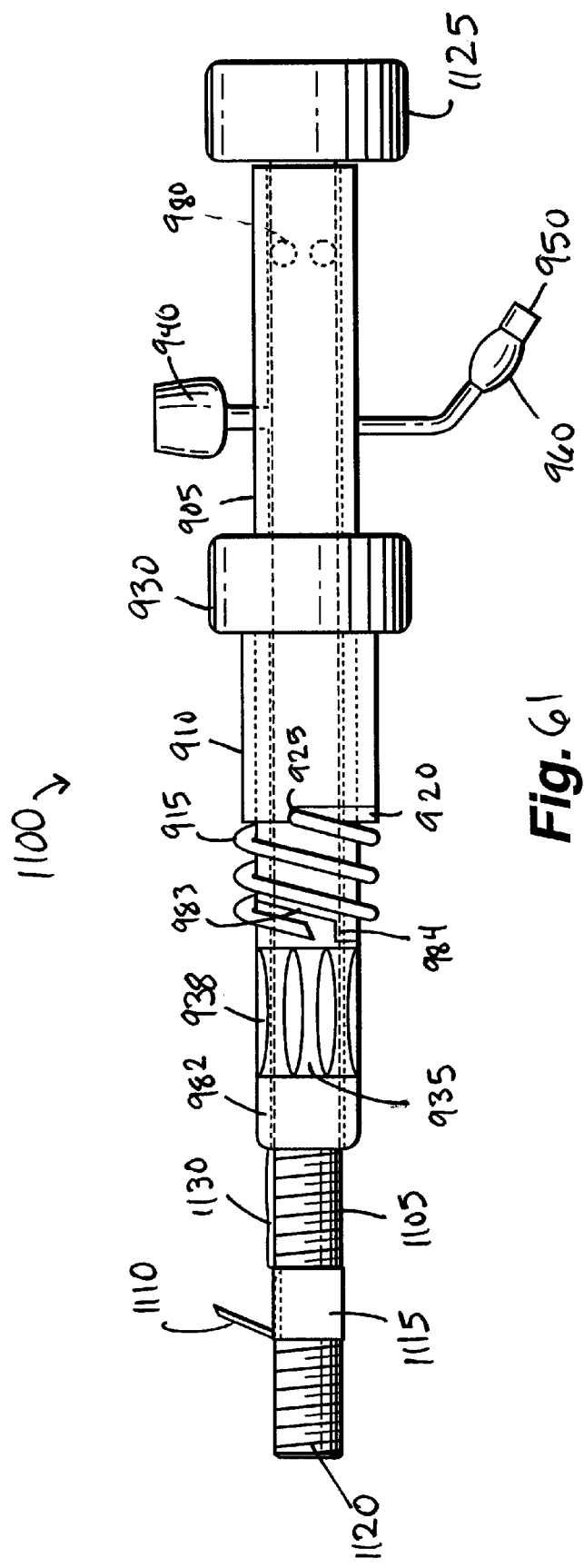
FIG. 61 is a side view of an endoluminal scalpel device, according to an embodiment of the invention.

FIG. 61 shows an alternative embodiment according to the invention. In many respects, apparatus 1100 is similar to the various embodiments previously described. Additionally, apparatus 1100 includes generally cylindrical member 1105, extending longitudinally along an interior portion of apparatus 1100. Apparatus 1100 includes cutting device 1110, e.g. a knife, scalpel blade or similar object with a sharp cutting edge. Ferrule 1115 supports cutting device 1110 for movement in the longitudinal direction of apparatus 1100. According to the illustrated embodiment, member 1105 includes screw threads 1120, which correspond with internal screw threads (not shown) of ferrule 1115. As an operator of apparatus 1100 turns handle 1125, connected at the opposite end of member 1105, ferrule 1115 and cutting device 1110 move longitudinally back and forth.

The orientation of ferrule 1115 and cutting device 1110 relative to the remainder of apparatus 1100 can be maintained in a number of ways, according to embodiments of the invention. According to one example, member 1105 includes a pin-and-slot indexing indent mechanism, generally preventing rotation of ferrule 1115 as member 1105 rotates. A pin can be disposed on the inside of ferrule 1115, for example, pointing inwardly and riding in a slot in member 1105 or separate structure running alongside member 1105.

Cutting device 1110 is moveable between an extended position, illustrated in solid lines in FIG. 61, and a retracted position, illustrated in dashed lines in FIG. 61. Multiple different kinds of mechanisms or devices can be provided for this purpose. For example, a pulley and spring can be provided generally at the intersection of cutting device 1110 and ferrule 1115, retracting when an associated cable is released and extending when the cable is pulled. The cable can extend to or toward handle 1125, for example. Alternatively, a screw drive mechanism can be provided to pivot cutting device 1110 relative to ferrule 1115. A pressure balloon also could be provided, controlled by way of e.g. port 950.

Apparatus 1100 also comprises repair material 1130, connected for movement with ferrule 1115 and knife 1110. Thus, as the operator turns handle 1125, ferrule 1115, knife 1110, and repair material 1130 are advanced simultaneously along the wall of the vessel or other anatomical structure. As will be appreciated, apparatus 1100 is constructed to cut the anatomical structure and to apply repair material 1130 in connection with just a single motion by the operator of apparatus 1100, i.e. rotation of handle 1125, according to this embodiment.

Repair material 1130 can be pre-sized to fit the particular length of cut that will be created in the vessel or other anatomical structure. According to one example, an angiogram reveals how long the stricture or lesion is, and the patch of repair material is sized appropriately. Alternatively, or additionally, repair material 1130 can be cut during treatment.

Suction is applied through one or more suction apertures 938 or the like to draw and secure repair material 1130 and, preferably, the anatomical structure itself, into a desired configuration. Handle 930 then is turned, in the manner of previous embodiments, to advance helical staple 915 or other fastening or stabilizing agent into position.

According to this embodiment, apparatus 1100 can be used to restore flow to an artery, for example a coronary artery or a peripheral artery, as will now be described with reference to generally schematic FIGS. 62–67.

First, apparatus 1100 is deployed such that cutting device 1110 is within the anatomical structure to which flow, e.g. blood flow, is to be restored. In one example according to FIG. 62, vessel 1132 is a coronary artery having constriction 1134, such as a lesion or plaque deposit. For certain types of constrictions, or for other reasons, it may be desirable to use guide wire 1140, placed across or through constriction 1134 within vessel 1132, instead of or in addition to apparatus 1100. FIGS. 62–67 should be considered to apply equally to both guide-wire embodiments and non-guide-wire embodiments.

Figure 62:
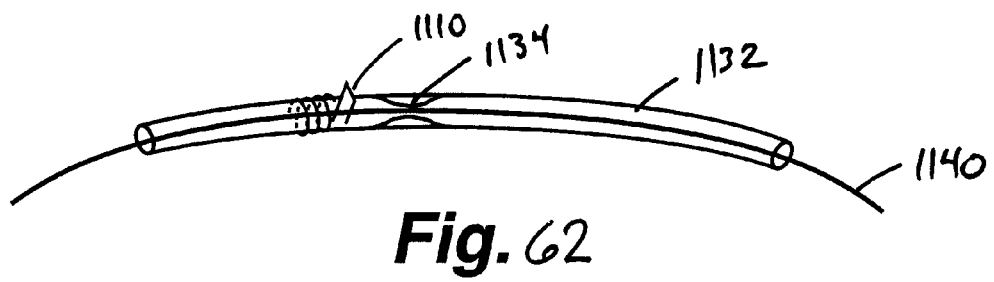
FIGS. 62–67 are generally schematic views showing steps in the operation of the FIG. 61 apparatus.
Figure 63:
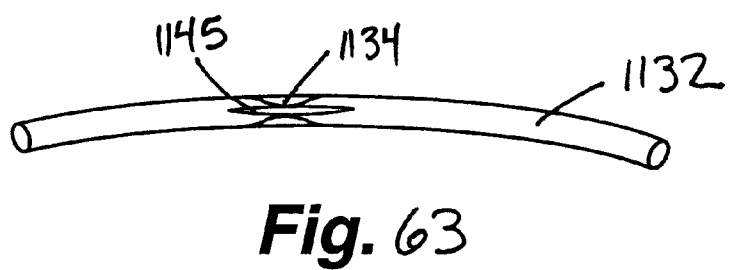
Figure 64:
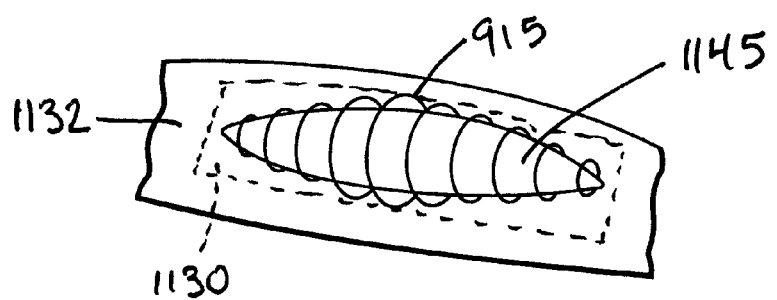
Figure 65:
Figure 66:
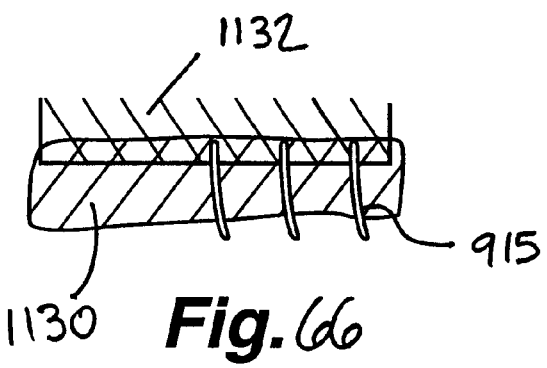
Figure 67:
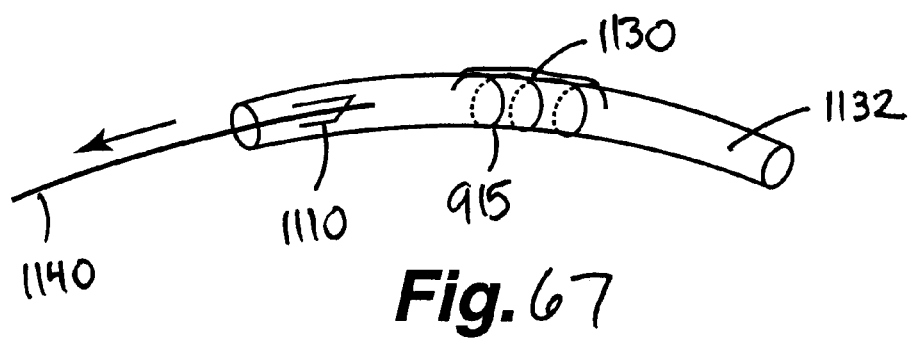

When deployed, as indicated schematically in FIG. 62, cutting device 1110 advances along e.g. guide wire 1140 (and/or generally cylindrical member 1105 in the case of apparatus 1100). As cutting device 1110 advances, it cuts the surrounding anatomical structure 1132 and opens constriction 1134 within it. Arteriotomy 1145 thus is created, as shown in e.g. FIG. 63.

According to embodiments of the invention, repair of arteriotomy 1145 is accomplished generally simultaneously with its production, by use of repair material 1130. Repair material 1130, or equivalent substance or material, is automatically deployed over the arteriotomy 1145 as ferrule 1115 is advanced by screw threads 1120 and/or as cutting device 1110 advances in relation to guide wire 1140. Suction then can be applied. Helical staple 915 or other holding device then is driven to secure the repair material in place with respect to arteriotomy 1145, generally resulting in the disposition illustrated in FIG. 64. Staple 915 can be of varying diameter or can be flexible to achieve varying diameter, or can be of constant diameter throughout its entirety. The repair material/substance is held in place by helical staple 915, thereby forming an anastomosis between anatomical structure 1132 and repair material/substance 1130, with reference to FIGS. 65–67.

Subsequently, cutting device 1110 and guide wire 1140 are removed. According to one embodiment, cutting device 1110, when subjected to traction, folds such that its cutting edge is no longer engaged. Cutting device 1110 is shown in the removal position in FIG. 67, for example.

Thus, minimally invasive cardiac surgery is one example that can be accomplished according to the invention. No sternotomy or other chest incision is required. A guide wire or apparatus is placed through a region of constriction of the coronary artery. Helical staple 915 or similar stabilizing or fastening agent then is deployed at one end of the stricture. A screw drive or similar advancing mechanism then translates a knife or other cutting device 1110 to cut the coronary artery in the longitudinal axis thereof, while simultaneously advancing repair material to effect coronary angioplasty. The arteriotomy and the repair thus occur generally simultaneously. Cutting device 1110 can be considered all or part of a movement device constructed to cause movement of the anatomical structure to a desired configuration, e.g. a cut configuration, for treatment. A similar procedure can be employed to effect angioplasty in peripheral vascular surgery, for example.

Aspects of these embodiments are also believed to have special relevance to treatment situations involving non-plastiable lesions, calcified plaque, otherwise non-stentable anatomical structures, such as non-stentable coronary arteries, and the like. Additionally, in other situations, aspects of these embodiments can be used in combination with an inflatable balloon, in the manner described previously, for example, to cause dilation of the coronary artery or other structure prior to, or instead of, the cutting and repairing described herein.

Treatment of Morbid Obesity

Figure 68:
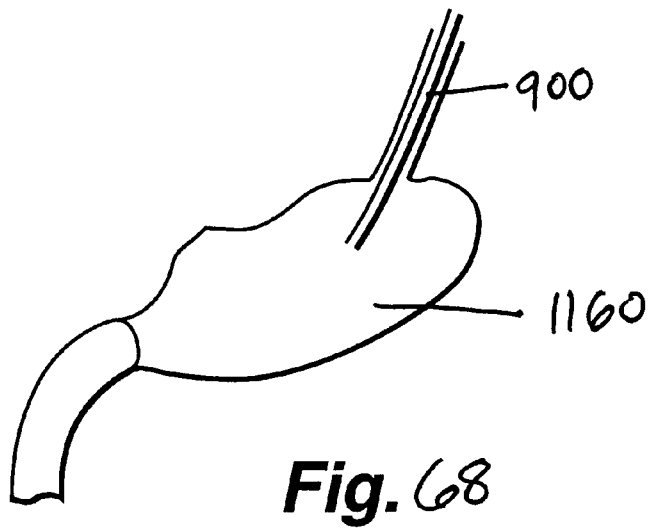
FIGS. 68–71 show operational steps in use of an apparatus according to embodiments of the invention for treatment of morbid obesity.
Figure 69:
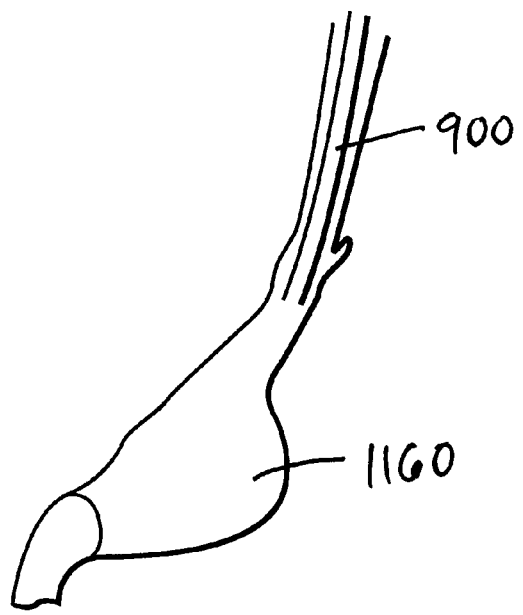
Figure 70:
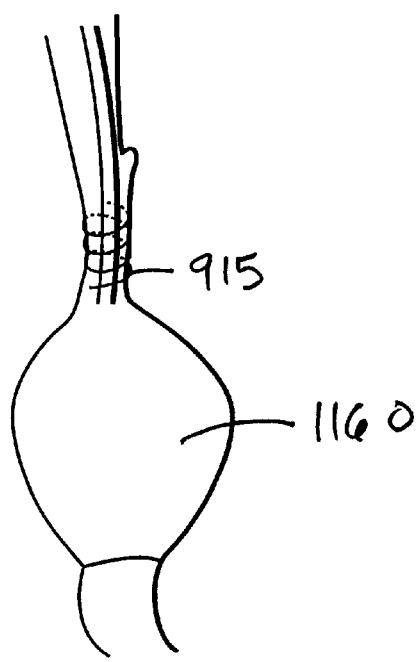
Figure 71:
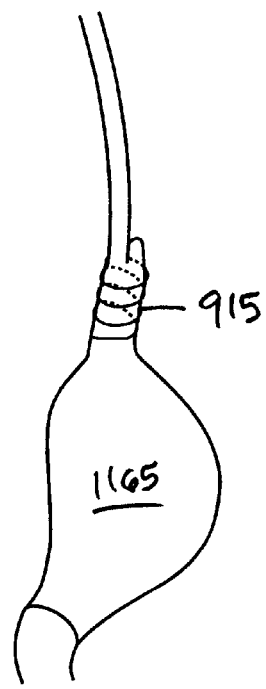

A procedure for treating morbid obesity using one or more of the previously described embodiments of the invention is now described with reference to FIGS. 68–71. Current approaches to morbid obesity treatment require laparoscopic invasion of the peritoneal cavity, or open procedure. Use of devices according to the embodiments of the invention, on the other hand, can allow construction of a reduced-volume gastric pouch to limit food intake via the transoral route. To limit the size of the gastric pouch and hence cause early satiety, deployment device 900 (or a deployment device according to one of the other embodiments illustrated herein) is placed transorally in stomach 1160, as shown in FIG. 68. A vacuum then is applied to draw the fundus of stomach 1160 generally to or toward the mandrel of deployment device 900, with reference to FIG. 69. Helical staple 915 then is applied/deployed, as in FIG. 70, and deployment apparatus 900 then is removed as in FIG. 71, leaving a gastric pouch 1165 of reduced size.

Gastroesophageal Reflux

Reconstruction of the lower esophageal sphincter (LES) can be accomplished according to device and method embodiments of the invention. Current procedures require laparoscopic invasion of the peritoneal cavity or open incision. Use of vacuum deployment devices and e.g. helical staples 915 according to the invention, on the other hand, can allow reconstruction of the LES per os, without necessity for entering the peritoneal cavity. To restore normal diameter and reduce reflux, deployment apparatus 900 (or other deployment apparatus) is placed within the esophagus. To restore a normal diameter, a vacuum is applied and helical staple 915 or similar stabilizing or fastening agent is deployed to restore the esophageal diameter.

Treatment of Varicose Veins

1. Extremity veins

Figure 72:
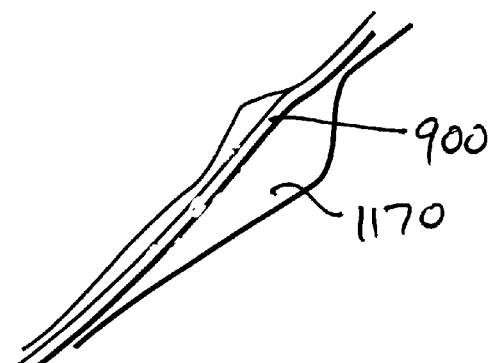
FIGS. 72–74 show operational steps in use of an apparatus for treatment of varicose veins, according to an embodiment of the invention.
Figure 73:
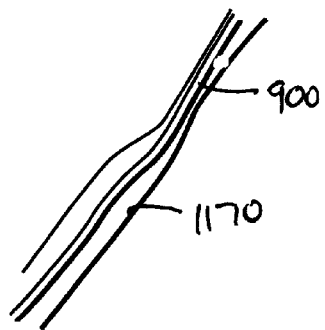
Figure 74:
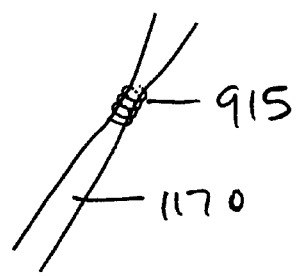

Varicose veins arise in part from loss of competence of venous valves. In one embodiment, vacuum deployment device 900 can be placed in the lumen of varicosity 1170 (FIG. 72). Vacuum is applied to constrict the walls of varicosity 1170 to the diameter of the vacuum device (FIG. 73), and the helical staple is deployed (FIG. 74), to provide permanent reduction in the diameter of the vein. Additionally, or alternatively, a closing off of the varicosity instead of mere constriction of it, e.g. in the manner of that previously described with respect to fallopian tube closure, can be performed. Collateral circulation then picks up the venous return.

2. More central veins

Hydrostatic pressure head may originate in pelvic veins, including gonadal veins. Closure or reduction of the diameter of these veins may increase the success of the treatment of extremity varicosities. In one embodiment, a vacuum deployment device according to the invention is threaded into the more central vein. Vacuum is applied and the helical staple is deployed, either within the wall of the vein, or extraluminally. If the diameter is adjusted to be small enough, sufficient hydrostatic pressure may be relieved to reduce pressure in varicosities in the lower extremities, while still maintaining flow in the vein that was to be treated. If desired, the diameter can be made small enough such that the vein undergoes thrombosis or is obliterated.

3. Treatment of venous strictures

Occlusion of large veins, including, but not limited to, the femoral veins, iliac veins, inferior vena cava, and superior vena cava, may occur as a result of thrombus or other mechanism for stricture. Significant morbidity, including swelling, skin-breakdown, ulceration, non-healing wounds, tissue necrosis, sepsis, and phlegmasia cerulean dolans, may occur. In one embodiment of the helical staple-vacuum deployment system according to the invention, the lumens of the relevant veins are maintained. In this application, the diameter of the vacuum device is such that the lumen of the vein is maintained at the diameter deemed optimal to maintain blood flow and flow velocity. Application of the vacuum brings the vein into contact with the vacuum deployment device of the appropriate diameter. The staple is deployed and the vein then is maintained at the fixed diameter. An advantage of the procedure of the invention over e.g. intraluminal stents relates to leaving the venous endothelium intact. The prosthetic material can be within the venous wall, according to embodiments of the invention, or within the adventitia surrounding the vein. In contradistinction to intraluminal devices, the endothelium is intact, with the likely consequence of reduced incidence of thrombus.

Use of Helical Staple When Open Procedure is Performed

Should an open surgical procedure be necessary, the vacuum deployment device-staple embodiments described herein still may be used. A modification for certain open procedures, however, modifies the staple/holding device and/or the type of deployment. A helical staple, for example, can be modified to be a piece of continuous material, for example stainless steel, nitinol, other metal, other nonabsorbable suture, other absorbable suture, or elastomer. In one embodiment, the continuous material can have a needle attached. Using the appropriate incision for exposure, the needle is placed extraluminally to form the helical staple, either within the luminal structure's wall or adventitia or other surrounding tissue.

Regarding the type of deployment, placement of the staple can be performed beginning proximally and proceeding distally, or beginning distally and proceeding proximally. In other words, a staple can be advanced both away from the operator, in the manner of previously described embodiments, or toward the operator, as may be desired in certain situations. Use of the vacuum device also can be performed beginning proximally and proceeding distally, or beginning distally and proceeding proximally.

Figure 75:
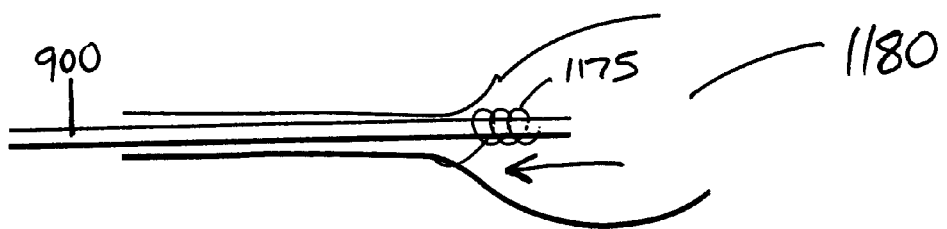
FIG. 75 shows an alternative method of staple deployment, according to an embodiment of the invention.
Figure 76:
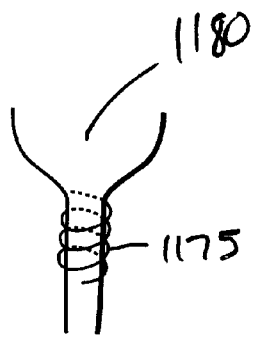
FIGS. 76–77 show placement of a generally helical stabilizing or fastening agent in an anatomical structure, according to an embodiment of the invention.
Figure 77:
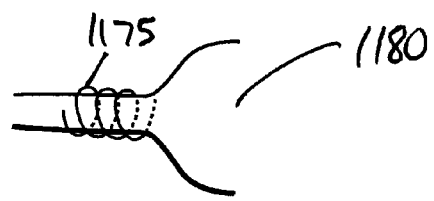

In the treatment of stress urinary incontinence, for example, device 900 is placed in urinary bladder 1180, FIGS. 75–77. The vacuum component of the deployment device then operates on the relevant portion of the tissue. A modified staple 1175, e.g. continuous stainless steel with an attached needle or one of the other modified staples referenced above, then pierces the tissue, also generally as described above. The pitch of the staple and the direction of the helix, in the case of a staple having a helical shape, then drives the staple toward the operator, as indicated by the arrow in FIG. 75.

Endovascular Procedures—Aneurysms

Dilation of arteries, e.g. aneurysms, is treatable by using the vacuum applied by embodiments of the invention to reduce the diameter of the blood vessel. With the wall of the blood vessel drawn into appropriately sized and shaped slots or otherwise into a desired configuration, a helical staple or other stabilizing or fastening agent is deployed to provide permanent reduction in the diameter of the aneurysmal vessel.

Endovascular Procedures—Strictures

Strictures of blood vessels are treatable by dilation of the structure. Once dilated, e.g. by an inflatable balloon as referenced earlier, a vacuum deployment device of appropriate diameter is placed in the area of the previously dilated stricture. The walls of the blood vessel are then drawn into appropriately sized and shaped slots or apertures, for example, in the vacuum device, and the helical staple or other stabilizing or fastening agent is then deployed. In this embodiment, a helical staple provides permanent increase in the diameter of the blood vessel that would be closely approximated by the diameter of the staple. A pressure differential device according to this embodiment is constructed to create both a positive pressure differential (with inflation of the balloon) and a negative pressure differential (with application of vacuum or suction). The other embodiments described in this patent application generally all can create positive pressure differential, negative pressure differential, or both.

Biliary Tract—Strictures

Bile duct strictures can be treated in a procedure analogous to that described for vascular strictures, above.

Rectal Incontinence

Vacuum deployment-staple devices according to embodiments of the invention can be used to narrow the lumen of the rectum and support the perirectal structures to generally prevent, minimize or reduce fecal incontinence.

Rectal Stricture

Vacuum deployment-staple devices according to embodiments of the invention can be used to functionally "stent" the anorectal canal in the case of anorectal stricture, without using a typical stent and enduring its disadvantages.

Rectal or Uterine Prolapse

Vacuum deployment-staple devices according to embodiments of the invention are used to support the perirectal or periuterine structures to prevent prolapse of the rectum or uterus, respectively.

Treatment of Hemorrhoids

Vacuum deployment-staple devices according to embodiments of the invention can be used in the treatment of hemorrhoids. The rectum is constricted and the e.g. helical staple used to ligate the hemorrhoidal veins. Alternatively, or additionally, the embodiments described herein can be used to stabilize or otherwise configure the tissue for appropriate treatment with another, separate device.

Gastrointestinal Stricture

Vacuum deployment-staple devices according to embodiments of the invention are used in similar fashion to functionally "stent" any gastrointestinal stricture that can be reached by the device, without using a typical stent and enduring its disadvantages. Use of long and flexible delivery catheter that can be placed with fluoroscopic guidance, for example, can facilitate placement of the deployment device in the relevant portion of the gastrointestinal tract. Such a therapeutic approach may have significant value in the treatment of inflammatory bowel disease, especially Crohn's disease.

Intussusception or Gastrointestinal Prolapse

Vacuum deployment-staple devices according to embodiments of the invention can be placed in a portion of the intestinal tract that is subject to intussusception. Use of long and flexible delivery catheter that can be placed with fluoroscopic guidance, for example, can facilitate placement of the deployment device in the relevant portion of the gastrointestinal tract. Deployment of the staple can stabilize the surrounding structures to prevent further intussusception. Such a therapeutic approach may have significant value in the treatment of pediatric intussusception or intussusception in the adult.

Gastric Outlet Obstruction

Gastric outlet obstruction may occur in the newborn, e.g. in hypertrophic pyloric stenosis, or due to other illnesses, including peptic ulcer disease and neoplastic disease. Vacuum deployment-staple devices according to embodiments of the invention can be placed through the obstructing lesion and the staple used to functionally "stent" the obstructed portion of the gastrointestinal tract, without using a typical stent and enduring its disadvantages.

Esophageal Obstruction

Esophageal obstruction may occur from inflammatory or neoplastic processes. Vacuum deployment-staple devices according to embodiments and the invention can be placed through the obstructing lesion and the staple used to functionally "stent" the obstructed portion of the gastrointestinal tract, without using a typical stent and enduring its disadvantages.

Urinary Incontinence

As referenced earlier in this patent application, embodiments of the invention treat urinary incontinence in female and male patients. According to one treatment protocol, the urinary bladder is drained of urine. The staple deployment device is positioned transurethrally such that a balloon-tipped catheter is placed in the urinary bladder. The balloon is inflated and withdrawn to the bladder neck to provide the operator with tactile information about the position of the bladder neck. The deployment device contains provision for applying a vacuum to the bladder, bladder neck, and/or the proximal urethra. With the vacuum applied, the relevant tissue of the bladder neck and the proximal urethra is drawn into e.g. slots in the deployment device that are designed to accommodate the relevant tissue. The tissue, drawn into the slots by the vacuum, is then positioned for firing or other application of the staple. The deployment device contains a drive mechanism for placing the helical staple into the tissue. With the staple deployed, the balloon at the catheter tip is deflated and the deployment device is removed. The staple is left in place in the tissue. Depending upon the configuration of the staple, a small extension, or tang, may be present to facilitate staple removal after tissue healing and fibrosis can occur.

Additionally, for e.g. an end-to-end anastomosis in the context of a urinary incontinence procedure, the ends of the urethra are approximated over the vacuum deployment device. The urethra, proximal and distal ends, are held in contact by the vacuum. Appropriately sized slots, apertures or the like are present in the vacuum deployment device to accommodate the tissue, according to one embodiment. A helical staple or other stabilizing or fastening agent is deployed to effect an anastomosis. In another embodiment, especially for end-to-side and side-to-end anastomoses, the deployment device and the staple are modified to have appropriately sized and shaped slots to accommodate the end of the urethra and the side of the proximal or distal urethra to which it is anastomosed. In this embodiment, the tissue is held in place by the vacuum, and the staple is modified to function as a linear press-fit staple rather than as a helical staple.

With incontinence-related embodiments according to the invention, the urethra and bladder neck region are supported in a substantially normal anatomic configuration, allowing the sphincter to act normally without the downward and radial forces of the bladder fluid on it. Permanent correction of e.g. USI is achieved, using minimally invasive techniques and with minimal or no necrosis of the tissue.

Conclusion

While the invention has been described with respect to particular embodiments, the description herein is intended to be illustrative and not limiting. For example, although specific reference has been made to the treatment of incontinence and to the urethra and bladder, embodiments of the invention can be used to repair, sustain and/or stabilize many other anatomical structures, such as the rectum, anal canal, liver or the other organs and structures referenced herein, as well as other organs and structures. Embodiments for treatment of incontinence in male patients can be of greater length than those for use in female patients; dimensions and materials for all embodiments can generally be chosen in accordance with particular anatomies or other parameters. Further, the procedures described herein can be performed without creating a vacuum/suction negative pressure differential or a positive pressure differential; treatment of the urethra/bladder neck or other anatomical structure can be accomplished with alternative physical maneuvering by the disclosed apparatus, a different apparatus, or manually.

Although reference to particular deployment devices is made throughout the application, e.g. deployment device 900, any of the deployment devices or treatment apparatus described herein generally can be used. Additionally, devices such as 900 and the others can be used just to stabilize or configure anatomical structure, in the manner of a purse-string suture, for example, with stapling or other treatment performed separately or by a separate device, such a circular surgical stapler, a cauterization device, or other device. A device such as 900 thus effectively takes the place of the purse-string suture, which provides significant advantages due to the relatively difficult nature of using such suture in certain contexts. Particular embodiments also involve helical staples, but it should be understood that any other suitable type of staple, stabilizing or fastening agent or holding device, such as biological adhesive or other adhesive, can be used instead. All of the embodiments described herein can be disposed within the lumen of an anatomical structure for treatment, or disposed extraluminally. As will be apparent to those of ordinary skill, the structures and other concepts disclosed with respect to one embodiment or figure can be applied in combination with those of any other embodiments or figures. Various other modifications and changes will be apparent to those of ordinary skill.

What is claimed is:

1. Apparatus for treatment of anatomical structure having a lumen, the apparatus comprising:
   a pressure differential device constructed to create a pressure differential with respect to the lumen of the anatomical structure, to cause movement of the anatomical structure to a desired configuration for treatment; and
   a stabilizing device, operably coupled with the pressure differential device, constructed to stabilize the anatomical structure in the desired configuration.

2. The apparatus of claim 1, wherein the pressure differential device is constructed to create a negative pressure differential relative to luminal pressure of the anatomical structure.

3. The apparatus of claim 2, wherein the pressure differential device comprises a vacuum source or suction source.

4. The apparatus of claim 3, wherein the pressure differential device is constructed and arranged to cause constriction of the anatomical structure to the desired configuration.

5. The apparatus of claim 4, wherein the pressure differential device is constructed and arranged to aid in performing at least one of treatment of incontinence, tubal ligation, vasectomy, treatment of morbid obesity, and treatment of varicose veins.

6. The apparatus of claim 4, wherein the pressure differential device is also constructed and arranged to create a positive pressure differential relative to luminal pressure of the anatomical structure to cause dilation of the anatomical structure.

7. The apparatus of claim 3, constructed to cause the anatomical structure to close tightly on itself upon application of the negative pressure.

8. The apparatus of claim 7, wherein the stabilizing device comprises a helical staple and helical-staple applicator, the applicator applying the helical staple to the anatomical structure after the anatomical structure has closed upon itself.

9. The apparatus of claim 7, constructed to cause at least one of a fallopian tube and a vas deferens to close tightly on itself upon application of the negative pressure.

10. The apparatus of claim 7, further comprising a wire constructed to deploy within the lumen of the anatomical structure to damage the anatomical structure before the anatomical structure is stabilized by the stabilizing device.

11. The apparatus of claim 10, wherein the wire is a resistive wire for applying heat to the anatomical structure.

12. The apparatus of claim 1, wherein the pressure differential device is constructed to create a positive pressure differential relative to luminal pressure of the anatomical structure.

13. The apparatus of claim 12, wherein the pressure differential device is constructed and arranged to cause dilation of the anatomical structure to the desired configuration.

14. The apparatus of claim 13, wherein the pressure differential device is constructed and arranged to aid in performing at least one of an angioplasty procedure in a coronary artery, a reversal of functional tubal ligation, a reversal of functional vasectomy, and functional stenting of an anatomical structure having a stricture without using a stent.

15. The apparatus of claim 12, wherein the pressure differential device comprises an inflatable balloon.

16. The apparatus of claim 1, wherein the stabilizing device comprises structure for applying a holding device to the anatomical structure, the holding device being constructed to remain applied to the anatomical structure after removal of the apparatus from the vicinity of the anatomical structure.

17. The apparatus of claim 1, wherein the stabilizing device comprises a holding device for application to the anatomical structure, the holding device remaining applied to the anatomical structure after removal of the apparatus from the vicinity of the anatomical structure.

18. The apparatus of claim 17, wherein the holding device remains completely outside of the lumen.

19. The apparatus of claim 1, wherein the lumen of the anatomical structure is reduced when the anatomical structure is in the desired configuration.

20. The apparatus of claim 1, wherein the lumen of the anatomical structure is enlarged when the anatomical structure is in the desired configuration.

21. The apparatus of claim 1, wherein the stabilizing device comprises a helical staple.

22. The apparatus of claim 21, wherein the helical staple remains completely outside of the lumen.

23. The apparatus of claim 1, wherein the pressure differential device comprises a set of suction apertures fluidly coupled to a suction source, the set of suction apertures constructed and arranged to cause movement of the anatomical structure to the desired configuration.

24. The apparatus of claim 23, wherein the set of suction apertures is a first set of suction apertures, the pressure differential device further comprising a second set of suction apertures fluidly coupled to a suction source, the first set of suction apertures and the second set of suction apertures being constructed and arranged to cause relative movement of two portions of the anatomical structure toward each other to facilitate formation of an anastomosis.

25. The apparatus of claim 24, wherein at least one of the sets of suction apertures is constructed to move toward the other of the sets of suction apertures to form the anastomosis.

26. The apparatus of claim 25, wherein said at least one set of suction apertures is constructed to be moved by an operator of the apparatus simultaneously with application of suction via the suction apertures to form the anastomosis.

27. The apparatus of claim 1, wherein the pressure differential device comprises a plurality of suction apertures fluidly coupled with a suction source, the plurality of suction apertures being constructed and arranged to cause relative movement of two portions of the anatomical structure toward each other to facilitate formation of an anastomosis.

28. The apparatus of claim 27, wherein at least one of the suction apertures is constructed to move toward at least one other of the suction apertures to form the anastomosis.

29. The apparatus of claim 28, wherein the stabilizing device comprises a surgical fastener and an applicator for applying the surgical fastener to the anatomical structure.

30. The apparatus of claim 29, further comprising a generally cylindrical member operably coupled with the stabilizing device and pressure differential device, further wherein the surgical fastener, the applicator and at least one of the suction apertures are disposed around the generally cylindrical member.

31. The apparatus of claim 30, wherein the generally cylindrical member is a first generally cylindrical member, the apparatus further comprising a second generally cylindrical member operably coupled with the stabilizing device and the pressure differential device, further wherein at least another of the suction apertures is disposed around the second generally cylindrical member, the first generally cylindrical member and the second generally cylindrical member being generally concentric and disposed for relative movement between them.

32. The apparatus of claim 1, further comprising a guide operably coupled with the stabilizing device to guide movement of the anatomical structure.

33. The apparatus of claim 32, wherein the guide is movable between a deployed configuration and an non-deployed configuration.

34. The apparatus of claim 33, wherein the guide comprises one of an inflatable material, memory material, and spring material.

35. The apparatus of claim 34, wherein the guide in the deployed configuration defines a generally conical-shaped opening for receiving anatomical structure therein.

36. The apparatus of claim 32, wherein the stabilizing device comprises a helical staple, further wherein the guide defines indentations for at least partially receiving the helical staple.

37. The apparatus of claim 32, wherein the guide defines a general cone shape when in the deployed configuration.

38. The apparatus of claim 32, constructed for at least one of vascular closure, wound closure, and ligation of gastrointestinal hemorrhage.

39. The apparatus of claim 1, further comprising a cutting device, operably coupled with the pressure differential device and the stabilizing device, for cutting the anatomical structure.

40. The apparatus of claim 39, further wherein the stabilizing device comprises repair material and structure for applying the repair material to the anatomical structure in the vicinity of the cut anatomical structure, the repair material remaining applied to the anatomical structure after removal of the apparatus from the vicinity of the anatomical structure.

41. Apparatus for treatment of anatomical structure having a lumen, the apparatus comprising:
a movement device constructed to cause movement of the anatomical structure to a desired configuration for treatment; and
a stabilizing device, operably coupled with the movement device, constructed to stabilize the anatomical structure in the desired configuration;
wherein the movement device comprises a cutting device for cutting the anatomical structure.

42. The apparatus of claim 41, further wherein the stabilizing device comprises structure for applying repair material to the anatomical structure in the vicinity of the cut anatomical structure, the repair material for remaining applied to the anatomical structure after removal of the apparatus from the vicinity of the anatomical structure.

43. The apparatus of claim 42, wherein the stabilizing device further comprises a surgical fastening agent to hold the repair material in place with respect to the anatomical structure.

44. The apparatus of claim 43, constructed and arranged for use in a blocked coronary artery.

45. The apparatus of claim 43, wherein the surgical fastening agent defines a helical shape.

46. The apparatus of claim 43, wherein the surgical fastening agent comprises a helical staple.

47. The apparatus of claim 41, wherein the stabilizing device comprises a helical staple and an advancement member for contacting the helical staple and advancing the helical staple into the anatomical structure after the cutting device has cut the anatomical structure.

48. The apparatus of claim 47, wherein the helical staple is constructed to hold repair material in place on the anatomical structure.

49. The apparatus of claim 42, constructed to cut anatomical structure and to apply repair material simultaneously due to a single continuous motion by an operator of the apparatus.

50. The apparatus of claim 42, further comprising a cutting device advancement mechanism for advancing the cutting device relative to the anatomical structure.

51. The apparatus of claim 50, wherein the cutting device advancement mechanism comprises a threaded screw.

52. The apparatus of claim 41, constructed to simultaneously cut the anatomical structure and apply the repair material to the anatomical structure.

53. The apparatus of claim 41, further comprising a cutting device advancement mechanism for advancing the cutting device relative to the anatomical structure.

54. The apparatus of claim 41, wherein the movement device further comprises a suction device for applying suction in the vicinity of the anatomical structure.

55. The apparatus of claim 42, wherein the movement device further comprises a suction device for applying suction in the vicinity of the anatomical structure.

56. The apparatus of claim 41, wherein the stabilizing device is constructed to remain completely outside of the lumen.

57. Apparatus for stabilizing an anatomical structure, the apparatus comprising:
means for moving the anatomical structure to or holding the anatomical structure in a desired configuration; and
means for deploying a stabilizing device into contact with the anatomical structure to hold the desired configuration;
wherein the stabilizing device can be deployed in a direction either toward an operator of the apparatus or away from an operator of the apparatus.

58. Apparatus for facilitating treatment of anatomical structure having a lumen, the apparatus comprising a pressure differential device constructed to cause movement of the anatomical structure to a desired, generally stabilized configuration by creating pressure differential from within the lumen, the desired configuration being suitable for further stabilization or treatment, the apparatus further comprising a member constructed to support the pressure differential device from within the lumen.

59. The apparatus of claim 58, wherein the pressure differential device comprises a suction device for drawing the anatomical structure toward the pressure differential device and into the desired configuration.

* * * * *